US011622995B2

(12) United States Patent
McLaughlin et al.

(10) Patent No.: US 11,622,995 B2
(45) Date of Patent: *Apr. 11, 2023

(54) TREATMENT OF POST-BARIATRIC HYPOGLYCEMIA WITH GLP-1 ANTAGONISTS

(71) Applicant: THE BOARD OF TRUSTEES OF THE LELAND STANFORD JUNIOR UNIVERSITY, Stanford, CA (US)

(72) Inventors: Tracey L. McLaughlin, Stanford, CA (US); Colleen M. Craig, Stanford, CA (US)

(73) Assignee: THE BOARD OF TRUSTEES OF THE LELAND STANFORD JUNIOR UNIVERSITY, Palo Alto, CA (US)

(*) Notice: Subject to any disclaimer, the term of this patent is extended or adjusted under 35 U.S.C. 154(b) by 63 days.

This patent is subject to a terminal disclaimer.

(21) Appl. No.: 17/226,161

(22) Filed: Apr. 9, 2021

(65) Prior Publication Data
US 2021/0290731 A1 Sep. 23, 2021

Related U.S. Application Data

(63) Continuation of application No. 16/813,536, filed on Mar. 9, 2020, now Pat. No. 10,993,992, which is a continuation of application No. 15/576,646, filed as application No. PCT/US2016/033836 on May 23, 2016, now Pat. No. 10,660,937.

(60) Provisional application No. 62/329,850, filed on Apr. 29, 2016, provisional application No. 62/254,175, filed on Nov. 11, 2015, provisional application No. 62/165,743, filed on May 22, 2015.

(51) Int. Cl.
A61K 38/17 (2006.01)
A61P 3/10 (2006.01)
A61K 38/22 (2006.01)
A61K 38/26 (2006.01)
A61P 3/08 (2006.01)
A61K 9/00 (2006.01)
A61K 45/06 (2006.01)
A61K 9/08 (2006.01)
A61K 9/10 (2006.01)

(52) U.S. Cl.
CPC ........ A61K 38/2278 (2013.01); A61K 9/0019 (2013.01); A61K 9/08 (2013.01); A61K 9/10 (2013.01); A61K 38/17 (2013.01); A61K 38/22 (2013.01); A61K 38/26 (2013.01); A61K 45/06 (2013.01); A61P 3/08 (2018.01)

(58) Field of Classification Search
CPC combination set(s) only.
See application file for complete search history.

(56) References Cited

U.S. PATENT DOCUMENTS

| | | |
|---|---|---|
| 5,424,286 A | 6/1995 | Eng |
| 6,004,297 A | 12/1999 | Steenfeldt-Jensen et al. |
| 6,268,343 B1 | 7/2001 | Knudsen et al. |
| 6,458,924 B2 | 10/2002 | Knudsen et al. |
| 6,469,021 B1 | 10/2002 | Truesdale et al. |
| 6,479,065 B2 | 11/2002 | Jaworowicz et al. |
| 6,495,164 B1 | 12/2002 | Ramstack et al. |
| 6,573,291 B2 | 6/2003 | Gronberg et al. |
| 6,667,061 B2 | 12/2003 | Ramstack et al. |
| 6,824,822 B2 | 11/2004 | Rickey et al. |
| 6,858,576 B1 | 2/2005 | Young et al. |
| 6,872,700 B1 | 3/2005 | Young et al. |
| 6,902,744 B1 | 6/2005 | Kolterman et al. |
| 6,903,074 B1 | 6/2005 | Morgan et al. |
| 6,956,026 B2 | 10/2005 | Beeley et al. |
| 7,223,440 B2 | 5/2007 | Rickey et al. |
| 7,235,627 B2 | 6/2007 | Knudson et al. |
| 7,238,663 B2 | 7/2007 | DeFelippis et al. |
| 7,297,761 B2 | 11/2007 | Beeley et al. |
| 7,456,254 B2 | 11/2008 | Wright et al. |
| 7,521,423 B2 | 4/2009 | Young et al. |
| 7,563,871 B2 | 7/2009 | Wright et al. |

(Continued)

FOREIGN PATENT DOCUMENTS

| | | |
|---|---|---|
| EP | 1609478 A1 | 12/2005 |
| JP | 2002-534450 A | 10/2002 |

(Continued)

OTHER PUBLICATIONS

Foster, "Hypoglycemia complicating bariatric surgery: incidence and Mechanisms," Curr Opin Endocrinol Diabetes Obes. 18(2): 129-133 (2011) (Year: 2011).*
Kim et al., "Plasma Glucose and Insulin Regulation Is Abnormal Following Gastric Bypass Surgery with or Without Neuroglycopenia," Obes. Surg. 19:1550-1556 (2009) (Year: 2009).*
"Amidation", The Free Dictionary, available at https://www.thefreedictionary.com/Amidation, retrieved online on Nov. 21, 2019, 3 pages.

(Continued)

Primary Examiner — Julie Ha
Assistant Examiner — Kristina M Hellman
(74) Attorney, Agent, or Firm — Kilpatrick Townsend & Stockton LLP

(57) ABSTRACT

Treatment of hyperinsulinemic hypoglycemia comprises administration of an effective amount of a glucagon-like peptide-1 receptor antagonist (GLP1RA) alone or in combination with an amylinomimetic agent or any anti-gastric emptying agent. Patients suffering from hyperinsulinemic hypoglycemia after bariatric surgery experience particular benefit, as there is no current method effective for their treatment. Prevention or reduction of acute adverse effects of postprandial hypoglycemia, such as palpitations, tremor, weakness, sweating, confusion, fatigue, blurred vision, seizures, or loss of consciousness, and prevention of chronic adverse effects of hyperinsulinemic hypoglycemia, such as cognitive impairment, can be achieved by treatment with GLP1RA.

25 Claims, 15 Drawing Sheets

(56) References Cited

U.S. PATENT DOCUMENTS

| | | | |
|---|---|---|---|
| 7,612,176 B2 | 11/2009 | Wright et al. |
| 7,741,269 B2 | 6/2010 | Young et al. |
| 8,076,288 B2 | 12/2011 | Levy et al. |
| 8,114,833 B2 | 2/2012 | Pedersen et al. |
| 8,216,180 B2 | 7/2012 | Tschirren et al. |
| 8,268,781 B2 | 9/2012 | Gotthardt et al. |
| 8,299,025 B2 | 10/2012 | Alessi et al. |
| 8,329,648 B2 | 12/2012 | Fineman et al. |
| 8,431,685 B2 | 4/2013 | Wright et al. |
| 8,439,864 B2 | 5/2013 | Galbraith et al. |
| 8,445,647 B2 | 5/2013 | Prickett et al. |
| 8,461,105 B2 | 6/2013 | Wright et al. |
| 8,546,326 B2 | 10/2013 | Joabsson et al. |
| 8,846,612 B2 | 9/2014 | Aprikian et al. |
| 8,895,033 B2 | 11/2014 | Houchin et al. |
| 8,906,851 B2 | 12/2014 | Fineman et al. |
| 8,969,293 B2 | 3/2015 | Imran |
| 9,616,108 B2 | 4/2017 | Stoffers et al. |
| 9,821,031 B2 | 11/2017 | Stoffers et al. |
| 10,188,702 B2 | 1/2019 | Stoffers et al. |
| 10,639,354 B2 | 5/2020 | McLaughlin et al. |
| 10,653,753 B2 | 5/2020 | Xiong |
| 10,660,937 B2 | 5/2020 | McLaughlin et al. |
| 10,987,407 B2 | 4/2021 | Stoffers et al. |
| 10,993,991 B2 | 5/2021 | McLaughlin et al. |
| 10,993,992 B2 | 5/2021 | McLaughlin et al. |
| 11,020,484 B2 | 6/2021 | Xiong et al. |
| 2002/0107277 A1 | 8/2002 | Gronberg et al. |
| 2002/0123461 A1 | 9/2002 | Drucker et al. |
| 2004/0092443 A1 | 5/2004 | Fridkin et al. |
| 2004/0116331 A1 | 6/2004 | Seeley et al. |
| 2008/0269130 A1 | 10/2008 | Stoffers et al. |
| 2010/0029554 A1 | 2/2010 | Ghosh et al. |
| 2011/0124555 A1 | 5/2011 | Schmid |
| 2013/0172250 A1 | 7/2013 | Fineman et al. |
| 2013/0195939 A1 | 8/2013 | Kidron |
| 2013/0252894 A1 | 9/2013 | Kuzma et al. |
| 2014/0256626 A1 | 9/2014 | Santi et al. |
| 2014/0309168 A1 | 10/2014 | Rosendahl |
| 2015/0005233 A1 | 1/2015 | DeFrees |
| 2015/0056285 A1 | 2/2015 | Houchin et al. |
| 2015/0057227 A1 | 2/2015 | Leung |
| 2015/0238568 A1 | 8/2015 | Fineman et al. |
| 2015/0258016 A1 | 9/2015 | Alessi et al. |
| 2015/0274800 A1 | 10/2015 | Schellenberger et al. |
| 2015/0368311 A1 | 12/2015 | Haack et al. |
| 2016/0185837 A1 | 6/2016 | Bednarek et al. |
| 2018/0117122 A1 | 5/2018 | McLaughlin et al. |
| 2018/0147261 A1 | 5/2018 | McLaughlin et al. |
| 2019/0336584 A1 | 11/2019 | Stoffers et al. |

FOREIGN PATENT DOCUMENTS

| | | |
|---|---|---|
| WO | 93/25579 | 12/1993 |
| WO | 2002-081649 A2 | 10/2002 |
| WO | 2008-085982 A2 | 7/2008 |
| WO | 2011-109787 A1 | 9/2011 |
| WO | 2016-191394 A1 | 12/2016 |
| WO | 2016-191395 A1 | 12/2016 |
| WO | 2018-094404 A1 | 5/2018 |

OTHER PUBLICATIONS

Alexopoulos K., et al., "Design and Synthesis of Novel Biologically Active Thrombin Receptor Non-Peptide Mimetics Based on the Pharmacophoric Cluster Phe/Arg/NH2 of the Ser42-Phe-Leu-Leu-Arg46 Motif Sequence: Platelet Aggregation and Relaxant Activities" J Med. Chem. vol. 47, Issue 13, Jun. 17, 2004, p. 3338-52, DOI:10.1021/jm031080v.

Andreasen, J.J., et al., "Secretion of Glucagon-Like Peptide-1 and Reactive Hypoglycemia after Partial Gastrectomy". Digestion, 1994. 55(4): p. 221-228.

Andronati, S.A. et al., "Peptidomimetics—Antagonists of the Fibrinogen Receptors: Molecular Design, Structures, Properties and Therapeutic Applications." Curr Med Chem 11(9): 1183-211, 2004.

Ashkenazi A., et al.,"Immunoadhesins". Int. Rev. Immunol., vol. 10, Issue 2-3, 1993, p. 219-227, DOI:10.3109/08830189309061697.

Bantle, J.P., et al., "Hyperinsulinemic Hypoglycemia Developing Late after Gastric Bypass", Obes Surg. vol. 17, https://doi.org/10.1007/s11695-007-9102-6, May 2007, p. 592-595.

Botros, N., et al., "Effect of Carbohydrate Restriction in Patients with Hyperinsulinemic Hypoglycemia after Roux-en-Y Gastric Bypass", Obes Surg. vol. 24, Issue 11, https://doi.org/10.1007/s11695-014-1319-6,Jun. 6, 2014, p. 1850-1855.

Breslin, M.J., et al., "Non-Peptide alphavbeta3 Antagonists. Part 6: Design and Synthesis of alphavbeta3 Antagonists Containing a Pyridone or Pyrazinone Central Scaffold". Bioorg & Med Chem Lett vol. 13, Issue 10, Jun. 2003, p. 1809- 12, DOI: 10.1016/S0960-894X(03)00254-3.

Buchwald, H., et al., "Long term, continuous intravenous heparin administration by an implantable infusion pump in ambulatory patients with recurrent venous thrombosis", Surgery, DOI:https://doi.org/10.5555/uri:pii:0039606080901257, vol. 88, Issue 4, Oct. 1, 1980, p. 507-516.

Calabria, A.C., et al., "Postoperative Surveillance and Detection of Postprandial Hypoglycemia after Fundoplasty in Children", published in final edited form as J Pediatr. vol. 159, No. 4, doi:10/1016/j.jpeds.2011.03.049,597-601. Oct. 2011, 11 pages.

Calabria, A.C., et al., "Postprandial Hypoglycemia in Children after Gastric Surgery: clinical characterization and pathophysiology", Horm Res Paediatr, vol. 85, No. 2, 2016, p. 140-146, DOI:10.1159/000442155.

Calabria, A.C., et al., "GLP-1 Receptor Antagonist Exendin-(9-39) Elevates Fasting Blood Glucose Levels in Congenital Hyperinsulinism Owing to Inactivating Mutations in the ATP-Sensitive K+ Channel" Diabetes, vol. 61, No. 10, Oct. 2012, 2585-2591, DOI:10.2337/db12-0166.

Cancelas, J., et al., "Resistance of Succinic Acid Dimethyl Ester Insulinotropic Action to Exendin (9-39) Amide", Hormone and Metabolic Research, vol. 34, No. 1, Feb. 1, 2002, pp. 13-15, DOI:10.1055/s-2002-19960.

Cancelas, J., et al., "Suppression by Exendin(9-39)amide of Glucagon-Like Peptide-1 Insulinotropic Action in Rats Infused with Dimethyl Ester of Succinic Acid", Endocrine, vol. 15, Issue 3, Aug. 2001, p. 283-5, DOI:10.1385/ENDO:15:3:283.

Caudy, A.A., et al. "Fragile X-related protein and VIG associate with the RNA interference machinery", Genes & Development, vol. 16, No. 19, 2002, p. 2491-2496, DOI:10.1101/gad.1025202.

Chen, T., et al., "Interspecies Modeling and Prediction of Human Exenatide Pharmacokinetics", Pharm Res., vol. 30, No. 3, Mar. 2013, p. 751-760, DOI:10.1007/s11095-012-0917-z.

Cheon, H.G., et al., "High-affinity binding sites for related fibroblast growth factor ligands reside within different receptor immunoglobulin-like domains", Proceedings of the National Academy of Science, vol. 91, No. 3, Feb. 1994, pp. 989-993, DOI:10.1073/pnas.91.3.989.

Corywell, W., "Depressive Disorders", Merck Manuals Professional Edition, retrieved on Jun. 11, 2019 from https://www.merckmanuals.com/professional/psychiatric-disorders/mood-disorders/depressive-disorders, p. 1-10.

Cosgrove, K.E., et al., "BPDZ 154 Activates Adenosine 5'-Triphosphate-Sensitive Potassium Channels: In Vitro Studies Using Rodent Insulin-Secreting Cells and Islets Isolated from Patients with Hyperinsulinism", The Journal of Clinical Endocrinology and Metabolism, vol. 87, No. 11, DOI:https://doi.org/10.1210/jc.2002-020439, Nov. 1, 2002, 4860-4868.

Craig, C.M., et al. "Critical role for GLP-1 in symptomatic post-bariatric hypoglycaemia", Diabetologia, vol. 60, Issue 3, DOI:https://doi.org/10.1007/s00125-016-4179-x, Published in final edited form on Mar. 2017, p. 531-540.

Craig, C.M., et al., "Efficacy and pharmacokinetics of subcutaneous exendin (9-39) in patients with post-bariatric hypoglycaemia", Diabetes, Obesity and Metabolism, vol. 20, Issue 2, DOI:https://doi.org/10.1111/dom.13078, 2017, p. 1-10.

Cryer, P.E., et al., "Evaluation and management of adult hypoglycemic disorders: an Endocrine Society Clinical Practice Guideline",

(56) References Cited

OTHER PUBLICATIONS

Journal of Clinical Endocrinology and Metabolism, vol. 94, Issue 3, Mar. 2009, p. 709-728, DOI:10.1210/jc.2008-1410.
Davidson, M.B, et al., "Exenatide," Nature Reviews Drug Discovery, vol. 4, DOI:10.1038/nrd1828, Sep. 2005, p. 713-714.
De Leon, D.D., "Effect of Exendin-(9-38) on Glycemic Control in Subjects With Congenital Hyperinsulinism", U.S. National Library of Medicine, ClinicalTrials.gov, retrieved on Nov. 21, 2019 from https://www.clinicaltrials.gov/ct2/show/NCT00571324, 28 pages.
De Leon, D.D., et al. "Exendin-(9-39) Corrects Fasting Hypoglycemia in SUR-1 / Mice by Lowering cAMP in Pancreatic beta-cells and Inhibiting Insulin Secretion" Journal of Biological Chemistry, vol. 283, Issue 38, Sep. 19, 2008, 24 pages, DOI:10.1074/jbc.M804372200.
De Leon, D.D., et al. "Role of Endogenous Glucagon-Like Peptide-1 in Islet Regeneration After Partial Pancreatectomy", Diabetes, vol. 52, Feb. 2003, p. 365-371, doi.org/10.2337/diabetes.52.2.365.
De Leon, D.D., et al., "Determination of insulin for the diagnosis of hyperinsulinemic hypoglycemia", Best Practice & Research Clinical Endocrinology & Metabolism, vol. 27, Issue 6, Dec. 2013, p. 763-769, doi.org/10.1016/j.beem.2013.06.005.
Deary, I.J., et al., "Partitioning the symptoms of hypoglycaemia using multi-sample confirmatory factor analysis", Diabetologia, vol. 35, Issue 8, DOI:https://doi.org/10.1007/BF00401150, 1993, p. 771-777.
Drucker, D.J., et al. "Biologic actions and therapeutic potential of the proglucagon-derived peptides", Nature Clinical Practice Endocrinology & Metabolism, vol. 1, No. 1, Nov. 2005, p. 22-31, DOI:10.1038/ncpendmet0017.
Dunne, M.J., et al. "Hyperinsulinism in Infancy: From Basic Science to Clinical Disease", Physiological Reviews, vol. 84, No. 1, DOI:10.1152/physrev.00022.2003, Jan. 2004, p. 239-275.
Edwards, C.M., et al. "Glucagon-like peptide 1 has a physiological role in the control of postprandial glucose in humans: studies with the antagonist exendin 9-39", Diabetes, vol. 48, No. 1, Jan. 1999, p. 86-93, doi.org/10.2337/diabetes.48.1.86.
Edwards, C.M., et al., "Subcutaneous glucagon-like peptide-1 (7-36) amide is insulinotropic and can cause hypoglycaemia in fasted healthy subjects", Clin Sci (Lond), vol. 95, No. 6, Dec. 1, 1998, p. 719-724, doi.org/10.1042/cs0950719.
Eisenberg, D., et al., "ASMBS Position Statement on Postprandial Hyperinsulinemic Hypoglycemia after Bariatric Surgery", Surgery for Obesity and Related Diseases, vol. 13, Issue 3, DOI:https://doi.org/10.1016/j.soard.2016.12.005, 2017, p. 371-378.
Eliasson, L., et al. "SUR1 Regulates PKA-independent cAMP-induced Granule Priming in Mouse Pancreatic B-Cells", J. Gen. Physiol, vol. 121, No. 3, DOI:10.1085/jgp.20028707, Mar. 2003, p. 181-197.
Eng, J., et al. "Isolation and Characterization of Exendin-4, an Exendin-3 Analogue, from Heloderma suspectum Venom: Further evidence for an exendin receptor on dispersed acini from guinea pig pancreas", The Journal of Biological Chemistry, vol. 267, No. 11, Apr. 15, 1992, p. 7402-7405.
Evan, G.I., et al., "Isolation of Monoclonal Antibodies Specific for Human c-myc Proto-Oncogene Product", Molecular and Cellular Biology, vol. 5, No. 12, Dec. 1985, p. 3610-3616.
Extended European Search Report dated Nov. 28, 2018 in European Patent Application No. 16800620.3, 5 pages.
Extended European Search Report dated Aug. 30, 2011 in European Application No. 08713063.9, 5 pages.
Extended European Search Report dated Dec. 1, 2014 in European Application No. 14171762.9, 6 pages.
Extended European Search Report dated Jan. 21, 2019 in European Application No. 18201976.0, 6 pages.
Extended European Search Report, dated Mar. 9, 2018, European Patent Application No. 16800621.1, 4 pages.
Field, J., et al., "Purification of a RAS-responsive Adenylyl Cyclase Complex from Saccharomyces cerevisiae by Use of an Epitope Addition Method", Molecular and Cellular Biology, vol. 8, No. 5, May 1988, p. 2159-2165, DOI:10.1128/mcb.8.5.2159.

Final Office action dated Oct. 23, 2019 in U.S. Appl. No. 15/576,647, 12 pages.
Final Office action dated Sep. 25, 2019 in U.S. Appl. No. 15/576,647, 16 pages.
Fournet, J.C., et al., "Unbalanced Expression of 11p15 Imprinted Genes in Focal Forms of Congenital Hyperinsulinism", The Amercian Journal of Pathology, vol. 158, No. 6, Jun. 2001, DOI:https://doi.org/10.1016/S0002-9440(10)64689-5, p. 2177-2184.
Franco, J.V., et al., "A Review of Studies Comparing Three Laparoscopic Procedures in Bariatric Surgery: Sleeve Gastrectomy, Roux-en-Y Gastric Bypass and Adjustable Gastric Banding," Obes Surg, vol. 21, No. 9, DOI:10.1007/s11695-011-0390-5, 2011, p. 1458-1468.
Gardiner, S., et al., "Mesenteric Vasoconstriction and Hindquarters Vasodilatation Accompany the Pressor Actions of Exendin-4 in Conscious Rats", Journal of Pharmacology and Experimental Therapeutics, vol. 316, No. 2, Feb. 2006, p. 852-859, doi.org/10.1124/jpet.105.093104.
Gebhard, B., et al., "Postprandial GLP-1, Norepinephrine, and Reactive Hypoglycemia in Dumping Syndrome", Digestive Diseases and Sciences, vol. 46, Issue 9, Sep. 2001, p. 1915-1923, doi.org/10.1023/A:1010635131228.
Goldfine, A.B., et al., "Patients with Neuroglycopenia after Gastric Bypass Surgery Have Exaggerated Incretin and Insulin Secretory Responses to a Mixed Meal", The Journal of Clinical Endocrinology & Metabolism, vol. 92, Issue 12, Dec. 1, 2007, p. 4678-4685, doi.org/10.1210/jc.2007-0918.
Goodson, J.M., Chapter 6 "Dental Applications" In: Medical Applications of Controlled Release, 1984, vol. 2, p. 116-138.
Gough, S.C.L, "Liraglutide: from clinical trials to clinical practice," Diabetes, Obesity and Metabolism, vol. 14, Issue 2, DOI:https://doi.org/10.1111/j.1463-1326.2012.01576.x, 2012, p. 33-40.
Heber, D., et al., "Endocrine and nutritional management of the post-bariatric surgery patient: an Endocrine Society Clinical Practice Guideline", J Clin Endocrinol Metab. vol. 95, Issue 11, DOI:10.1210/jc.2009-2128, Nov. 2010, p. 4823-4843.
Heidaran, M.A., et al., "Beta PDGFR-IgG chimera demonstrates that human beta PDGFR Ig-like domains 1 to 3 are sufficient for high affinity PDGF BB binding", The FASEB Journal, vol. 9, No. 1, Jan. 1, 1995, p. 140-145, doi.org/10.1096/fasebj.9.1.7821753.
Hepburn, D.A., et al., "Symptoms of acute insulin-induced hypoglycaemia in humans with and without IDDM", Diabetes Care, vol. 14, No. 11, DOI:https://doi.org/10.2337/diacare.14.11.949, Nov. 1991, p. 949-957.
Hofeldt, F.D., "Reactive hypoglycemia", Endocrinology and Metabolism Clinics of North America, vol. 18, No. 1, Mar. 1989, p. 185-201.
Hopp, T.P., et al., "A Short Polypeptide Marker Sequence Useful for Recombinant Protein Identification and Purification", Bio/Technology, vol. 6, No. 10, Oct. 1988, p. 1204-1210, DOI:10.1038/nbt1088-1204.
Hussain, K., et al., "Medications used in the treatment of hypoglycemia due to congenital hyperinsulinism of infancy (HI)", Pediatric Endocrinology Reviews, vol. 2, Supplement 1, Nov. 2004, p. 163-167.
International Hypoglycaemia Study Group (IHSG), Amiel, S.A., et al., "Glucose concentrations of less than 3.0 mmol/L (54 mg/dL) should be reported in clinical trials: A joint position statement of the American Diabetes Association and the European Association for the Study of Diabetes", Diabetes Care, vol. 40, DOI:10.2337/dc16/2215, Jan. 2017, p. 155-157.
International Preliminary Report on Patentability dated Apr. 14, 2021 in International Patent Application No. PCT/US2019/056278, 11 pages.
International Preliminary Report on Patentability dated May 21, 2019 in International Patent Application No. PCT/US2017/062838, 5 pages.
International Preliminary Report on Patentability dated Nov. 28, 2017 in International Patent Application No. PCT/US2016/033836, 11 pages.
International Preliminary Report on Patentability dated Nov. 28, 2017 in International Patent Application No. PCT/US2016/033837, 5 pages.

(56) References Cited

OTHER PUBLICATIONS

International Search Report and Written Opinion dated Aug. 18, 2016 in International Patent Application No. PCT/US2016/033837, 7 pages.
International Search Report and Written Opinion dated Aug. 19, 2016 in International Patent Application No. PCT/US2016/033836, 13 pages.
International Search Report and Written Opinion dated Jan. 15, 2020 in International Patent Application No. PCT/US2019/056278, 26 pages.
International Search Report and Written Opinion dated Jan. 23, 2018 in International Patent Application No. PCT/US2017/062838, 8 pages.
International Search Report and Written Opinion dated May 26, 2017 in International Patent Application No. PCT/US2017/020596, 10 pages.
International Search Report and Written Opinion dated Sep. 19, 2008 in International Patent Application No. PCT/US2008/000281, filed Jan. 8, 2008, 8 pages.
Jezek, J., et al., "Biopharmaceutical formulations for pre-filled delivery devices", Expert opinion on drug delivery, vol. 10, Issue 6, (2013): 811-828, DOI:10.1517/17425247.2013.780023.
Kapoor, R.R., et al., "Advances in the diagnosis and management of hyperinsulininemic hypoglycemia," Nature Clinical Practice Endocrinology & Metabolism, vol. 5, No. 2, DOI:https://doi.org/10.1038/ncpendmet1046, Feb. 2009, p. 101-112.
Kellogg, T.A., et al., "Postgastric bypass hyperinsulinemic hypoglycemia syndrome: characterization and response to a modified diet", Surgery for Obesity and Related Diseases, vol. 4, Issue 4, DOI:10.1016/j.soard.2008.05.005, Jul.-Aug. 2008, p. 492-499.
Kenny, C., "When Hypoclycemia is not obvious: diagnosing and treating under-recognized and undisclosed hypoglycemia", Primary Care Diabetes, vol. 8, Issue 1, DOI:http://dx.doi.org/10.1016/j.pcd.2013.09.002, Apr. 1, 2014, p. 3-11.
Kielgast, U., et al. "Antidiabetic Actions of Endogenous and Exogenous GLP-1 in Type 1 Diabetic Patients With and Without Residual µ-Cell Function", Diabetes, vol. 60, Issue 5, May 2011, p. 1599-1607, doi.org/10.2337/db10-1790.
Kim, S.H., et al., "Glucose-stimulated insulin secretion in gastric bypass patients with hypoglycemic syndrome: no evidence for inappropriate pancreatic beta-cell function", Obesity Surgery, vol. 20, Issue 8, DOI:https://doi.org/10.1007/s11695-010-0183-2, Aug. 2010, p. 1110-1116.
Koh, T H., et al., "Neonatal hypoglycaemia-the controversy regarding definition", Archives of Disease in Childhood, vol. 63, No. 11, Nov. 1988, p. 1386-1388, DOI:10.1136/adc.63.11.1386.
Kulkarni, R.N., et al., "Use of Exendin (9-39) Amide to define the in-vivo and in-vitro roles of GLP-1 (7-36) Amide in the regulation of Insulin secretion", Regulatory Peptides, vol. 57, No. 2, May 1995, p. 201.
Kumareswaran, K., et al. "Closed-loop Insulin Delivery: Towards Improved Diabetes Care", Discovery Medicine, vol. 13, No. 63, Feb. 23, 2012, p. 159-170.
Laferrere, B., et al., "Effect of weight loss by gastric bypass surgery versus hypocaloric diet on glucose and incretin levels in patients with type 2 diabetes", The Journal of Clinical Endocrinology & Metabolism, vol. 93, Issue 7, DOI:https://doi.org/10.1210/jc.2007-2851, Jul. 2008, p. 2479-2485.
Langa, K.M., et al., "The Diagnosis and Management of Mild Cognitive Impairment: A Clinical Review", JAMA, vol. 312, Issue 23, DOI:https://doi.org/10.1001/jama.2014.13806, Dec. 17, 2014, p. 2551-2561.
Langer, R., "New Methods of Drug Delivery", Science, vol. 249, Issue 4976, DOI:10.1126/science.2218494, Sep. 28, 1990, p. 1527-1533.
Larochelle, W.J., et al., "Specific Receptor Detection by a Functional Keratinocyte Growth Factor-Immunoglobulin Chimera", The Journal of Cell Biology, vol. 129, No. 2, Apr. 15, 1995, p. 357-366, doi.org/10.1083/jcb.129.2.357.
Larraufie, P., et al., "Important Role of the GLP-1 Axis for Glucose Homeostasis after Bariatric Surgery", Cell Reports, DOI:https://doi.org/10.1016/j.celrep.2019.01.047, vol. 26, Issue 6, Feb. 5, 2019, p. 1399-1408.
Lasaosa, M., et al. "A liquid chromatography-mass spectrometry assay for quantification of Exendin[9-39] in human plasma", J Chromatogr B Analyt Technol Biomed Life Sci., Feb. 1, 2014, p. 186-191, DOI:10.1016/j.jchromb.2013.12.010.
Lee, et al. "OR20-5 28-Day Dosing with Avexitide Improves Hyperinsulinemic Hypoglycemia in Patients with Severe, Refractory Post-Bariatric Hypoglycemia: The PREVENT Study", Journal of the Endocrine Society, vol. 3, Issue Supplement 1, Apr. 30, 2019, pp. 1-5, DOI:10.1210/js.2019-OR20-5.
Lev-Ran, A., et al., "The diagnosis of postprandial hypoglycemia", Diabetes, vol. 30, Issue 12, DOI:10.2337/diab.30.12.996, Dec. 1981, p. 996-999.
Lutz-Freyermuth, C., et al., "Quantitative determination that one of two potential RNA-binding domains of the A protein component of the U1 small nuclear ribonucleoprotein complex binds with high affinity to stem—loop II of U1 RNA", Proceedings of the National Academy of Sciences of the USA, vol. 87, Issue 16, Aug. 1990, p. 6393-6397, DOI:10.1073/pnas.87.16.6393.
Mandal, A., "Defining Hypoglycemia", News Medical: Life Sciences, retrieved on Nov. 20, 2019 from https://www.news-medical.net/health/Defining-Hypoglycemia.aspx, 3 pages.
Manning, S., et al. "GLP-1: A Mediator of the Beneficial Metabolic Effects of Bariatric Surgery?", Physiology, vol. 30, Issue 1, DOI:https://doi.org/10.1152/physiol.00027.2014, Jan. 1, 2015, p. 50-62.
Martin, G.A., et al., "GAP domains responsible for ras p21-dependent inhibition of muscarinic atrial K+ channel currents", Science, vol. 255, Issue 5041, Jan. 10, 1992, p. 192-194, DOI:10.1126/science.1553544.
Mclaughlin, T., et al. "Reversible Hyperinsulinemic Hypoglycemia after Gastric Bypass: A Consequence of Altered Nutrient Delivery", The Journal of Clinical Endocrinology & Metabolism, vol. 95, Issue 4, Apr. 1, 2010, pp. 1851-1855, doi.org/10.1210/jc.2009-1628.
Mechanick, J.I., et al., "Clinical practice guidelines for the perioperative nutritional, metabolic, and nonsurgical support of the bariatric surgery patient—2013 update: cosponsored by American Association of Clinical Endocrinologists", Obesity (Silver Spring), vol. 21, Issue 1, DOI:10.1002/oby.20461, Mar. 2013, 64 pages.
Meier et al., "Comment to: Patti ME, McMahon G, Mun EC et al. (2005) Severe hypoglycaemia post-gastric bypass requiring partial pancreatectomy: evidence for inappropriate insulin secretion and pancreatic islet hyperplasia. Diabetologia 49:2236-2240", Diabetologia, vol. 49, Issue 3, Mar. 2006, p. 607-608, DOI:10.1007/s00125-005-0114-2.
Meijeren, J.V., et al., "Evaluation of carbohydrate restriction as primary treatment for post-gastric bypass hypoglycemia", Surgery for Obesity and Related Diseases, vol. 13, Issue 3, DOI:https://doi.org/10.1016/j.soard.2016.11.004, Mar. 2017, p. 404-410.
Miholic, J., et al. "Emptying of the Gastric Substitute, Glucagon-like peptide-1 (GLP-1), and Reactive Hypoglycemia After Total Gastrectomy", Digestive Diseases and Sciences, vol. 36, No. 10, Oct. 1991, p. 1361-1370, doi.org/10.1007/BF01296800.
Moize, V.L., et al., "Nutritional pyramid for post-gastric bypass patients", Obesity Surgery, vol. 20, Issue 8, DOI:10.1007/s11695-010-0160-9, 2010, p. 1133-1141.
Montrose-Rafizadeh, C. et al. "High Potency Antagonists of the Pancreatic Glucagon-like Peptide-1 Receptor", The Journal of Biological Chemistry, vol. 272, Issue 34, DOI:10.1074/jbc.272.34.21201, Aug. 22, 1997, p. 21201-21206.
Myers, H.R., "Why Does Blood Pressure Drop After a Meal?", Livestrong.com, retrieved on Nov. 21, 2019, from http://www.livestrong.com/article/413792-postprandial-hypoglycemic-diet/, 2 pages.
Myint, K.S., et al., "Prolonged successful therapy for hyperinsulinaemic hypoglycaemia after gastric bypass: the pathophysiological role of GLP1 and its response to a somatostatin analogue", European Journal of Endocrinology, vol. 166, Issue 5, May 2012, p. 951-955, doi.org/10.1530/EJE-11-1065.
Nabel, E.G., "Cardiovascular Disease", The New England Journal of Medicine, vol. 349, Issue 1, DOI:10.1056/NEJMra035098, Jul. 3, 2003, p. 60-72.

(56) References Cited

OTHER PUBLICATIONS

National Center for Biotechnology Information, "PubChem Compound Summary for CID 129012199, Exendin (9-39)", Available from: https://pubchem.ncbi.nlm.nih.gov/compound/129012199. Accessed Sep. 26, 2020, pp. 1-36.

Naz, R.K, et al., "Novel human prostate-specific cDNA: molecular cloning, expression, and immunobiology of the recombinant protein", Biochemical and Biophysical Research Communications, vol. 297, Issue 5, Oct. 11, 2002, p. 1075-1084, doi.org/10.1016/S0006-291X(02)02349-5.

Ng, D.D., et al. 'Acarbose treatment of postprandial hypoglycemia in children after Nissen fundoplication', The Journal of Pediatrics, vol. 139, Issue 6, DOI:https://doi.org/10.1067/mpd.2001.119169, Dec. 2001, p. 877-879.

Nielsen, P.E., "Peptide nucleic acids as therapeutic agents", Current Opinion in Structural Biology, vol. 9, Issue 3, DOI: https://doi.org/10.1016/S0959-440X(99)80047-5, Jun. 1999, p. 353-357.

Non-Final Office action dated Mar. 21, 2019 in U.S. Appl. No. 15/576,647, 17 pages.

Office Action dated Feb. 22, 2019 in European Patent Application No. 16800621.1, 3 pages.

Paborsky, L.R., et al., "Mammalian cell transient expression of tissue factor for the production of antigen", Protein Engineering, Design and Selection, vol. 3, Issue 6, May 1990, p. 547-553, doi.org/10.1093/protein/3.6.547.

Pai, M. P., "Drug dosing based on weight and body surface area: mathematical assumptions and limitations in obese adults", Pharmacotherapy, vol. 32, Issue 9 (2012): 856-868, DOI:10.1002/j.1875-9114.2012.01108.x.

Palladino, A.A., et al., "Hyperinsulinism in Infancy and Childhood: When an Insulin Level is Not Always Enough", Clinical Chemistry, vol. 54, Issue 2, DOI:10.1373/clinchem.2007.098988, Jan. 2008, p. 256-263.

Palladino, A.A., et al., "Increased Glucagon-Like Peptide-1 secretion and Postprandial Hypoglycemia in Children after Nissen Fundoplication", The Journal of Clinical Endocrinology & Metabolism, vol. 94, Issue 1, DOI:10.1210/jc.2008-1263, Jan. 2009, p. 39-44.

Patti, M., et al., "Hypoglycemia after Gastric Bypass: The Dark Side of GLP-1", Gastroentrology, vol. 146, Issue 3, DOI:10.1053/j.gastro.2014.01.038, Mar. 2014, p. 605-608.

Patti, M.E., et al., "Severe hypoglycemia postgastric bypass requiring partial pancreatectomy: evidence for inappropriate insulin secretion and pancreatic islet hyperplasia", Diabetologia, vol. 48, Issue 11 (2005) p. 2236-2240, DOI:10.1007/s00125-005-1933-x.

Pramanick, S., et al., "Excipient Selection in Parenteral Formulation Development", Pharma Times, vol. 45, No. 3, Mar. 2013, p. 65-77.

Salehi, M., et al., "Blockade of Glucagon-like Peptide 1 Receptor Corrects Postprandial Hypoglycemia After Gastric Bypass", Gastroenterology, vol. 146, Issue 3, Mar. 2014, p. 669-680, doi.org/10.1053/j.gastro.2013.11.044.

Salehi, M., et al., "Gastric Bypass Surgery Enhances Glucagon-Like Peptide 1-Stimulated Postprandial Insulin Secretion in Humans", Diabetes, vol. 60, Issue 9, Sep. 2011, p. 2308-2314, doi.org/10.2337/db11-0203.

Saudek, C.D., et al., "A Preliminary Trial of the Programmable Implantable Medication System for Insulin Delivery", The New England Journal of Medicine, vol. 321, No. 9, DOI: 10.1056/NEJM198908313210904, Aug. 31, 1989, p. 574-579.

Schirra, J., et al., "Endogenous glucagon-like peptide 1 controls endocrine pancreatic secretion and antro-pyloro-duodenal motility in humans", Gut, vol. 55, Issue 2, Feb. 2006, p. 243-251, DOI:10.1136/gut.2004.059741.

Schirra, J., et al., "Exendin(9-39)amide Is an Antagonist of Glucagon-like Peptide-1 (7-36)amide in Humans", The Journal of Clinical Investigation, vol. 101, No. 7, Apr. 1, 1998, p. 1421-1430, doi.org/10.1172/JCI1349.

Scroochi, L.A., et al., "Glucose intolerance but normal satiety in mice with a null mutation in the glucagon-like peptide 1 receptor gene", Nature Medicine, vol. 2, No. 11, Nov. 1, 1996, p. 1254-1258, doi.org/10.1038/nm1196-1254.

Seaquist, E.R., et al., "Hypoglycemia and Diabetes: A Report of a Workgroup of the American Diabetes Association and the Endocrine Society", Diabetes Care, vol. 36, Issue 5, DOI:https://doi.org/10.2337/dc12-2480, May 2013, p. 1384-1395.

Sefton, M.V., "Implantable Pumps" Critical Reviews in Biomedical Engineering, vol. 14, Issue 3, Dec. 1986, p. 201-240.

Seghers, V., et al. "Sur 1 Knockout Mice. A Model for KATP Channel-Independent Regulation of Insulin Secretion", The Journal of Biological Chemistry, vol. 275, No. 13, DOI:10.1074/jbc.275.13.9270, Mar. 31, 2000, p. 9270-9277.

Service, F.J., et al., "Mean Amplitude of Glycemic Excursions, a Measure of Diabetic Instability", Diabetes, vol. 19, Issue 9, DOI:https://doi.org/10.2337/diab.19.9.644, Sep. 1970, p. 644-655.

Service, G.J., et al., "Hyperinsulinemic hypoglycemia with nesidioblastosis after gastric-bypass surgery", The New England Journal of Medicine, vol. 353, Issue 3, Jul. 21, 2005, p. 249-254, DOI:10.1056/NEJMoa043690.

Skinner, R.H., et al., "Use of the Glu-Glu-Phe C-terminal Epitope for Rapid Purification of the Catalytic Domain of Normal and Mutant ras GTPase-activating Proteins", The Journal of Biological Chemistry, vol. 266, No. 22, Issue of Aug. 5, 1991, p. 14163-14166.

Song, J., et al., "NMR for the design of functional mimetics of protein-protein interactions: one key is in the building of bridges", Biochemistry and Cell Biology, vol. 76, Issue 2-3, 1998, p. 177-188, DOI: 10.1139/bcb-76-2-3-177.

Stanley, C.A., et al., "Editorial: Advances in Diagnosis and Treatment of Hyperinsulinism in Infants and Children", The Journal of Clinical Endocrinology & Metabolism, vol. 87, Issue 11, Nov. 2002, p. 4857-4859, DOI:10.1210/jc.2002-021403.

Suhl, E., et al., "Medical nutrition therapy for post-bariatric hypoglycemia: practical insights", Surgery for Obesity and Related Diseases, vol. 13, Issue 5, DOI: 10.1016/j.soard.2017.01.025, May 2017, p. 888-896.

Tack, J., et al., "Pathophysiology, diagnosis and management of postoperative dumping syndrome", Nature Reviews Gastroenterology & Hepatology, vol. 6, Issue 10, DOI:https://doi.org/10.1038/nrgastro.2009.148, Sep. 1, 2009, p. 583-590.

Tan, M.J., et al., "Repeat subcutaneous dosing of exendin 9-39 reduces hyperinsulinemic hypoglycemia and neuroglycopenic symptoms in patients with post-bariatric hypoglycemia", Poster presentation at the American Diabetes Association's 77th Scientific Sessions, San Diego, CA, Jun. 9-13, 2017, 1 page.

Thanthan, S., et al., "Glucagon-like peptide-1 inhibits insulinotropic effects of oxyntomodulin and glucagon in cattle", Domestic Animal Endocrinology, vol. 42, Issue 3, DOI:https://doi.org/10.1016/j.domaniend.2011.11.004, Apr. 2012, p. 155-164.

Todd, J.F., et al., "A tumor that secretes glucagon-like peptide-1 and somatostatin in a patient with reactive hypoglycemia and diabetes", The Lancet, vol. 361, Issue 9353, Jan. 18, 2003, p. 228-230, doi.org/10.1016/S0140-6736(03)12256-8.

Toft-Nielsen, M., et al., "Exaggerated secretion of glucagon-like peptide-1 (GLP-1) could cause reactive hypoglycaemia", Diabetologia, vol. 41, Issue 10, 1998, p. 1180-1186, doi.org/10.1007/s001250051049.

Toft-Nielsen, M.-B., et al., "Determinants of the Effectiveness of Glucagon-Like Peptide-1 in Type 2 Diabetes", The Journal of Clinical Endocrinology & Metabolism, vol. 86, Issue 8, Aug. 1, 2001, p. 3853-3860, doi.org/10.1210/jcem.86.8.7743.

Traina, A.N., et al., "Primer on Pramlintide, an Amylin Analog", The Diabetes Educator, vol. 37, Issue 3, DOI:10.1177/0145721711403011, May/Jun. 2011, p. 426-431.

Vilsboll T., et al., No reactive hypoglycaemia in Type 2 diabetic patients after subcutaneous administration of GLP-1 and intravenous glucose Diabet Medicine, vol. 18, Issue 2, Dec. 20, 2001, p. 144-149, doi.org/10.1046/j.1464-5491.2001.00424.x.

Vogt, A., et al., "A Non-peptide Mimetic of Ras-CAAX: selective Inhibition of Farnesyltransferase and Ras Processing", The Journal of Biological Chemistry, vol. 270, No. 2, Issue of Jan. 13, 1995, pp. 660-664, doi.org/10.1074/jbc.270.2.660.

(56) References Cited

OTHER PUBLICATIONS

Webb, M., et al., "Growth restriction and exendin 4 promote endocrine expression in cultured islet cells derived from patients with persistent hyperinsulinemic hypoglycemia of infancy (PHHI)", Endocrine Research, vol. 31, Issue 2, DOI:10.1080/07435800500229235, 2005, p. 99-109.

Williard, F.S., et al., "Small Molecule Allosteric Modulation of the Glucagon-Like Peptide-1 Receptor Enhances the Insulinotropic Effect of Oxyntomodulin", Molecular Pharmacology, vol. 82, Issue 6, DOI:https://doi.org/10.1124/mol.112.080432, 2012, p. 1066-1073.

Craig, C.M., et al., "Subcutaneous exendin (9-39) effectively treats post-bariatric hypoglycemia," American Diabetes Association, 76th Scientific Sessions, Jun. 10-14, 2016; New Orleans, LA; Retrieved from the Internet at www.eigerbio.com/wp-content/uploads/2020/08/ADA-Exendin9-39-2016.pdf [retrieved on Jun. 2, 2022] * the whole document *.

Sim—Results of the Alignment of 2 Protein Sequences—Sequence alignment of instant SEQ ID No. 1 and instant SEQ ID No. 5 (retrieved from https://web.expasy.org/cgi-bin/sim/sim.pl?prot on May 11, 2022, 3 pages) (Year: 2022).

Office Action for Canadian Application No. 3,024,358 dated Jun. 6, 2022, 4 pages.

European Search Report for EP 19873113.5 dated Jun. 15, 2022, 10 pages.

European Search Report for EP 22156122 dated Jun. 22, 2022, all pages.

Supplementary European Search Report EP 19873113 dated Jun. 2, 2022, 10 pages.

\* cited by examiner

A

B

FIG. 2A-B
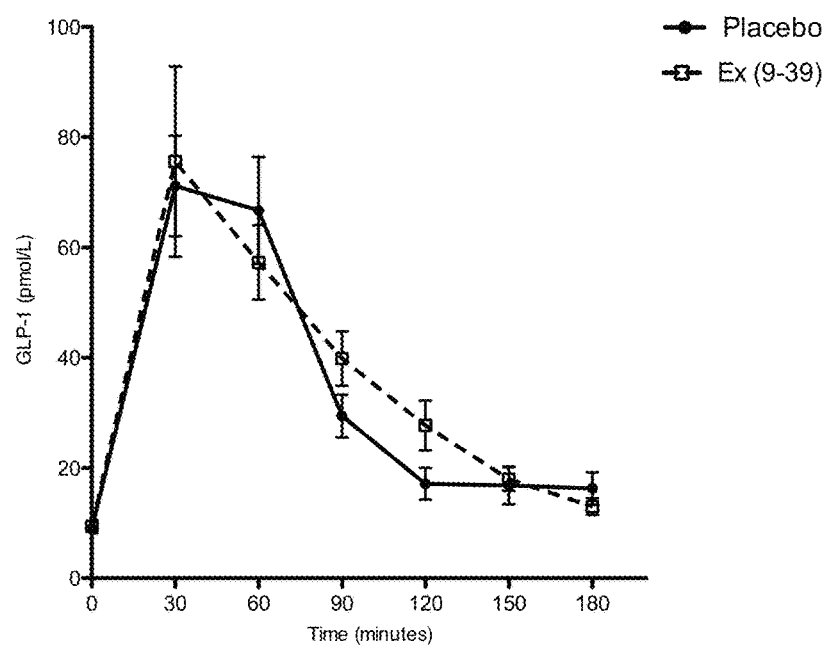
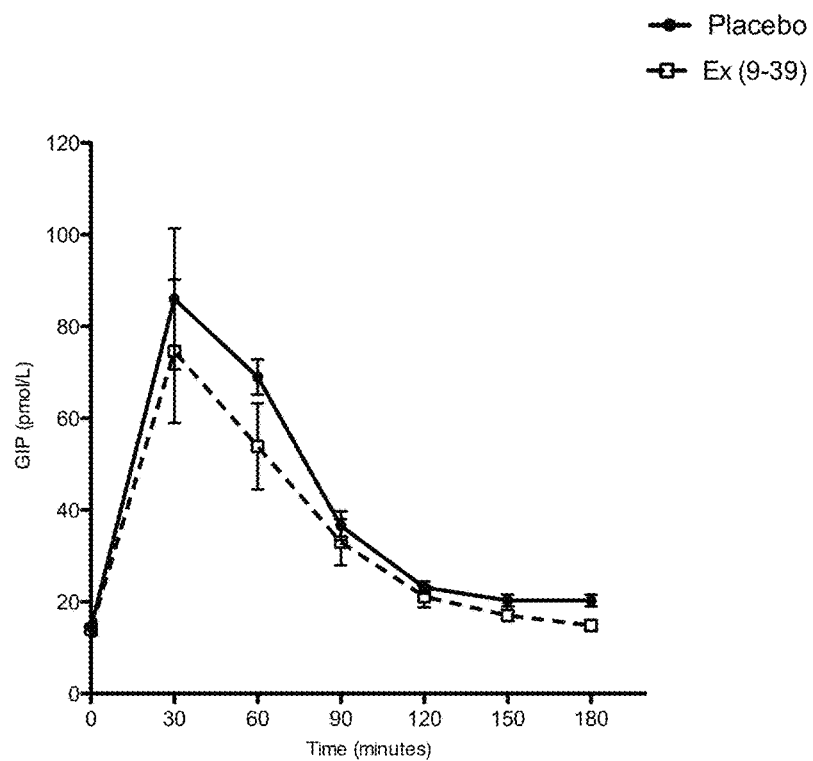

FIG. 3

| PLACEBO | | | |
|---|---|---|---|
| Subject | Overall Symptom Score | Glucose Rise Score* | Glucose Fall Score** |
| 1 | 33 | 25 | 22 |
| 2 | 41 | 8 | 41 |
| 3 | 29 | 10 | 21 |
| 4 | 31 | 12 | 24 |
| 5 | 20 | 9 | 20 |
| 6 | 17 | 3 | 17 |
| 7 | 10 | 4 | 8 |
| 8 | 36 | 15 | 36 |
| Average | 27 | 11 | 24 |

| EXENDIN 9-39 | | | |
|---|---|---|---|
| Subject | Overall Symptom Score | Glucose Rise Score* | Glucose Fall Score** |
| 1 | 0 | 0 | 0 |
| 2 | 4 | 4 | 0 |
| 3 | 0 | 0 | 0 |
| 4 | 3 | 3 | 1 |
| 5 | 6 | 6 | 2 |
| 6 | 19 | 19 | 2 |
| 7 | 14 | 14 | 4 |
| 8 | 2 | 2 | 2 |
| Average | 6 | 6 | 1 |

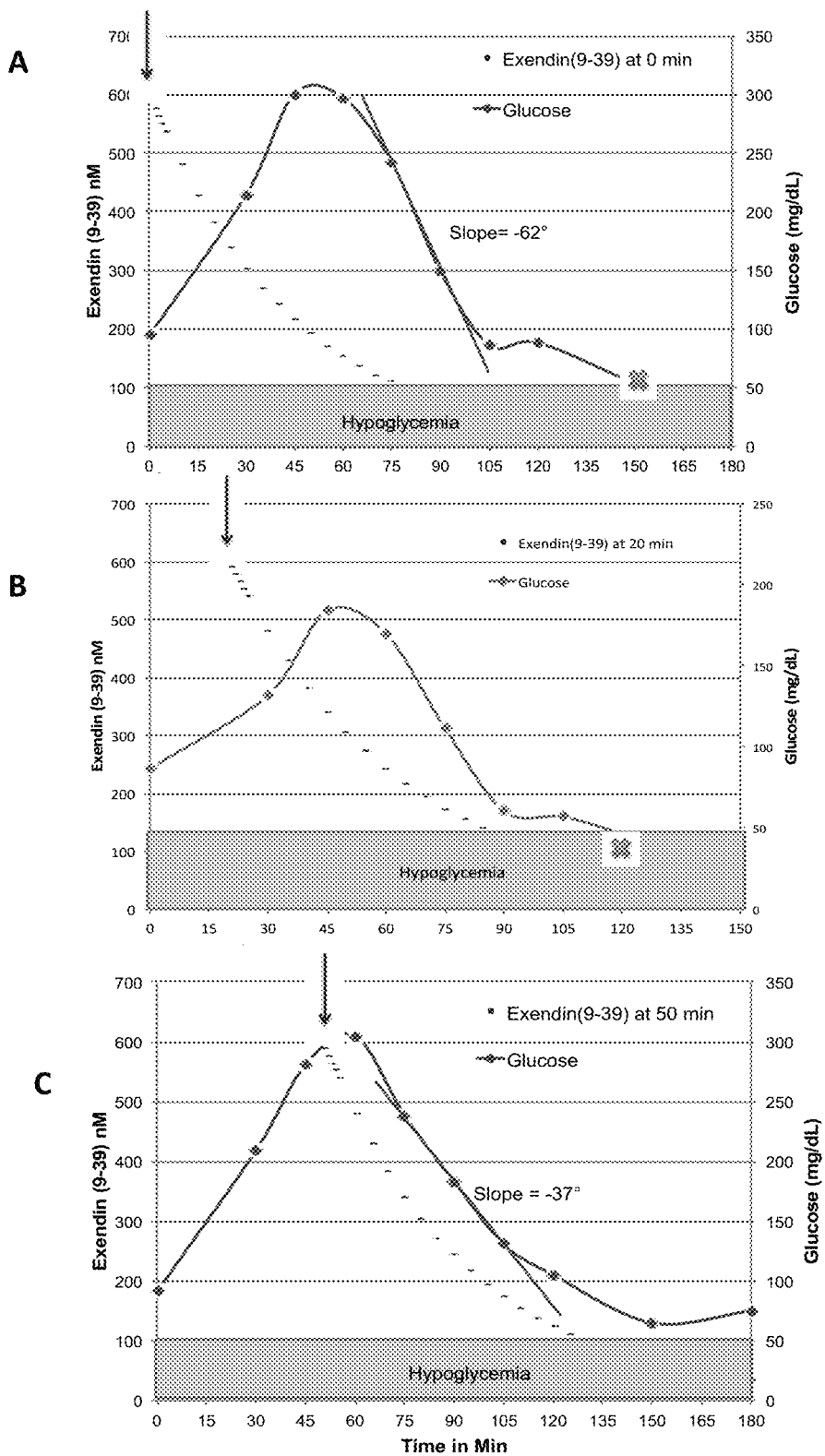
FIG. 4A-C

TREATMENT OF POST-BARIATRIC HYPOGLYCEMIA WITH GLP-1 ANTAGONISTS

CROSS-REFERENCE TO RELATED APPLICATIONS

This application is a continuation of U.S. application Ser. No. 16/813,536 filed Mar. 9, 2020, which claims priority to U.S. application Ser. No. 15/576,646, filed Nov. 22, 2017, which is the National Stage of International Application No. PCT/US2016/033836, filed May 23, 2016, which claims priority to U.S. Provisional Application No. 62/329,850, filed Apr. 29, 2016, U.S. Provisional Application No. 62/254,175, filed Nov. 11, 2015, and U.S. Provisional Application No. 62/165,743, filed on May 22, 2015, the contents of each of which are incorporated by reference in their entireties for all purposes.

STATEMENT AS TO RIGHTS TO INVENTIONS MADE UNDER FEDERALLY SPONSORED RESEARCH AND DEVELOPMENT

This invention was made with Government support under contract TR001085 awarded by the National Institutes of Health. The government has certain rights in the invention.

FIELD OF THE INVENTION

The present invention provides methods and compositions for the treatment of hypoglycemia, particularly post-bariatric hyperinsulinemia, and more generally hyperinsulinemic hypoglycemia of any origin, and the prevention of associated acute symptoms and chronic outcomes in which a glucagon-like peptide-1 receptor antagonist (GLP1RA) is formulated for administration and administered in a therapeutically effective dose, often by route of subcutaneous injection, either alone or in combination with an amylinomimetic or other anti-gastric emptying agent. In various embodiments, the patient receiving therapy has had bariatric surgery, a metabolic procedure, or a gastrointestinal surgery, and the hyperinsulinemic hypoglycemia ("hyperinsulinemia" or more generally hypoglycemia) suffered by the patient is believed by his or her physician to be due to complications of that surgery or some other procedure or condition likely to result in similar disease pathology. The invention therefore relates to the fields of biology, chemistry, medicinal chemistry, medicine, molecular biology, and pharmacology.

BACKGROUND OF THE INVENTION

Roux-en-Y gastric bypass (RYGB), widely performed for medically complicated obesity, cures type 2 diabetes in 85% of cases. The physiologic mechanisms mediating diabetes resolution is controversial, but the reduction in glucose excursions prior to weight loss has led to postulates that the incretin hormone, glucagon-like peptide-1 (GLP-1), may play an important role. GLP-1 stimulates the secretion of insulin by pancreatic beta cells and is responsible for the "incretin" effect: incretin hormones enhance the glucose-dependent secretion of insulin, such that pancreatic beta cells will secrete more insulin after an oral glucose load than after an isoglycemic IV glucose load. Enhanced secretion of GLP-1 after RYGB, and a resultant elevation in insulin secretion, may play a primary role in the resolution of diabetes after RYGB. Indeed GLP-1 analogs have been developed to treat diabetes.

However, as the use of bariatric surgical procedures continues to increase worldwide, a severe complication—hyperinsulinemic hypoglycemia—is increasingly reported. Present in 1-6% of RYGB patients, this disorder leads to severe symptomatic hypoglycemia that plagues patients often multiple times daily, with glucose concentrations low enough (20-40 mg/dL) to cause seizures, altered mental status, loss of consciousness, cognitive dysfunction, disability, and death. Quality of life is severely diminished, and many patients cannot care for themselves or others, work, drive, or be left alone. There is no effective treatment and severe cases have been managed with near-total to total pancreatectomy, which results in insulin-dependent diabetes and is associated with a 6% surgical mortality risk.

Given the severity of this chronic disorder with unmet clinical need, an effective therapeutic treatment is urgently needed. It would thus be useful to provide a method for the treatment of hyperinsulinemic hypoglycemia post bariatric surgery and prevention of its acute symptoms and chronic outcomes, and a pharmaceutical composition for such therapeutic.

SUMMARY OF THE INVENTION

While the present invention provides a variety of methods and materials for treatment and prevention of hyperinsulinemic hypoglycemia, one aspect of this invention relates to the pharmaceutical compositions and methods involving subcutaneous delivery of a GLP-1 receptor antagonist ("GLP-1RA") in doses therapeutically effective for this indication. In some instances, exendin(9-39) is delivered subcutaneously as a GLP-1RA for this indication. In many embodiments, subcutaneous GLP-1RA formulations, including formulations of exendin(9-39), are provided as immediate release preparations or as extended/slow release preparations, and are conveniently packaged, for example, in the form of the dual-chamber pen device provided by the invention, or an alternate vial and syringe combination provided by the invention for patients to self-administer, or their care providers to administer, therapeutically effective amounts of the GLP-1RA.

For exendin(9-39) and GLP-1RAs of similar activity and in similar formulations to achieve similar pharmacokinetics as described herein, therapeutically effective doses range from 2-100 mg. In some embodiments, exendin(9-39) is formulated and administered in an injectable pen device or via a vial/syringe combination that may be pre-programmed or marked to deliver a fixed dosage amount ranging from 2-100 mg, 10-75 mg, 20-50 mg, 20-40 mg, 2-10 mg, 2.5-10 mg, or 2.5-7.5 mg, depending upon the needs and physical attributes of the patient. In some embodiments, adult patients (60-100 kg or more) will receive therapeutic benefit from a single dose in the range of 10-75 mg, with some achieving full therapeutic effect with 20-40 mg. Each dose will be administered in a total volume ranging from 0.25-2 ml injectate. In some embodiments, adult patients (and some adolescents and minors) will benefit from doses as low as 5 mg or from 2.5 mg to 5 mg, and typical doses will often range in the 2.5 mg to 10 mg, 2.5 mg to 7.5 mg, or 5 mg to 30 mg dose. As noted, most patients will self-administer this dose at least once a day, and often twice a day. Some patients will administer this dose with each meal, or before a particular meal, including, for example a certain time, e.g., 15 minutes to two hours, e.g. one hour, before a meal, or a certain time after a meal.

In one embodiment, the patient self-administers a dose of exendin(9-39) in the range of 5 mg to 30 mg or 2.5 mg to 10 mg in an immediate release or extended release formulation. In one embodiment, this dose is administered BID using an immediate release formulation, with the first dose in the morning, typically before the first meal, e.g. at least 60 minutes before, and the second about twelve hours later. In another embodiment, this dose is administered qD in an extended release formulation that is dosed either in the morning, as above, or in the evening, e.g., before or after the last meal of the day, including, e.g. before retiring. For these various embodiments, the invention provides immediate release formulations of exendin(9-39) and formulations similar to that of Byetta® (Amylin; AstraZeneca), a subcutaneously administered form of exenatide. In other embodiments, the formulation is an extended release formulation of the invention suitable for once-a-week subcutaneous administration that is similar to the Bydureon® (Amylin; AstraZeneca) formulation that provides for once-a-week dosing of exenatide. In other embodiments, the formulation is an extended release formulation of the invention suitable for once-a-day subcutaneous administration that is similar to the Victoza® (Novo Nordisk) formulation that provides for a once-a-day dosing of the GLP-1 agonist liraglutide.

In various embodiments, the invention provides immediate release and delayed release formulations of exendin(9-39) and methods for their delivery by subcutaneous administration to post-bariatric surgery patients suffering from hyperinsulinemia (hypoglycemia). In one embodiment of the invention, the patient self-administers (or is wearing a device programmed to administer) the exendin(9-39) in a dose ranging from 4-40 mg, although many patients will receive therapeutic benefit by a dose ranging from 10-25 mg. Dosing will typically be qD or BID, with qD administration typically utilizing a delayed or extended release formulation of the invention. The first dose may be administered in the evening, such that it provides protection during breakfast the following day, with subsequent doses following the next evening and each evening thereafter for qD administration or the following morning and about twelve hours later for BID administration. In one embodiment, a therapeutically effective amount of exendin(9-39) is administered via subcutaneous injection to provide treatment benefit similar to that achieved by continuous IV infusion of exendin(9-39), which effectively reverses postprandial hyperinsulinemic hypoglycemia and associated symptoms. In one embodiment, a patient receives an intravenous (IV) infusion of a GLP1A, followed by administration of a therapeutically effective dose of a GLP1A by subcutaneous injection, or by another route of administration described herein. While continuous IV infusion can be used in the in-patient hospital setting for chronic or acute severe hypoglycemia, this may not be a practical or realistic outpatient method of treatment. The pharmacokinetic properties of intravenously administered exendin(9-39) (for example, a half-life (T½) of 33.5 minutes, a volume of distribution ($V_d$) of 111 ml/kg, and a drug clearance (CL) of 2.3 ml·kg$^{-1}$·min$^{-1}$), however, are such that one of ordinary skill in the art would conclude that continuous IV infusion of exendin(9-39) would be required in order to achieve a therapeutic response.

In accordance with the methods of the invention, however, other routes and forms of administration may be employed with significant benefit both to patient and physician. For example, a single IV bolus dose of the exendin (9-39) administered as described herein can effectively prevent hypoglycemia despite its half-life of 33.5 minutes (see FIGS. 4A-D and Example 2). While this method provides some treatment benefit, if the administration is not timed to coincide precisely with the GLP-1 peak plasma concentrations, IV bolus administration can fail to prevent hypoglycemia.

More importantly, for most patients, subcutaneous injection of exendin(9-39) as described herein can provide even more efficacious results. The present invention can be practiced with an immediate release formulation of exendin(9-39) that, when used in accordance with the invention, will effectively prevent hypoglycemia in most patients. Furthermore, for this and other formulations, there is no requirement, at least for the vast majority of patients, to time the administration to peak GLP-1 plasma concentration or any other biomarker.

Many patients, however, will achieve good control of their glucose and much prefer the convenience of one of the extended release formulations of the invention for subcutaneous injection, e.g., a once-a-week formulation, and some patients can benefit from the oral, inhaled, or nasal formulations provided.

In addition, in some embodiments of the method, some patients will enjoy enhanced therapeutic benefit from the co-administration of an amylinomimetic or any agent that has the effect of delaying gastric emptying. Consequently, the present invention also provides for combination therapies in which a GLP-1A, such as exendin(9-39), is coadministered with an agent that delays gastric emptying, such as an amylin peptide (e.g. Symlin), to improve the treatment of hyperinsulinemic hypoglycemia, or with another agent that delays gastric emptying, such as an aluminum hydroxide antacid, any H2 Receptor Antagonist (e.g. Ranitidine, Cimetidine, or Famotidine), or any Proton Pump Inhibitor, (e.g. Omeprazole, Lansoprazole, or Pantoprazole), or any combination of any of the foregoing. The pharmaceutical compositions of the invention have use for treatment and prevention of hyperinsulinemic hypoglycemia and its associated symptoms and outcomes in patients with hyperinsulinemic hypoglycemia post bariatric surgery and post gastrointestinal surgery. In addition, because hypoglycemia can be averted in a GLP-1-dependent manner, the compositions of the invention are also useful as an immediate antidote for any over-exposure to GLP-1 or similarly acting GLP-1 analogue, such as in instances of postprandial hypoglycemia that do not occur in the postbariatric or post gastrointestinal surgery setting, and in instances of acute overdosing of a GLP-1 agonist. GLP-1 agonist drugs are well known in the art and include exenatide, liraglutide, lixisenatide, albiglutide, and dulaglutide.

In these and other embodiments, the invention provides for the prevention and treatment of associated acute and chronic symptoms and outcomes in susceptible patients. Treatment in accordance with the invention of patients in need of therapy will improve patient quality of life both in the short- and long-term, will reduce overall patient morbidity, and may prevent premature death and/or extend life-expectancy. The present invention is believed to be the first safe and effective treatment for hyperinsulinemic hypoglycemia.

BRIEF DESCRIPTION OF THE DRAWINGS

FIG. 2A-C. Average plasma GLP-1 (A), GIP (B), and glucagon (C) response to a 75 gram OGTT in subjects with hyperinsulinemic hypoglycemia receiving primed continuous IV infusion of exendin(9-39) of 500 pmol/kg/min over 180 minutes versus placebo (normal saline) infusion, as described in Example 1. Solid line: placebo infusion; dashed line: exendin(9-39) infusion.

FIG. 3. Individual and average symptomatic responses to a 75 gram OGTT in 8 patients with hyperinsulinemic hypoglycemia receiving a primed continuous IV infusion of exendin(9-39) versus placebo, as described in Example 1. Overall Symptom Score, Glucose Rise, and Glucose Fall Scores are presented. Continuous IV infusion of exendin(9-39) at 500 pmol/kg/min over 180 minutes substantially improved symptoms of hypoglycemia, as demonstrated by the reduced Overall Symptom and Glucose Fall scores.

FIG. 4A-D. Plasma glucose responses to IV bolus doses of 7,500 pmol/kg of exendin(9-39) administered to a subject with hyperinsulinemic hypoglycemia at different time points relative to the timing of administration of glucola in an OGTT. Specifically, the exendin(9-39) IV bolus was administered at: (A) T=0 minutes, (B) T=20 minutes, or (C) T=50 minutes. For (A)-(C), glucose levels measured at specific timepoints as described in Example 2 are shown by a solid line. For (A)-(D), the projected exendin(9-39) PK curve after administration of the IV bolus of 7,500 pmol/kg is shown by a dotted line. Dosing at 0 minutes (A) or 20 minutes (B) did not prevent hypoglycemia, whereas dosing at 50 minutes (C) did prevent hypoglycemia. (D) The GLP-1 peak for the subject in (C) occurred at 60 minutes, suggesting that timing the administration of the IV bolus to the GLP-1 plasma peak was necessary to prevent hypoglycemia.

BRIEF DESCRIPTION OF THE TABLES

Figure 1:
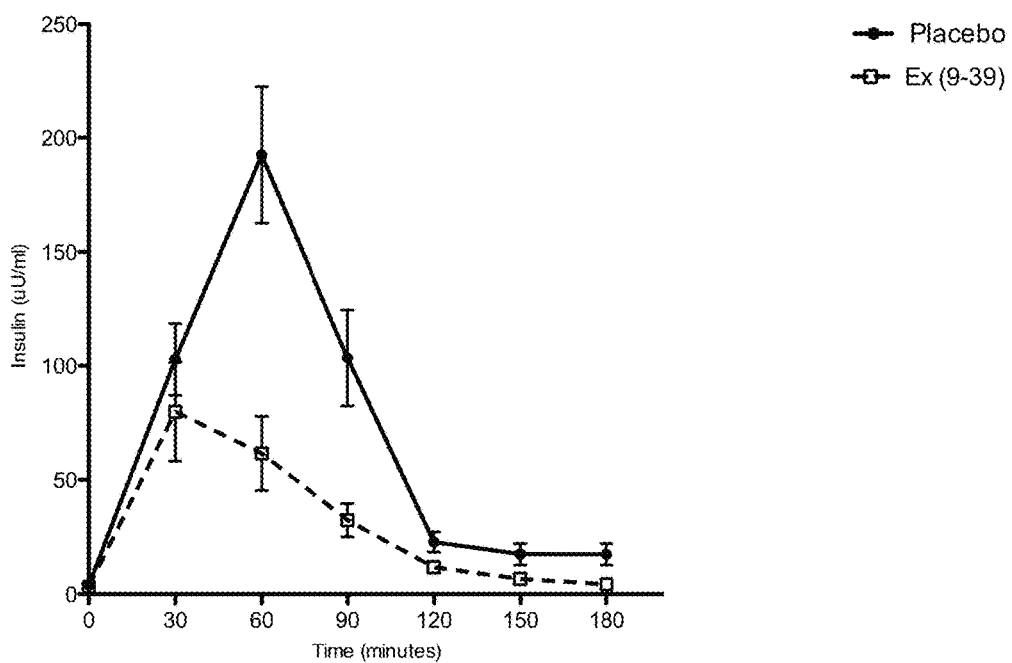
FIG. 1A-B. Average plasma glucose (A) and insulin (B) responses to a 75 gram oral glucose tolerance test (OGTT) in subjects with hyperinsulinemic hypoglycemia during a randomized blinded cross-over study in which a primed continuous intravenous (IV) infusion of exendin(9-39) (at 500 pmol/kg/min over 180 minutes) or placebo (normal saline) was administered, as described in Example 1. Solid line: placebo infusion; dashed line: exendin(9-39) infusion.
Figure 1:
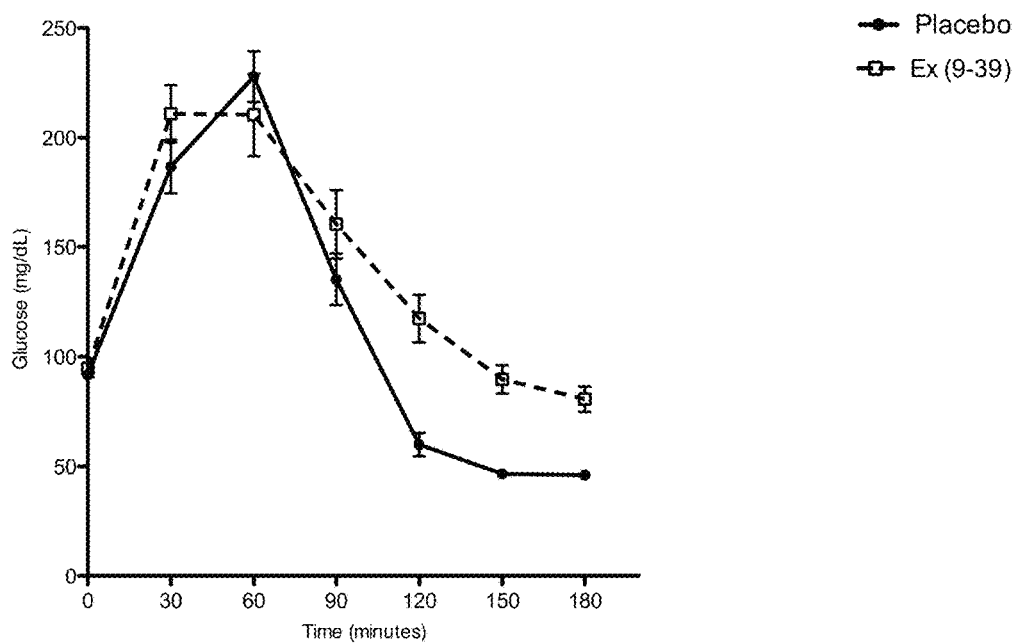

Table 1: Metabolic responses to a 75 gram oral glucose tolerance test (OGTT) during primed continuous IV infusion of exendin(9-39) in eight post-RYGB patients with hyperinsulinemic hypoglycemia (HH). Metabolic responses of eight BMI, age, and sex matched non-surgical controls are presented for comparison. AUC values were calculated by the trapezoidal rule utilizing the last value carried forward to account for prematurely discontinued OGTTs in cases of hypoglycemia, which occurred solely during placebo infusion.

Table 2: Mean plasma GLP-1, GIP and glucagon response to a 75 gram oral glucose tolerance test (OGTT) in eight patients with hyperinsulinemic hypoglycemia (HH) during a primed continuous IV infusion of exendin(9-39) of 500 pmol/kg/min over 180 minutes vs. during placebo (normal saline) infusion.

Table 3: Subject metabolic and symptomatic response to a single subcutaneous (SC) injection of 10-30 mg of exendin (9-39), denoted as SC Ex(9-39), continuous IV infusion of exendin(9-39 (IV Ex(9-39)), or placebo during a 75 gram OGTT. This table demonstrates that clinical efficacy during this SAD subcutaneous injection study was comparable to that achieved during continuous IV infusion of exendin(9-39), as measured by the plasma glucose nadir, AUC glucose, and the Symptom Fall Score.

Table 4: PK/PD response to increasing doses/increasing concentrations. As described in Example 3, subjects 2-5 each received a subcutaneous injection of exendin(9-39) in doses ranging from 37,500-112,500 pmol/kg (approximately 10-30 mg) each in a volume of 0.7 ml, resulting in dose concentrations of approximately 15-40 mg/ml. Shown here are subject PK/PD responses to each dose. Injectate concentrations of approximately 15 mg/ml resulted in the greatest pharmacodynamic response, as defined by nadir postprandial glucose and AUC glucose, and greatest pharmacokinetic response, as defined by Cmax and DN Cmax. Thus a relatively dilute dose may be preferred for BID dosing, and a more concentrated formulation may be preferred for less frequent dosing or a more sustained exposure. The 75,000 pmol/kg dose (17 mg) with a concentration of about 24 mg/ml resulted in a favorable sustained/slow release pharmacokinetic response, with a half-life of 9.14 hours, and a Cmax that was 70 or more ng/ml. Thus a relatively concentrated dose may be used advantageously for qD or BID dosing not tied to meals.

Table 5: PK/PD response to increasing dose with constant injectate concentration. As described in Example 3, four subjects received subcutaneous injections of 37,500-112, 500 pmol/kg exendin(9-39) in equivalent concentrations (approximately 13-16 mg/ml), as this concentration was found to result in a favorable immediate release formulation of the invention. Results shown demonstrate an increasingly favorable PK response with increasing dose, as defined by Cmax and $T_{1/2}$.

Table 6: PK/PD response in four subjects dosed with varying doses of subcutaneously administered BID exendin (9-39) in a 3-day clinical trial as described in Example 4.

DETAILED DESCRIPTION OF THE INVENTION

1. Introduction

Post-bariatric hyperinsulinemic hypoglycemia is a disorder that is characterized by low blood sugar and elevated insulin levels 1-3 hours after meals. The disorder manifests as neuroglycopenic symptoms (such as confusion, loss of focus, fatigue, ataxia, paralysis, seizures, or loss of consciousness), vasomotor symptoms (such as sweating and shakiness), and/or adrengeric symptoms (such as heart palpitations). Although the pathogenesis of post-bariatric hyperinsulinemia is not entirely understood, several mechanisms have been proposed, including increased section of insulinotropic incretin gut hormones from the hindgut, expansion in β-cell mass, enhanced β-cell sensitivity, increased insulin sensitivity, decreased insulin clearance, reduced ability to mount a counterregulatory glucagon response, and absence of a prodiabetogenic/decretin foregut factor.

As described in Example 1, administration of a Glucagon-like Peptide-1 (GLP-1) receptor antagonist, exendin(9-39), by primed continuous intravenous (IV) infusion of exendin (9-39) effectively reversed hyperinsulinemic hypoglycemia and associated symptoms in patients having hyperinsulinemic hypoglycemia. In this trial patients received a total dose about 23-36 mg exendin(9-39), with the drug quantity varying with patient weight. (Also see Salehi et al., 2014, "Blockade of Glucagon-like Peptide 1 Receptor Corrects Postprandial Hypoglycemia After Gastric Bypass," *Gastroenterology* 146:669-680.) However, different pharmacokinetic profiles would be expected, and are observed, for a subcutaneously administered GLP-1 antagonist such as exendin(9-39) as compared to intravenous administration. See Example 3. Accordingly, one of ordinary skill in the art would have expected that a significantly higher dose of a GLP-1 antagonist such as exendin(9-39) would be needed for subcutaneous administration, as compared to intravenous administration, in order for exendin(9-39), to be effective in reversing hyperinsulinemic hypoglycemia.

It has been surprisingly shown that subcutaneous administration of exendin(9-39) can effectively prevent hypoglycemia in patients having post-bariatric hyperinsulinemic hypoglycemia, even at doses lower than the doses administered in continuous primed IV infusion as described in Example 1. See, Example 3 and Example 4. Thus, in one aspect, the present invention relates to pharmaceutical compositions and methods for subcutaneously administering a GLP-1 antagonist at a therapeutically effective dose for the treatment and prevention of hyperinsulinemic hypoglycemia.

It will be recognized by physicians and pharmacologists that the present invention represents a significant advance in the field of surgical intervention for weight loss and/or metabolic control. This is especially important, because those post-bariatric patients currently suffering hypoglycemic excursions have no effective therapy and are sometimes critically ill. The intractable nature of the problem has been highlighted by those patients with disease so debilitating they reversed the surgery, or underwent other highly morbid procedures, such as partial pancreatectomy, only to learn the condition persists. The present invention is a significant advance for this reason alone: those patients now have a therapeutic intervention that can largely protect them should they suffer from post-bariatric hyperinsulinemia.

2. Definitions

The terminology used herein is for the purpose of describing particular embodiments only, and is not intended to be limiting. Unless defined otherwise, all technical and scientific terms used herein have the same meaning as commonly understood by one of ordinary skill in the art to which this invention pertains. In some cases, terms with commonly understood meanings are defined herein for clarity and/or for ready reference, and the inclusion of such definitions herein should not be construed as representing a substantial difference over the definition of the term as generally understood in the art.

Although any methods and materials similar or equivalent to those described herein can be used in the practice or testing of the present invention, the preferred methods and materials are now described. All technical and patent publications cited herein are incorporated herein by reference in their entirety.

All numerical designations, e.g., pH, temperature, time, concentration, and molecular weight, including ranges, are approximations which are varied (+) or (−) by increments of 0.1 or 1.0, as appropriate. It is to be understood, although not always explicitly stated, that all numerical designations are preceded by the term "about." References to ranges include the end-points unless indicated otherwise. For example, administration of a dose of a GLP-1 antagonist in the range 10-75 mg includes administration of 10 mg or 75 mg.

The singular forms "a," "an," and "the" include plural referents unless the context clearly dictates otherwise. Thus, for example, reference to "a compound" includes a plurality of compounds.

The term "comprising" is intended to mean that the compositions and methods include the recited elements, but not excluding others. "Consisting essentially of" shall mean excluding other elements that would materially affect the basic and novel characteristics of the claimed invention. "Consisting of" shall mean excluding any element, step, or ingredient not specified in the claim. Embodiments defined by each of these transition terms are within the scope of this invention.

The terms "administer," "administering," and "administration," as used herein, refer to introducing a compound (e.g., exendin(9-39) or composition into a subject, such as a human. As used herein, the terms encompass both direct administration (e.g., administration to a subject by a medical professional or other caregiver, or by self-administration, or by programming an automatic device to deliver a GLP-1 antagonist on a schedule) and indirect administration (e.g., the act of prescribing a compound or composition to a subject).

The terms "treatment," "treating," and "treat," as used herein in reference to administering a GLP-1 antagonist to treat hyperinsulinemic hypoglycemia covers any treatment of a disease in a human subject, and includes: (a) reducing the risk, frequency or severity of hypoglycemic episodes in patients with a history of hyperinsulinemic hypoglycemia, (b) reducing the risk of occurrence of hypoglycemia in a subject determined to be predisposed to the disease, such as a person who has received post-bariatric surgery, but not yet diagnosed as having the disease, (c) impeding the development of the disease; and/or (d) relieving the disease, i.e., causing regression of the disease and/or relieving one or more disease symptoms.

As used herein, the term "injectate" refers to a GLP1A-containing (e.g., an exendin(9-39)-containing) composition that is delivered to a patient at a morning or evening administration. A morning or evening injectate is typically administered as a single injection (e.g., injection of a 0.7 ml volume). However an injectate can be delivered using more than one (e.g., two) injections, as may be done when the injectate volume is greater than comfortably tolerated as a single injection.

As used herein, "/kg" (e.g., 7,500 pmol/kg") means "per kilogram patient body weight."

3. Methods and Compositions for the Treatment of Hyperinsulinemic Hypoglycemia

In one aspect, the present invention provides methods and compositions for the treatment of hyperinsulinemic hypoglycemia by administration of a therapeutically effective dose of a GLP-1 antagonist.

3.1 GLP-1 Antagonists

In one aspect, the present invention provides pharmaceutical compositions and methods involving administration of a GLP-1 receptor antagonist ("GLP-1RA"), also referred to as GLP-1 antagonist ("GLP1A"), and so used interchangeably herein.

In various embodiments, the GLP1A is exendin(9-39). As used herein, the term "exendin(9-39)" or "Ex(9-39)" or "Ex9" refers to a 31 amino acid peptide with an empirical formula of $C_{149}H_{234}N_{40}O_{47}S$ and a molecular weight of 3369.8 Daltons. The amino acid sequence for exendin(9-39) is shown as follows: H-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-$NH_2$. Exendin (9-39) comprises residues 9-39 of the GLP-1 receptor agonist exendin-4 and is a GLP-1 receptor antagonist. See, Montrose-Rafizadeh et al., *Journal of Biological Chemistry*, 272:21201-21206 (1997). As used herein, the term "exendin (9-39)" encompasses pharmaceutically acceptable salts of exendin(9-39), including but not limited to sulfate, hydrochloride, phosphate, sulfamate, acetate, citrate, lactate, tartrate, methanesulfonate, ethanesulfonate, benzenesulfonate, p-toluenesulfonate, cyclohexylsulfamate and quinate salts. In some embodiments, exendin(9-39) is in the form of exendin(9-39) acetate or exendin(9-39) trifluoroacetate. Where not otherwise specified herein, exendin(9-39) acetate is used (obtained from Bachem (Clinalfa, Läufelfingen, Switzerland)).

In various embodiments, the GLP1A is a homologue, an analogue, or a variant of exendin(9-39). In various embodiments, the GLP1A is any exendin(9-39) peptide known in the art. In various embodiments, the GLP1A is a derivative of an exendin-4 peptide other than exendin(9-39) or a derivative of a small molecule allosteric ligand (e.g. any derivative of "compound 2" [6,7-dichloro-2-methylsulfonyl-3-tert-butylaminoquinoxaline, a GLP1 receptor agonist] that only binds one of the two allosteric binding sites on the GLP1 receptor, or a similar derivative of BETP [4-(3-benzyloxy)phenyl)-2-ethylsulfinyl-6-(trifluoromethyl)pyrimidine]). In various embodiments, the GLP1A is a derivative of an endogenous GLP-1 peptide (e.g. a derivative of GLP-1(1-36)NH2, GLP-1(1-37), GLP-1(7-36)NH2, GLP-1 (7-37), or of oxyntomodulin). Derivatives of particular interest for these embodiments are those that have structure changes or substitutions in any of the foregoing GLP-1 peptides, particularly those with changes or substitutions at one or more of GLU16, VAL19, and ARG 20.

In all of these embodiments, the GLP1A acts not as an agonist but as an antagonist of the GLP-1 receptor. Some of these GLP1A, like exendin(9-39) may also competitively antagonize the GIP receptor, although such activity is not believed to be required for efficacy. While the invention is not to be limited in any manner by virtue of a putative mechanism of action, molecules reported to be antagonists as a result of binding only one of the two ligand binding sites of GLP-1 receptor or otherwise having altered ligand-binding ability or affinity (e.g. at sites 149 or 333 on the GLP-1 receptor) resulting in attenuated or inhibited GLP-1 receptor activation are suitable for use in the methods of the invention. In various embodiments, the GLP1A is resistant to proteolytic cleavage or to degradation by dipeptidyl peptidase-IV (DPPIV) or other dipeptidyl peptidase known in the art.

The present invention provides novel exendin(9-39) conjugates and new formulations of exendin(9-39) conjugates, in which the exendin(9-39) has been chemically modified. For example, the present invention provides acylated exendin(9-39), which can be prepared, for example and without limitation, with palmitic, lauric, lithocholic acid or a stearic diacid to prevent DPPIV degradation. Alternatively, the present invention provides conjugates in which the peptide is conjugated to an Fc protein to minimize detection by the immune system, resulting in a longer acting drug, at least for some patients. As another example, the present invention provides PEGylated exendin(9-39), a conjugate with a polyethylene glycol (PEG) so as to maximize plasma circulation time while minimizing loss of activity.

The methods, formulations, and examples discussed above are equally applicable to any GLP-1RAs having similar biochemical structure to exendin(9-39), including but not limited to other exendin analogues, pegylated versions, acylated versions, and amino acid variants thereof.

3.2 Patient Population

In some embodiments, a patient to be treated according to the methods described herein is a patient having hyperinsulinemic hypoglycemia (HH). In certain embodiments, the patient having hyperinsulinemic hypoglycemia has previously had bariatric surgery (e.g., Roux-en-Y Gastric Bypass) and/or a related metabolic procedure. In certain embodiments, the patient has previously had bariatric surgery (e.g., Roux-en-Y Gastric Bypass) and/or a related metabolic procedure and is at risk for developing hyperinsulinemic hypoglycemia.

Patients with hyperinsulinemic hypoglycemia may be identified by any suitable method. In some embodiments, hyperinsulinemic hypoglycemia is diagnosed by the presence of Whipple's triad, which has the following criteria: (1) the occurrence of hypoglycemic symptoms; (2) documented low plasma glucose level at the type of the symptoms; and (3) resolution of the symptoms after plasma glucose is raised. In some embodiments, hyperinsulinemic hypoglycemia is defined by the occurrence of capillary glucose ≤50 mg/dL at least once per month by patient report or medical record. In some embodiments, hyperinsulinemic hypoglycemia is defined by a plasma glucose concentration of ≤55 mg/dL during an oral glucose tolerance test in association with inappropriately elevated plasma insulin (≥3 uU/mL) or c-peptide (>0.3 mg/dL) when glucose was ≤55 mg/dL. In some embodiments, hyperinsulinemic hypoglycemia is defined by a plasma glucose concentration of ≤60 mg/dL during an oral glucose tolerance test or meal tolerance test in association with inappropriately elevated plasma insulin (≥3 uU/mL) or c-peptide (>0.3 mg/dL) when glucose was ≤60 mg/dL.

"Hyperinsulinemic hypoglycemia," as used herein, encompasses the conditions dumping syndrome, nesideoblastosis, noninsulinoma pancreatogenous hypoglycemia syndrome (NIPHS), and/or post-prandial reactive hypoglycemia. Hyperinsulinemic hypoglycemia may result from a gastric or bariatric procedure, such as a Roux-en-Y gastric bypass (RYGB), or may have a congenital, acquired, or induced origin.

Those skilled in the art will appreciate that hyperinsulinemic hypoglycemia is occasionally referred to as dumping syndrome, nesideoblastosis, noninsulinoma pancreatogenous hypoglycemia syndrome (NPHS), and/or post-prandial reactive hypoglycemia, and so may be referred to herein as "hyperinsulinemic hypoglycemia." Those skilled in the art will further appreciate that hyperinsulinemic hypoglycemia may result from a gastric or bariatric procedure, or may have a congenital, acquired, or induced origin, and the methods and compositions may be used for therapeutic benefit with patients from any of these groups.

In one embodiment, the patient treated has previously had a bariatric and/or related metabolic procedure (of any type, including but not limited to Roux-en-Y Gastric Bypass, Vertical Sleeve Gastrectomy, placement of an endosleeve device, such as the EndoBarrier Gastrointestinal Liner System, also called an "endoluminal liner," duodenal mucosal resurfacing, also referred to as duodenal ablation, partial bypass of the duodenum, involving duodeno-ileal or duodeno-jejunal anastomosis, vagal nerve blockade, and/or pyloroplasty) and so may be referred to herein as "post bariatric surgery" even though often bariatric surgery may be thought of exclusively as weight loss surgery. Such procedures may be intended for weight loss or metabolic benefit (such as resolution of diabetes), or both, and typically involve any of the foregoing: partially or completely bypassing the duodenum and/or decreasing nutrient exposure to the duodenum, increasing the rapidity of nutrient transit to the lower part of the intestines (often specifically the ileum), and/or otherwise increasing ileal nutrient exposure. All such weight loss or metabolic procedures, referred to herein as "bariatric procedures" may enhance secretion of GLP-1 from the distal small intestine, especially the ileum, leading to elevated insulin secretion, and in some patients hypoglycemia. The methods and formulations of the invention are applicable to any of these conditions and conditions of similar biologic origin or cause. The patient may be referred to as a "post bariatric surgery" patient. or "post-RYGB."

In another embodiment, the patient has previously had a related metabolic procedure. As but one example, in one embodiment, the patient treated has previously had a non-bariatric surgical procedure involving the gastrointestinal system (including but not limited to esophagectomy, for example for treatment of esophageal cancer, Nissen Fundoplication, for example gastroesophageal reflux, or gastrectomy, for example for treatment of gastric cancer) and so may be referred to herein as "post gastrointestinal surgery."

In another embodiment, the patient treated is prediabetic and/or insulin resistant and may benefit from prevention of pancreatic hyperstimulation from oral carbohydrate ingestion leading to post-prandial hypoglycemia. In another embodiment, a treated patient has a congenital, acquired, or induced form of hyperinsulinemic hypoglycemia.

In a preferred embodiment, however, the patient has had bariatric surgery to aid in weight loss and/or metabolic control and has suffered hypoglycemic excursions requiring urgent medical attention; such patients, as demonstrated conclusively in the examples below, can benefit markedly from treatment with a subcutaneously administered formulation of exendin(9-39) in accordance with the invention.

A typical adult patient with hyperinsulinemic hypoglycemia will present within 10 years of bariatric and/or other gastrointestinal surgery with symptoms of hypoglycemia (e.g. palpitations, tremor, weakness, sweating, confusion, fatigue, blurred vision,) within 5 hours of eating that are associated with a plasma glucose of ≤60 mg/dL and immediate resolution with carbohydrate intake. Many patients experience neuroglycopenic symptoms, such as altered mental status, loss of consciousness, or seizures. Hyperinsulinemia (>2 uU/mL or 13.9 pmol/L) may be documented in the proper laboratory setting at the time of the hypoglycemic event. However, documentation of hyperinsulinemia is not always possible due to logistical challenges associated with this testing (which involves induced hypoglycemia) and concerns over patient safety.

With the increasing incidence of obesity in children and adolescents, and the consequent increasing use of bariatric surgery in the pediatric and adolescent population, hyperinsulinemic hypoglycemia is anticipated in this cohort, and will likely present similarly to the typical adult patient.

Treatment in the typical adult or pediatric patient refers to treatment such that the postprandial plasma glucose nadir is maintained above a concentration of approximately 55 mg/dl (3.0 mmol/liter) based upon the Endocrine Society's Clinical Guidlines (Journal of Clinical Endocrinology & Metabolism, March 2009, 94(3): 709-728), and symptoms of hypoglycemia are reduced. Ideally, normal plasma glucose concentrations are maintained, with those skilled in the art recognizing that in humans a blood glucose level of 65 mg/dl or greater is preferred.

Physicians skilled in the art will recognize from this disclosure that the methods of the invention provide effective treatment, such that a physician following the same prescribing information herein can expect therapeutic benefit will be achieved in patients whom, for treatment of varying underlying conditions, have had surgical manipulation of the gastrointestinal anatomy, and resultant secondary hyperinsulinemic hypoglycemia. Accordingly, to illustrate, the methods of the invention can be used to treat patients such as: 1) a patient whom, due to gastroesophageal reflux, underwent a Nissen Fundoplication procedure, and subsequently developed secondary hyperinsulinemic hypoglycemia; 2) a patient whom, due to a malignant gastric tumor (e.g. adenocarcinoma, gastrointestinal stromal tumor (GIST), or lymphoma), required partitial or complete gastrectomy, with or without any of the foregoing gastric reconstructive procedures: Bilroth I, Bilroth II, RYGB, or Jejunal interposition, developed secondary hyperinsulinemic hypoglycemia; and 3) a patient whom, due to a tumor involving the esophagus or the esophageal gastric junction (EGJ), underwent an esophagectomy, developed secondary hyperinsulinemic hypoglycemia.

Those skilled in the art will further appreciate that patients with hypoglycemia due to acquired or congenital hyperinsulinism ("endogenous hyperinsulinemia" as used herein refers to any such condition not caused by bariatric surgery or GI surgery) should benefit from application of the methods of the invention. Hypoglycemia in these instances can be severe, even life-threatening. Acquired hyperinsulinism may result from insulinomas, autoimmune syndromes, reactive hypoglycemia, adult nesidioblastosis, or gastric dumping syndrome (not due to bariatric or GI surgery). Congenital hyperinsulinism may manifest in the newborn period, or many years later. Accordingly, the methods and formulations of the invention include methods to treat such conditions. In the case of hyperinsulinemia resulting from an insulinoma and congenital hyperinsulinism, a sustained release formulation and/or an immediate release formulation that is administered consistently, such as via a subcutaneous pump, would be employed, with particular emphasis on the prevention of nocturnal hyperinsulinemia.

In similar fashion, hyperinsulinism may further be induced as a medicinal side-effect of, for example, a GLP-1 agonist, such as exenatide, liraglutide, lixisenatide, albiglutide, and dulaglutide. Accordingly, the methods and formulations of the invention include methods to treat overdoses with such drugs.

In some cases, patients with hyperinsulinemic hypoglycemia may also present with cumulative hyperinsulinemic hypoglycemia-associated cognitive impairment. Accordingly, the methods and formulations of the invention include methods to treat or prevent a worsening of cognitive impairment in such patients. Further, in pediatric and adult patients alike, acute and chronic hypoglycemia may be associated with morbidities not only such as cognitive impairment, but also depression, heart palpitations/tachycardia, and potentially other conditions, all of which may be reduced or prevented by preventing hypoglycemia by administration of a GLP1A, such as exendin(9-39), as described herein for post-bariatric patients suffering from hyperinsulinemia/hypoglycemia. In some diabetic patients, severe hypoglycemia has repeatedly been associated with increased total and cardiovascular mortality risk. Thus, prevention of severe hypoglycemia is an important clinical goal for both hospitalized and non-hospitalized patients, and the present invention provides methods and formulations useful for both groups of patients.

3.3 Treatment Parameters

In some embodiments, compositions comprising a therapeutically effective dose of the GLP1A, such as exendin(9-39) or a homologue, analogue, or variant thereof, are administered to a patient in need thereof for the treatment or prevention of hyperinsulinemic hypoglycemia.

3.3.1 Administration Route

In some embodiments, the GLP1A is administered to a patient in need thereof by any suitable route of administration, such as subcutaneously, parenterally, transmusocally, transdermally, intramuscularly, intravenously, intra-dermally, intra-peritonealy, orally, or nasally.

3.3.1.1 Subcutaneous Administration

In some embodiments, the GLP1A, such as exendin(9-39) or a homologue, analogue, or variant thereof, is subcutaneously administered to a patient in need thereof. Sites of injection, include, but not limited to, injection in the thigh, abdomen, upper arm region, or upper buttock region.

While the present invention provides a variety of methods and materials for treatment and prevention of hyperinsulinemic hypoglycemia, one aspect of this invention relates to the pharmaceutical compositions and methods involving subcutaneous delivery of exendin(9-39) in doses therapeutically effective for this indication. In many embodiments, these formulations for subcutaneous administration are formulated as immediate release preparations, and are conveniently packaged, for example, in the form of the dual-chamber pen device provided by the invention, for patients or their care providers to administer therapeutically effective amounts in doses ranging from 2-100 mg.

3.3.1.2 Oral Administration

The present invention also provides GLP1A (e.g., exendin (9-39)) compositions suitable for oral administration. Exendin(9-39) can be formulated for oral delivery with a formulation consisting a protease inhibitor to prevent digestion and an absorption enhancer to facilitate passive diffusion through the intestine wall. The formulation can be filled into a capsule coated with an enteric coating using pH sensitive polymers such as Eudragit® to protect from the acidic pH in the stomach (see, www.oramed.com). In some embodiments an oral formulation of exendin(9-39) of the instant invention combines an absorption-enhancing excipient, such as Eligen® so as to inhibit acid and peptidase-mediated degradation, and improve passive transport across the enterocyte lumen and into the intracellular space.

3.3.1.3 Inhaled Delivery

The present invention also provides methods and compositions in which GLP1A (e.g., exendin(9-39)) is administered by inhalation. Some patients may prefer inhalation over subcutaneous or other forms of delivery, and the present invention provides suitable dry powder inhalation formulations, generally constituting a room temperature stable powder containing exendin(9-39), that can be supplied in capsules and delivered by a device, for example and without limitation, as used for the recently approved inhaled insulin, Afrezza® (see, www.healthline.com).

3.3.2 Administration Dose

As discussed herein, patients with hyperinsulinemic hypoglycemia may be treated with a GLP1A, such as exendin(9-39) or a homologue, analogue, or variant thereof, at a therapeutically effective dose of 2-100 mg, e.g., at a dose ranging from 2-100 mg, 10-75 mg, 20-50 mg, 20-40 mg, 2-10 mg, 2.5-10 mg, or 2.5-7.5 mg, depending upon the needs and physical attributes of the patient. Exemplary doses include 10 mg, 12.5 mg, 15 mg, 17.5 mg, 20 mg, 22.5 mg, 25 mg, 27.5 mg, 30 mg, 35 mg, 40 mg, or 50 mg. In some embodiments, the GLP1A (e.g., exendin(9-39)) is administered at a dose of about 30 mg or lower (e.g., about 10 mg to 30 mg, 10 mg to 25 mg, 10 mg to 20 mg, 15 mg to 20 mg, 10 mg to 17.5 mg, and 10 mg to 15 mg). It will be understood by a person of ordinary skill in the art that the doses described herein can be administered at varying concentrations, including but not limited to the injectate concentrations described in Section 3.3.4.1 below.

In some embodiments, exendin(9-39) is formulated and administered in an injectable pen device that may be pre-programmed to deliver a fixed dosage amount ranging from 2-100 mg, 10-75 mg, 20-50 mg, 20-40 mg, 2-10 mg, 2.5-10 mg, or 2.5-7.5 mg, depending upon the needs and physical attributes of the patient. In some embodiments, adult patients (60-100 kg or more) will receive therapeutic benefit from a single dose in the range of 10-75 mg, with some achieving full therapeutic effect with 20-40 mg. While some or most adult patients will benefit from 10-30 mg, dosing may be initiated at lower doses, for example at 4-7 mg, 1-10 mg, or 2.5-7.5 mg, and maintained if efficacious or alternatively increased stepwise if an enhanced dose response is desired. For especially small patients, for example in the case of children, or infants, a dose as low as 1 mg or less might be employed. In some instances, for example in the case of altered subcutaneous absorption or metabolism, doses outside of this range may be warranted. The foregoing dose ranges also guide dosing of other GLP1A with similar bioactivity, and those of skill in the art appreciate that simple tests can be performed to provide relative bioavailabilities of any two GLP1A, such that the specific information provided here re exendin(9-39) can readily be translated into any other GLP1A the practitioner of the invention elects to employ.

3.3.3 Administration Schedule

In some embodiments, each dose will be administered in a total volume ranging from 0.25-2 ml injectate, with most patients administering an injection volume ranging from 0.5-1.5 ml, i.e., 0.7-1 ml. In many embodiments, patients will self-administer this dose at least once a day (qD), and often twice a day (BID). Some patients will administer this dose with each meal, it being understood that "with each meal" typically refers to a set period (at least 60 minutes, for example) before a meal, e.g., the first or last meal of the day.

In various embodiments, the invention provides immediate release and delayed release formulations of exendin(9-39) and methods for their delivery by subcutaneous administration to post-bariatric surgery patients suffering from hypoglycemia. In one embodiment of the invention, the patient self-administers (or is wearing a device programmed to administer) the exendin(9-39) in a dose ranging from 4-40 mg, 1-10 mg, or 2.5-10 mg, although many patients will receive therapeutic benefit by a dose ranging from 10-25 mg or other dose as described herein. Dosing will typically be qD or BID, with qD administration typically utilizing a delayed or extended release formulation of the invention. The first dose may be administered in the evening, such that it provides protection during breakfast the following day, with subsequent doses following the next evening and each evening thereafter for qD administration or the following morning and about twelve hours later for BID administration.

3.3.3.1 QD and BID Administration

QD and BID administration are well known in the medical arts. In some embodiments BID doses are administered (e.g., self-administered) at about 12 hour intervals (e.g., 7 a.m. and 7 p.m.). However, shorter (e.g., 8 a.m. and 6 p.m.) or longer (e.g., 7 a.m. and 10 p.m.) intervals between BID administrations are possible provided the administrations are at least about 6 hours apart. Preferably the BID administrations are at least about 7 hours, 8 hours, 9 hours, 10 hours or 11 hours apart. Preferably the BID administrations are not more than about 15 hours apart.

In some embodiments QD doses are administered at about 24 hour intervals (e.g., 7 p.m. on successive days). However, shorter (e.g., 7 p.m. and 6 p.m. on successive days) or longer (e.g., 7 p.m. and 10 p.m. on successive days) intervals between QD administrations are possible provided the administrations are at least about 18 hours apart. Preferably the QD administrations are at least about 20 hours, 21 hours, 22 hours, or 23 hours apart. Preferably the QD administrations are not more than about 30 hours apart.

3.3.3.2 Timing of Administration and Relationship to Meals

In one aspect of the invention, an immediate-release formulation of the GLP1A (e.g., exendin(9-39)) is provided as a subcutaneous injectable formulation that is administered prior to the administration of a meal. For example, in some embodiments, the GLP1A is administered within 60-150 minutes (e.g., within 90-120 minutes) prior to morning and evening meals (or before the two main meals of the day, approximately 6 hours or more apart). In one embodiment, the GLP1A is administered BID as morning and evening administration, with patients dosing 60-150 minutes (e.g., 90-120 minutes) prior to the morning and evening meals, so that the peak GLP-1 plasma concentration occurring approximately 30-60 minutes post-meal will be countered by sufficient GLP1A (exendin(9-39)) plasma concentrations at that time to prevent GLP-1 induced hyperinsulinemia.

In another embodiment the BID dosing will be a morning and evening administration with a morning administration after wakening in the morning and evening administration about 12 hours later (in some embodiments, about 12-14 hours or about 12-16 hours later). The morning administration may be before or after breakfast. In this embodiment, the dosing schedule is independent of (i.e., not based on, or dictated by) the timing of meals. In some embodiments the morning administration is within a specified time before and/or after the morning meal (e.g. one hour before and/or one hour after breakfast). In some embodiments the morning administration is before or after the morning meal, as discussed above, and the evening administration is prior to retiring for the night (bedtime) such as between the evening meal and bedtime, or within 1, 2, or 3 hours of bedtime.

In a related embodiment the dosing schedule is semi-independent of mealtimes. For example, in the semi-independent schedule the morning dose is administered on a predetermined schedule relative to the morning meal and the evening dose is scheduled at a time independent of the time of the evening meal (e.g., about 12 hours after the morning administration without regard to the time of the evening meal).

Without intending to be bound by any specific mechanism, it is believed that the schedule, dose, route and formulations of the invention allow the evening administration to provide additional protection at breakfast, and the morning administration to provide protection during the day (e.g., lunch, dinner, or multiple small meals during the day). Advantageously, subcutaneous BID administration of a therapeutically effective dose of GLP1A (e.g., exendin(9-39)) is protective even when not timed to coincide with meals. In contrast, as demonstrated in Example 2, an IV bolus injection of 7,500 pmol/kg exendin(9-39) reversed hypoglycemia only if timed to coincide with the expected peak GLP-1 plasma concentrations.

In some embodiments, the GLP1A is administered QD as an evening administration, with the administration scheduled at a time independent of the time of meals (e.g., independent of the timing of the evening meal). In some embodiments, the evening administration is prior to retiring for the night (bedtime) such as between the evening meal and retiring, or within 1, 2, or 3 hours of retiring. In another embodiment the GLP1A is administered QD as a morning administration, with patients dosing 60-150 minutes (e.g., 90-120 minutes) prior to the morning meal, so that the peak GLP-1 plasma concentration occurring approximately 30-60 minutes post-meal will be countered by sufficient GLP1A (exendin(9-39)) plasma concentrations at that time to prevent GLP-1 induced hyperinsulinemia.

3.3.4 Administration Formulation

3.3.4.1 Injectate Concentration and Volume

Surprisingly, certain pharmacokinetic parameters of subcutaneous GLP1A (e.g., exendin(9-39)) administration can be modified by selecting the concentration of the GLP1A in the injectate. As described in the Examples, subcutaneous injection of a low concentration formulation results in a shorter Tmax (i.e., a faster rise to Cmax) relative to a higher concentration. Subcutaneous injection of a high concentration formulation results in a lower Cmax, a longer Tmax, and longer half-life relative to a lower concentration. See FIG. 7A and Table 4.

Figure 7A:
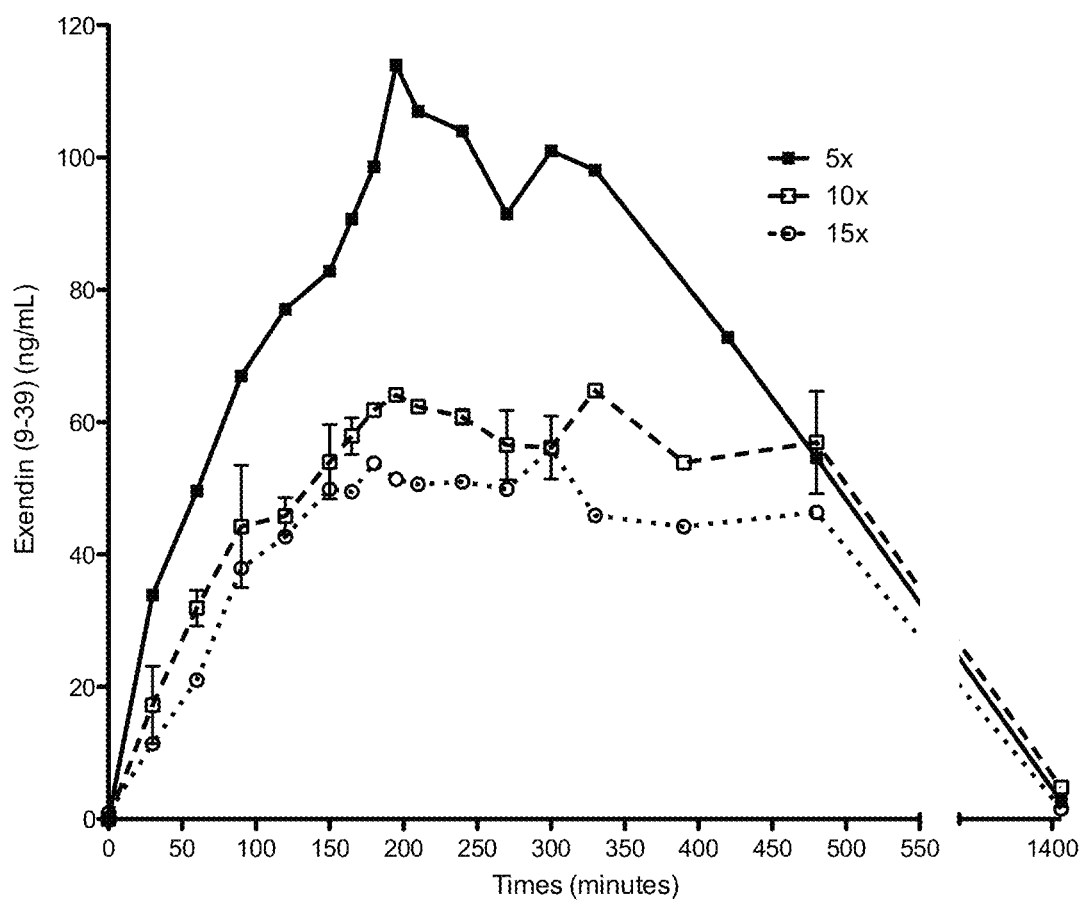
FIG. 7A-B. Plasma exendin(9-39) concentrations following subcutaneous injection of exendin(9-39). (A) Three subjects received a single subcutaneous injection of approximately 10, 20, or 30 mg of exendin(9-39) in a volume of 0.7 ml (5×, 10×, or 15× doses, respectively). (B) Five subjects received doses of approximately 2, 10, 20, or 30 mg (1×, 5×, 10, or 15×, respectively), with each dose administered at a concentration of 15 mg/ml or less; higher doses were administered via more than one injection so as to maintain a relatively dilute concentration.
Figure 7B:
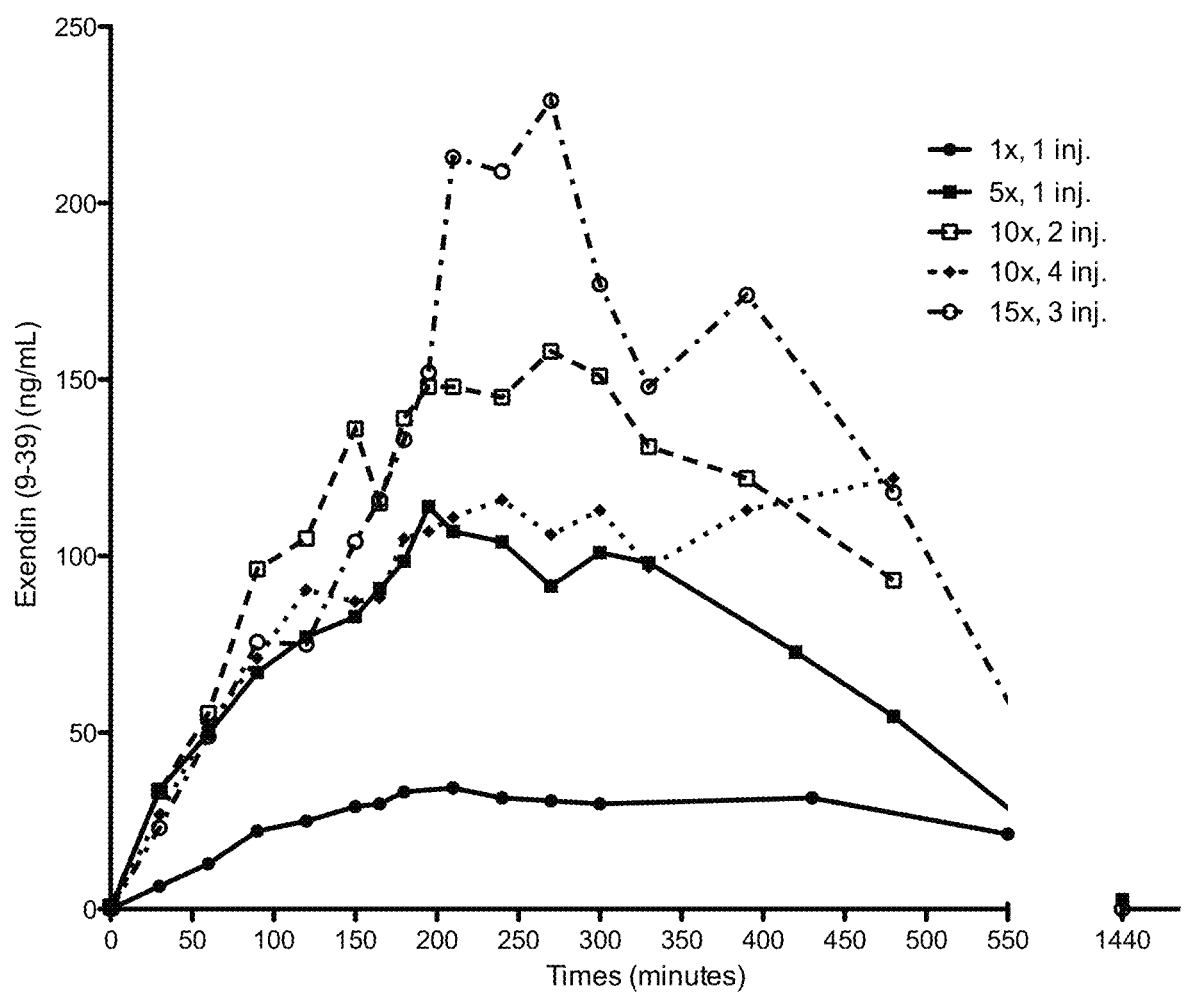

For the purposes of this invention a concentration less than 20 mg/ml is a "low" concentration, e.g., 4-20 mg/ml, preferably about 10-20 mg/ml, and often about 8-16 mg/ml, most often about 13-16 mg/ml, and very often 15 mg/ml. The low concentration formulation results in a pharmacokinetic profile useful for BID administration. As shown in FIG. 7B and Table 5 (Example 3), subcutaneous administration of exendin(9-39) at varying doses but equivalent concentrations of about 13-16 mg/ml resulted in a favorable immediate release formulation with a Cmax greater than a preferred steady state plasma exendin(9-39) concentration of at least 100 ng/ml as measured by liquid chromatograph-mass spectrometry, at 10, 20 and 30 mg doses.

For purposes of this invention a concentration greater than about 20 mg/ml (e.g., 20-45 mg/ml) is considered a "high" concentration. As shown in FIG. 7A and Table 4, subcutaneous injection of a relatively more concentrated solution, for example in a range inclusive of and exceeding 20 mg/ml, e.g., 20-40 mg/ml, will result in a lower Cmax, with a longer half-life. For example, as shown in FIG. 7A and Table 4, subcutaneous administration of exendin(9-39) at a dose of about 20 mg and concentration of about 24 mg/ml exhibited a significantly longer half-life than subcutaneously administered exendin(9-39) at a dose of about 10 mg and concentration of about 16 mg/ml (9.14 hours vs. 3.60 hours). In some embodiments, a more highly concentrated solution of exendin(9-39) results in an exendin(9-39) plasma Cmax that is lower than a relatively lower concentration formulation but which is still greater than a preferred steady state plasma exendin(9-39) concentration of 70 ng/ml or greater (e.g., as shown in FIG. 7A and Table 4 for the "10×" (approximately 20 mg) dose as compared to the "5×" (approximately 10 mg) dose). Thus, a more concentrated solution may be more amenable to less frequent dosing, e.g., QD dosing, or to BID dosing that is not tied to meals.

The examples below demonstrate that subcutaneous injection of a relatively dilute solution, for example of 4-20 mg/ml, and most often 8-16 mg/ml, will result in a pharmacokinetic profile amenable to BID administration (see FIG. 7B and Table 5). In one embodiment the BID dosing will be a morning and evening administration with patients dosing upon awakening in the morning and 12 hours later, i.e. dosing will not be meal-based. In one embodiment, the BID dosing will involve morning and evening administration, with patients dosing 60-150 minutes prior to the morning and evening meals, so that the peak GLP-1 plasma concentration occurring approximately 30-60 post-meal will be countered by sufficient GLP1A plasma concentrations at that time to prevent GLP-1 induced hyperinsulinemia.

The examples below also demonstrate that subcutaneous injection of a more concentrated solution, for example in the range inclusive of and exceeding 20 mg/ml will result in a more sustained release pharmacokinetic profile, with a longer half-life, and thus may be more amenable to less frequent dosing, e.g., qD dosing or BID dosing that is not tied to timing of meals. See, FIG. 7A and Table 4.

In some embodiments, the GLP1A such as exendin(9-39) is administered (e.g., subcutaneously administered) at a concentration of about 4-25 mg/ml, about 4-20 mg/ml, about 10-25 mg/ml, about 10-20 mg/ml, about 10-18 mg/ml, about 8-16 mg/ml, about 12-20 mg/ml, about 10-15 mg/ml, or about 13-16 mg/ml (e.g., about 4 mg/ml, about 5 mg/ml, about 6 mg/ml, about 7 mg/ml, about 8 mg/ml, about 9 mg/ml, about 10 mg/ml, about 11 mg/ml, about 12 mg/ml, about 13 mg/ml, about 14 mg/ml, about 15 mg/ml, about 16 mg/ml, about 17 mg/ml, about 18 mg/ml, about 19 mg/ml, about 20 mg/ml, about 21 mg/ml, about 22 mg/ml, about 23 mg/ml, about 24 mg/ml, or about 25 mg/ml).

In some embodiments, the GLP1A is administered (e.g., subcutaneously administered) at a concentration in the range of about 13 mg/ml to about 16 mg/ml. In some embodiments, the GLP1A is administered at a concentration of about 15 mg/ml.

As shown in FIG. 7B and Table 5, both a relatively lower dose of 10 mg and a relatively higher dose of 30 mg yielded a Cmax greater than the preferred steady state plasma exendin(9-39) concentration of 70 ng/ml or greater and were efficacious in reversing hyperinsulinemic hypoglycemia when administered at approximately equal concentrations in the range of about 13-16 mg/ml. Thus, in one aspect, a relatively lower dose of a GLP1A such as exendin(9-39) (e.g., a dose of about 5-10 mg, e.g., about 5 mg, about 7.5 mg, or about 10 mg) can be efficacious in treating hyperinsulinemic hypoglycemia by adjusting the GLP1A solution to an appropriate concentration as described herein. In some embodiments, a relatively lower dose of a GLP1A such as exendin(9-39) (e.g., a dose of about 5-10 mg, e.g., about 5 mg, about 7.5 mg, or about 10 mg) is administered at a concentration of at least about 10 mg/ml, e.g., at a concentration in the range of about 13-16 mg/ml, e.g., at a concentration of about 15 mg/ml.

Generally a GLP1A such as exendin(9-39) is administered at a concentration sufficient to result in a steady state plasma concentration (e.g., exendin(9-39) concentration) of at least 70 ng/ml, at least 100 ng/ml, or at least 150 ng/ml as measured by liquid chromatograph-mass spectrometry. In some embodiments, the GLP1A (e.g., exendin(9-39)) is administered at a concentration sufficient to result in a steady state plasma exendin(9-39) concentration of about 100-200 ng/ml. In some embodiments, the GLP1A (e.g., exendin(9-39)) is administered at a concentration sufficient to result in a steady state plasma exendin(9-39) concentration of at least 70 ng/ml up to 250 ng/ml.

Table A below provides exemplary therapeutically effective GLP1 (e.g., exendin(9-39)) formulations:

TABLE A

|   | GLP1A | Concentration |
|---|---|---|
| 1 | 10-30 mg | 10-25 mg/mL |
| 2 | 10-30 mg | 10-20 mg/mL |
| 3 | 10-30 mg | 10-18 mg/mL |
| 4 | 10-30 mg | 13-16 mg/mL |
| 5 | 10-25 mg | 10-25 mg/mL |
| 6 | 10-25 mg | 10-20 mg/mL |
| 7 | 10-25 mg | 10-18 mg/mL |
| 8 | 10-25 mg | 13-16 mg/mL |
| 9 | 10-20 mg | 10-25 mg/mL |
| 10 | 10-20 mg | 10-20 mg/mL |
| 11 | 10-20 mg | 10-18 mg/mL |
| 12 | 10-20 mg | 13-16 mg/mL |
| 13 | 10-15 mg | 10-25 mg/mL |
| 14 | 10-15 mg | 10-20 mg/mL |
| 15 | 10-15 mg | 10-18 mg/mL |
| 16 | 10-15 mg | 13-16 mg/mL |
| 17 | 15-30 mg | 10-25 mg/mL |
| 18 | 15-30 mg | 10-20 mg/mL |
| 19 | 15-30 mg | 10-18 mg/mL |
| 20 | 15-30 mg | 13-16 mg/mL |
| 21 | 15-25 mg | 10-25 mg/mL |
| 22 | 15-25 mg | 10-20 mg/mL |
| 23 | 15-25 mg | 10-18 mg/mL |
| 24 | 15-25 mg | 13-16 mg/mL |
| 25 | 15-20 mg | 10-25 mg/mL |
| 26 | 15-20 mg | 10-20 mg/mL |
| 27 | 15-20 mg | 10-18 mg/mL |
| 28 | 15-20 mg | 13-16 mg/mL |

In some embodiments, each administration of the GLP1A (e.g., each BID subcutaneous administration of exendin(9-39)) results in a GLP1A Cmax (e.g., exendin(9-39) Cmax) of at least 100 ng/ml. In some embodiments, for example for patients having relatively higher GLP-1 levels or having greater beta-cell sensitivity to GLP-1, each administration of the GLP1A (e.g., each BID subcutaneous administration of exendin(9-39)) results in a Cmax of at least 150 ng/ml.

In some embodiments, the GLP1A injectate comprises a GLP1A (e.g., exendin (9-39)) dose and concentration that, when administered, results in steady state plasma GLP1A concentration of at least 70 ng/ml, preferably at least 100 ng/ml, or even more preferably at least 150 ng/ml, as measured by LCMS. In some embodiments, the GLP1A (e.g., exendin(9-39)) formulation has such a dose and concentration that results in steady state plasma concentration of 100-250 ng/ml, e.g., 100-200 ng/ml, 100-150 ng/ml, or 150-200 ng/ml.

In some embodiments, each dose is administered in a total volume ranging from 0.25-2 ml injectate, with most patients administering an injection volume ranging from 0.5-1.5 ml, e.g., 0.7-1 ml.

3.3.4.2 Injectate Formulation

The GLP1A may be administered in any pharmaceutically acceptable form. In some embodiments, a GLP1A such as exendin(9-39) is formulated with a pharmaceutically acceptable diluent or carrier that is suitable for subcutaneous administration. Examples of pharmaceutically acceptable diluents or carriers include, but are not limited to, water, saline, and isotonic buffer solutions. In some embodiments the injectate formulation further comprises one or more additional excipients such as preservatives and pH adjustment agents.

In one approach the GLP1A such as exendin(9-39) is formulated in normal saline (0.9% saline). In one approach the GLP1A is formulated with an antimicrobial preservative, a tonicity-adjusting agent, such as mannitol, and/or a buffer (e.g., to bring the solution to a pH of about 4-5).

As shown in Example 3 and FIG. 7A, administration of a lower dose (10 mg, or "5×") resulted in a higher exendin (9-39) Cmax than higher doses formulated in the same volume of solution (i.e., having a higher concentration). Without intending to be bound by a particular mechanism, this may be a result of aggregation (e.g., dimer or higher multimer formation). Thus, in one approach the GLP1A is formulated with an agent to reduce aggregation or dimer formation such as a surfactant (e.g., a non-ionic surfactant, such as a polysorbate or a poloxamer), polyol, or sugar, or by optimizing the pH and/or ionic strength of the solution.

The present invention provides a variety of different formulations, including but not limited to formulations of exendin(9-39) and other GLP-1 antagonists of similar structure and biological activity that provide for more extended release.

3.3.4.2.1 Immediate Release (IR) Formulations

In one aspect, the GLP1A (e.g., exendin(9-39)) is formulated for immediate release. In one aspect of the invention, an immediate-release formulation of exendin(9-39) is provided as a subcutaneous injectable formulation that is administered within 60-150 minutes prior to morning and evening meals (or before the two main meals of the day, approximately 6 hours or more apart). In one aspect of the invention, the immediate-release formulation of exendin(9-39) is administered as a subcutaneous injection in the abdomen, thigh, or upper arm.

In one embodiment, the present invention provides injectable, immediate-release formulations of exendin(9-39), and various derivatives, homologues, and analogues of exendin (9-39), as discussed above, and other GLP-1RAs of similar activity and/or structure to exendin(9-39), wherein said injectable formulations are equivalent to formulations used to deliver exenatide, marketed as BYETTA™ (see U.S. Pat. Nos. 5,424,286; 6,858,576; 6,872,700; 6,902,744; 6,956,026; 7,297,761; 7,521,423; 7,741,269, incorporated herein by reference).

Lyophilized peptide in dual-chamber pen device or vial/syringe device: While exendin(9-39) can be formulated in any way suitable for administration, a suitable immediate release pharmaceutical composition for subcutaneous injection in accordance with the invention contains from about 2.5-40 mg/mL of exendin(9-39) in normal saline or other pharmacologically acceptable liquid or suspension formulation, and may be administered in one or more injections. Such composition will be especially convenient for administration of doses that total about 0.01 to 1 mg/kg body weight, administered by subcutaneous injection in the abdomen, thigh, or upper arm within 1 minute to about 2 hours of meals, with dosing frequency limited to up to 3 times daily, i.e., no more than TID administration. Most patients, however, will benefit from BID administration, which as shown in the examples below can be efficacious when administered as a relatively simply immediate release formulation, and as in the results shown for a more concentrated formulation with longer-acting pharmacokinetics, qD administration will be beneficial for many patients, particularly when an extended or sustained release formulation is administered. While some patients will be administered a standard dose (e.g., 2.5, 5, 10, 20, or 30 mg of exendin(9-39), for example), in other patients, dosing will be initiated at a low dose, and increased stepwise if a lower dose does not result in acceptable glycemic control. The drug product can be supplied as a freeze-dried lyophilized powder, stored in a 1 to 3 mL or larger, e.g., 5 mL, dual-chamber cartridge that is compatible with a disposable pen injector (see, for example, the Ypsomed dual chamber cartridge/pen injector: http://www.ypsomed.com). Two-to-three dose strengths can be conveniently made available to patients, including for example doses in the range of 2-100 mg of exendin(9-39), to be reconstituted in a volume of 0.25-2.0 ml normal saline per dose, or other pharmaceutically acceptable diluent suitable for subcutaneous administration. Typical doses (dose strengths) include, for example and without limitation, 2.5 mg, 5 mg, 10 mg, 20 mg, and 30 mg of exendin(9-39) for immediate and extended release formulations. To achieve a more concentrated solution, for example for a more slow release effect, the same doses may be reconstitution in a smaller volume, for instance in as low as 0.15-0.25 ml. Overall, the concentration for the final reconstituted drug product may range from 2-40 mg/ml, but more often from 5-30 mg/ml. The present invention provides a portable device that permits patients to reconstitute, prime, and inject the lyophilized peptide conveniently "on the go," for example in association with meals. The present invention also provides such compositions in a unit, a single-dose, or a multi-dose glass vial or ampule for administration with the use of a pre-filled syringe containing normal saline or other pharmacologically acceptable liquid or suspension formulation, for use in solubilizing/diluting and subsequently administering a single injection subcutaneously using an insulin syringe. Depending on the dose and concentration of the desired final reconstituted drug product, the number of doses provided could range from 1-40 doses. For example, a 5 mg dose that employs a concentration of 15 mg/ml (equating to 5 mg in 0.33 ml) would provide up to 15 doses, whereas a 10 mg dose at the same concentration would yield a total of 7 doses. If higher concentrations are employed, the number of potential doses provided may increase. In all instances, the use of an antimicrobial or other preservative may be employed, to maintain sterility of the reconstituted drug product if intended for more than single day use.

Sterile (preserved) solution in pen-injector device or in glass vial or ampule and syringe (kit): The present invention also provides exendin(9-39) drug product formulated for subcutaneous injection as a sterile, preserved isotonic solution in a glass cartridge pen-injector device. Such compositions for example and without limitation contain 2-80 mg of exendin(9-39), an appropriate volume of an antimicrobial preservative, a tonicity-adjusting agent, such as mannitol, and a buffer to bring the solution to a pH of about 4-5. As noted, typical doses include 2.5 mg, 5 mg, 10 mg, 20 mg, and 30 mg. A prefilled pen can be made in accordance with the invention to deliver a unit dose of any desired amount, e.g., 5 to 40 mg, e.g., 10 to 30 mg, being typical amounts that could be administered to an adult human. The present invention also provides such compositions in a unit or multi-dose glass vial or ampule for administration with the use of a syringe, similar to the glucagon emergency kit.

3.3.4.2.2 Extended Release (ER) Formulations

In one aspect, the present invention relates to a GLP1A, such as exendin(9-39), formulated for extended release, i.e., an extended release formulation, such that, when administered, the formulation ensures that the active drug product has a lasting presence in the blood throughout the targeted time period in the course of treatment. Use of these formulations and methods allows plasma glucose homeostasis to be maintained with fewer subcutaneous injections, relative to immediate release formulations. Various embodiments of this aspect of the invention are described below.

Encapsulation with Microspheres and Nano-Lipocapsules: A GLP1A (e.g., exendin(9-39)) can be formulated in accordance with the invention as slowly eroding microspheres. Such microspheres include, for example and without limitation, those made with a biopolymer, such as Poly (lactic-co-glycolic acid) (PLGA) or its equivalent. Such formulations provide for release of drug over an extended period of time (1-10 weeks). To prepare the formulation, exendin(9-39) is loaded into the microspheres, and the formulation provides that exendin is steadily released over time as the matrix materials degrade. These microspheres can be formulated to minimize drug bursts and maintain a steady release profile. Alternatively, exendin(9-39) is encapsulated into nano-lipocapsules to prepare another formulation of the invention, which provides similar sustained and extended drug release. These formulations are provided in a variety of particle and capsule sizes and compositions, providing the physician a variety of rapid, medium, and slow release profile formulations to optimize therapy for individual patients.

In one embodiment, the present invention provides injectable, long-acting formulations of exendin(9-39), and various derivatives, homologues, and analogues of exendin(9-39), as discussed above, and other GLP-1RAs of similar activity and/or structure to exendin(9-39), wherein said long-acting formulations are equivalent to formulations used to deliver exenatide, marketed as BYDUREON™ (see U.S. Pat. Nos. 5,424,286; 6,479,065; 6,495,164; 6,667,061; 6,824,822; 6,858,576; 6,872,700; 6,956,026; 7,223,440; 7,456,254; 7,563,871; 7,612,176; 7,741,269; 8,216,180; 8,329,648; 8,431,685; 8,439,864; 8,461,105; and 8,906,851, incorporated herein by reference), or equivalent to formulations used to deliver liraglutide, delivered in a daily dose, marketed as Victoza™ (see U.S. Pat. Nos. 6,004,297; 6,268,343; 6,458,924; 7,235,627; 8,114,833; and 8,846,612).

In one aspect of the invention, the extended-release formulation of exendin(9-39) is provided as a subcutaneous injectable formulation that is administered once daily. In one aspect of the invention, an extended-release formulation of exendin(9-39) is provided as a subcutaneous injectable formulation that is administered once every seven days, at any time of day, and with or without meals. In one aspect of the invention, the extended-release formulation of exendin (9-39) is administered as a subcutaneous injection in the abdomen, thigh, or upper arm region. In one aspect of the invention, the extended-release formulation of exendin(9-39) is administered immediately after the dose is prepared. In some instances, the extended-release formulation of exendin(9-39) is provided as an injectable suspension in a single-dose tray containing a vial of exendin(9-39), a vial connector, a prefilled diluent syringe, and one or more needles. In some instances, the extended-release formulation of exendin(9-39) is provided as an injectable suspension in a single-dose pen containing exendin(9-39), a diluent, and one or more needles.

Other formulations of the invention having a variety of different features and advantages may be made in accordance with the teachings of U.S. Pat. Nos. 8,445,647; 8,895,033; 8,969,293; 8,299,025; 8,546,326; 2015/0258016; 2015/0238568; 2015/0057227; 2015/0056285; 2014/0309168; 2014/0256626; 2013/0252894; 2013/0195939; 2013/0172250, incorporated herein by reference, substituting exendin(9-39) or other biochemically similar GLP-1RA as described herein for the active pharmaceutical ingredient described.

In some embodiments, the GLP1A is formulated as a sterile, preserved isotonic solution in a unit or multi-dose glass vial or ampule for administration with the use of a syringe, similar to the glucagon emergency kit. In some embodiments, the GLP1A is provided as an injectable suspension in a single-dose tray containing a vial of GLP1A, a vial connector, a prefilled diluent syringe, and one or more needles.

In some embodiments, the GLP1A is formulated as a sterile, preserved isotonic solution in a glass cartridge pen-injector device. Such compositions, for example and without limitation contain 5-20 mg of GLP1A, an appropriate volume of an antimicrobial preservative, a tonicity-adjusting agent, such as mannitol, and a buffer to bring the solution to a pH of about 4-5.

In some instances, the formulation of GLP1A is provided as an injectable suspension in a single-dose pen containing GLP1A, a diluent, and one or more needles.

3.3.5 Different Evening and Morning Injectates

In some embodiments, twice-per-day administration comprises administering a morning injectate and an evening injectate that contain different GLP1A (e.g., exendin(9-39)) doses and/or different concentrations of the GLP1A (e.g., exendin(9-39)). Generally, each of the injectates has a GLP1A amount and concentration within the ranges described herein. However, in this embodiment, the amount of GLP1A in the evening administration is greater than the amount in the morning injectate and/or the GLP1A concentration in the evening injectate is greater than the concentration of GLP1A in the morning injectate. In some embodiments the two injectates will have different quantities, the same concentration, of. In some embodiments the two injectates will have the same amount of GLP1A but different concentration. In some embodiments both the concentration and amount of GLP1A will be different.

Without intending to be bound by a particular mechanism, the increased amount of GLP1A administered in the evening may provide higher GLP1A levels at the time of the morning meal. Without intending to be bound by a particular mechanism, the increased concentration of GLP1A is expected to result in a more "flat" plasma concentration profile, including a longer time to Tmax, for a more sustained effect at the time of the morning meal.

In some embodiments the amount of GLP1A (e.g., exendin(9-39)) in the evening injectate is 5 mg to 10 mg greater than the amount in the morning injectate. In some embodiments the amount of GLP1A in the evening injectate is 5 mg greater than the amount in the morning injectate. In some embodiments the amount of GLP1A in the evening injectate is 10 mg greater than the amount in the morning injectate. In some embodiments the amount of GLP1A in the morning injectate is 10 mg, 15 mg, or 20 mg.

In some embodiments the concentration of GLP1A (e.g., exendin(9-39)) in the evening injectate is 5 mg/ml-10 mg/ml greater than the amount in the morning injectate. In some embodiments the concentration of GLP1A in the evening injectate is about 5 mg/ml greater than the amount in the morning injectate. In some embodiments the concentration of GLP1A in the evening injectate is about 10 mg/ml greater than the amount in the morning injectate. In some embodiments the concentration of GLP1A in the morning injectate is 10-16 mg/ml and the concentration of GLP1A in the evening injectate is higher and is in the range of 15-20 mg. In some cases, the amount of GLP1A in the evening injectate is 5 mg-10 mg greater than the amount in the morning injectate. In some such cases the amount of GLP1A in the morning injectate is 10 mg and the amount in the evening injectate is 15 mg. In some such cases the amount of GLP1A in the morning injectate is 10 mg and the amount in the evening injectate is 20 mg. In some such cases the amount of GLP1A in the morning injectate is 15 mg and the amount in the evening injectate is 20 mg. In some such cases the amount of GLP1A in the morning injectate is 15 mg and the amount in the evening injectate is 25 mg. In some such cases the amount of GLP1A in the morning injectate is 20 mg and the amount in the evening injectate is 25 mg. In some such cases the amount of GLP1A in the morning injectate is 20 mg and the amount in the evening injectate is 30 mg.

In some cases, the concentration of GLP1A (e.g., exendin (9-39)) in the morning injectate is not the same as the concentration of GLP1A in the evening injectate. For example, in one approach the concentration of GLP1A in the morning injectate is 15 mg/ml and the concentration of GLP1A in the evening injectate is 20 mg/ml.

In some cases the GLP1A amount and concentration of the morning and evening injectates are selected such that the GLP1A Tmax after the evening administration is longer than the Tmax after the morning administration.

In one approach, the evening injectate is prepared or formulated to favor multimerization (e.g., dimerization) or precipitation of the GLP1A. Administration of the injectate at bedtime can delay absorption, producing a slower release profile compared to the morning administration, resulting in an advantageous basal morning level of at least 30 ng/mL Methods for preparing compositions comprising multimerized proteins are known. For example, the addition of a basic protein, such as protamine, to the GLP1A preparation can favor formation of multimer peptide configurations. Alternatively, multimerization can be achieved by precipitating the GLP1A out of solution, for example through the addition of salts, such as zinc salts, such that the molar ratio of the salt with respect to GLP1A is greater than 1, so as to reduce the solubility of the GLP1A in a neutral solvent. In this approach raising the pH (for example to 7.4), in the presence of such salts, can be used to favor precipitation of the peptide. Thus, in some embodiments the level of aggregation or multimerization in the evening injectate is greater than the level in the morning injectate. In some embodiments the GLP1A is in a less soluble form in the evening injectate compared to the morning injectate.

In some embodiments an immediate release formulation (e.g., as described herein) is administered in the morning and an extended release formulation (e.g., as described herein) is administered in the evening (e.g., before bedtime).

3.3.6 Duration of Therapy

Patients may receive therapy for a predetermined time, an indefinite time, or until an endpoint is reached. Treatment may be continued on a continuous daily or weekly basis for at least two to three months, six months, one year, or longer. In some embodiments, therapy is for at least 30 days, at least 60 days, at least 90 days, at least 120 days, at least 150 days, or at least 180 days. In some embodiments, treatment is continued for at least 6 months, at least 7 months, at least 8 months, at least 9 months, at least 10 months, at least 11 months, or at least one year. In some embodiments, treatment is continued for the rest of the patient's life or until administration is no longer effective in maintaining normal plasma glucose levels to provide meaningful therapeutic benefit. In some embodiments, adult patients (60-100 kg or more) will receive therapeutic benefit from a single dose of GLP1A.

3.4 Delivery Devices

Devices such as injectable pen devices and pumps suitable for subcutaneous injections are well known. Such devices may be used to deliver the GLP1A (e.g., exendin (9-39)) formulations described hereinabove according to the methods described herein.

3.4.1 Subcutaneous Pump

In one embodiment, the method of the invention is practices with use of a subcutaneous pump, and the invention provides such pumps containing the GLP1A, e.g., exendin(9-39) or a conjugate thereof, formulated as described herein for subcutaneous delivery. This methodology can confer tighter plasma glucose control for some patients and is generally very convenient for the patient. Compositions for such method provided by the invention include solution formulations and freeze dried lyophilized powder for reconstitution. See, e.g., Kumareswaran et al., *Discovery Medicine*, 2012, 13:159-170, incorporated by reference herein.

3.4.2 Injectable Pen Device

In some embodiments, GLP1A (e.g., exendin(9-39)) is administered using an injectable pen device that may be pre-programmed to deliver a fixed dosage amount. In some embodiments, the device is pre-programmed to deliver a fixed dosage ranging from 5-30 mg, e.g., 10-20 mg, or 7.5-15 mg, depending upon the needs and physical attributes of the patient. In some embodiments, the GLP1A (e.g., exendin(9-39)) is formulated as an immediate release preparation, and is packaged, for example, in the form of a single or dual-chamber pen device (e.g., a 1 to 5 mL dual chamber pen—either a disposable pen or one that reloads disposable cartridges).

The drug product can be supplied as a freeze-dried lyophilized powder, stored in a 1 to 3 mL or larger, e.g., 5 mL, dual-chamber cartridge that is compatible with a disposable pen injector (see, for example, the Ypsomed dual chamber cartridge/pen injector: www.ypsomed.com). Two-to-three dose strengths can be conveniently made available to patients, including for example doses in the range of 5-30 mg of exendin(9-39), to be reconstituted in a volume of 0.25-2.0 ml normal saline per dose, or other pharmaceutically acceptable diluent suitable for subcutaneous administration.

In some embodiments, the drug product is supplied as individual injectable pen devices that are pre-programmed to deliver a fixed dosage amount, in which the morning dosage amount and the evening dosage amount are different amounts and/or concentrations. For example, in some embodiments, a first pen (e.g., for morning administration) delivers a dose in the range of 5-15 mg (e.g., a dose of 5 mg, 7.5 mg, 10 mg, 12.5, or 15 mg) and a second pen (e.g., for evening administration) delivers a higher dose in the range of 15-20 mg (e.g., a dose of 15 mg, 17.5 mg, or 20 mg). In some embodiments, the first pen delivers a dose of 10 mg and the second pen delivers a dose of 15 mg. In some embodiments a first pen delivers a dose of 15 mg and the second pen delivers a dose of 20 mg.

In another aspect, the present invention provides kits comprising individual injectable pen devices as described herein. In some embodiments, a kit comprises a plurality of individual injectable pen devices (e.g., 2, 3, 4, 5, 6, 7, 8, 9, 10 or more pens in a kit). In some embodiments, the kit comprises two or more individual injectable pen devices that are pre-programmed to deliver a fixed dosage amount, in which the morning dosage amount and the evening dosage amount are different amounts and/or concentrations. For example, in some embodiments, the kit comprises a first pen (e.g., for morning administration) that delivers a dose in the range of 5-15 mg (e.g., a dose of 5 mg, 7.5 mg, 10 mg, 12.5, or 15 mg) and further comprises a second pen (e.g., for evening administration) that delivers a higher dose in the range of 15-20 mg (e.g., a dose of 15 mg, 17.5 mg, or 20 mg). In some embodiments, the kit comprises a first pen that delivers a dose of 10 mg and a second pen that delivers a dose of 15 mg. In some embodiments, the kit comprises a first pen that delivers a dose of 15 mg and a second pen that delivers a dose of 20 mg.

3.5 Treatment Outcomes

In some embodiments, patients treated with the compositions and methods described herein exhibit an improvement in one or more symptoms of hypoglycemia, including but not limited to neuroglycopenic symptoms, beta-adrenergic symptoms, or plasma glucose levels.

In some embodiments, treatment in the typical adult or pediatric patient refers to treatment such that the postprandial plasma glucose nadir is maintained above a concentration of approximately 55 mg/dl (3.0 mmol/liter) based upon the Endocrine Society's Clinical Guidelines (*Journal of Clinical Endocrinology & Metabolism*, March 2009, 94(3): 709-728), and symptoms of hypoglycemia are reduced. Ideally, normal plasma glucose concentrations are maintained, with those skilled in the art recognizing that in humans a blood glucose level of 65 mg/dl or greater is preferred.

In some embodiments, treatment in a patient refers to treatment such that at least a 15% increase in postprandial plasma glucose nadir is achieved relative to baseline (e.g., before the onset of treatment). In some embodiments, treatment in a patient refers to treatment such that for a patient having a postprandial plasma glucose nadir ≤50 mg/dl at baseline (e.g., before the onset of treatment), an increase in postprandial plasma glucose nadir to ≥55 mg/dl is achieved relative to baseline.

Plasma glucose nadir can be measured, for example, by oral glucose tolerance test (OGTT) or meal tolerance test (MTT) as described herein. In some embodiments, treatment in a patient refers to treatment such that a statistically significant decrease in the severity of one or more symptoms of hypoglycemia overall during a OGTT or MTT and/or of neuroglycopenic symptoms elicited during the glucose "fall" period of OGTT or MTT is achieved relative to baseline (e.g., before the onset of treatment).

3.6 Co-Administration with an Amylinomimetic or Other Gastric Emptying Agent Some patients may enjoy added therapeutic benefit from the co-administration, in accordance with the invention, of an amylinomimetic or other agent that delays gastric emptying with exendin(9-39) or other GLP1A, as described herein. Delayed nutrient transit due to co-administration of such an agent can diminish the postprandial glucose peak, therein reducing the peak-to-nadir plasma glucose drop, and the rate at which this drop occurs. While not to be limited or construed by any theory, one insight that lead to the invention was the discovery that the plasma glucose concentration itself did not appear to be the primary elicitor of the early symptoms of hypoglycemia; instead, the rate at which the glucose decline occurs and the period of time over which that occurs appear to be the fundamental causative factors. Accordingly, the inventors had the insight that combining a GLP-1 antagonist, such as exendin(9-39), with an amylinomimetic, such as an amylin peptide or another agent that delays gastric emptying, can improve the treatment of hyperinsulinemic hypoglycemia, at least for some patients, relative to treatment with a GLP1A alone.

The novel formulations that result from combining a lyophilized amylin peptide with exendin(9-39) or other GLP-1 antagonist in a composition for subcutaneous injection or inhaled pulmonary delivery provided by the invention are particularly convenient for achieving simultaneous administration of these agents in accordance with the invention. For example, one such formulation is prepared by dissolving amylin in aqueous solution together with exendin (9-39). This solution can be spray dried to produce a powder product of the invention. Alternatively the amylin peptide and the Exendin(9-39) product can be administered in the form of two separate powders that are co-administered using a device with a double chamber design, or alternatively administered as a physical mixture of the two powders. Various other methods and formulations of the invention are prepared by combinations of exendin(9-39) with a different agent that has the effect of delayed gastric emptying, such as an aluminum hydroxide antacid, any H2 Receptor Antagonist (e.g. Ranitidine, Cimetidine, or Famotidine), or any Proton Pump Inhibitor, (e.g. Omeprazole, Lansoprazole, or Pantoprazole).

3.7 Dose Escalation

While the results in the examples below clearly demonstrate that doses of 10, 20, and 30 mg in a simple immediate release formulation of the invention will result in a therapeutic treatment effect (with desired treatment outcomes as above described), those practiced in the art will appreciate that other doses, as described herein, can be therapeutically beneficial for some patients. Some physicians may desire to treat with a low or initiating (starting) dose (e.g., 5-7.5 mg), escalate to an increased if the initiating dose does not result in acceptable glycemic control, and maintain the initiating dose if glycemic control is sufficient. For example, some physicians may desire to treat with a low or initiating (starting) dose and then escalate, e.g., the low and/or initiating dose may be 5-10 mg, the middle dose may be 10-20 mg, and the high dose may be 20-30 mg, with the physician stopping the dose elevation when satisfactory (maximal) therapeutic benefit is obtained.

In some embodiments, a starting dose of 10 mg of GLP1A (e.g., exendin(9-39)) in a morning dose and 10 mg GLP1A (e.g., exendin(9-39)) in an evening dose is administered to the subject. If this dose does not result in sufficient coverage in the morning (e.g., does not result in sufficient glycemic control at the time of the morning meal), the evening dose may be increased, e.g., to 15 mg exendin(9-39) as the evening dose. In some embodiments, a starting dose of 15 mg exendin(9-39) in a morning dose and 15 mg exendin(9-39) in an evening dose is administered to the subject. If this dose does not result in sufficient coverage in the morning, the evening dose may be increased, e.g., to 20 mg exendin (9-39) as the evening dose.

Furthermore, depending upon the severity of the presenting patients' condition, for instance for patients presenting with a history of seizure, loss of consciousness, or other neuroglycopenic episodes, a higher and/or a more dilute dose of exendin(9-39) (or bioequivalent amounts of another GLP1A) with multiple injections optionally prescribed by the treating physician. For most patients, however, the treating physician will instruct the treated patient to follow standard prescribing information. An illustrative, non-limiting example of such instructions, based on use of the formulations as described in the examples, is provided for illustrative purposes, as follows:

DOSAGE AND ADMINISTRATION: Inject subcutaneously in the abdomen, thigh, or upper arm. Administer within 60-150 minutes prior to morning and evening meals, or before the two main meals of the day, approximately 6-10 hours apart. Initiate at a dose of 5 mg. If this dose does not result in acceptable glycemic control, the dose can be increased to 10 mg. If this does not result in acceptable glycemic control, the dose can be increased stepwise to 15 mg (1×5 mg+1×10 mg dose), then 25 mg (1×15 mg dose+ 1×5 mg dose) if needed.

DOSAGE FORMS AND STRENGTHS: Exendin(9-39) is supplied as a 1 to 5 mL dual chamber pen—either a disposable pen or one that reloads disposable cartridges—that delivers doses of: 5 mg per dose, 10 mg per dose, 15 mg per dose, or 25 mg per dose if needed. Contraindications, warnings, and precautions might include, for example, a history of severe hypersensitivity to a GLP-1 agonist (exenatide, for example) or GLP-1 antagonist (exendin(9-39), for example). Hyperglycemia: May occur when exendin(9-39), in particular if exendin(9-39) is used in connection with other medications known to raise plasma glucose (e.g., octreotide, diazoxide, corticosteroids). Renal Impairment: Exendin(9-39) is excreted renally and should not be used in patients with severe renal impairment or end-stage renal disease. Caution should be used in patients with renal transplantation and when initiating or escalating doses in patients with renal impairment. Should hypersensitivity reactions occur, (e.g., anaphylactic reactions and angioedema) the patient should discontinue exendin(9-39) and other suspect medications and seek medical advice. The label above is for an immediate or extended release formulation of exendin(9-39) administered by dual- or single-chamber pen—either disposable or re-loadable with cartridges—or by vial/syringe device.

These and other benefits of the invention will be appreciated in greater depth upon contemplation of the examples below and accompanying figures, which conclusively demonstrate that administration of a GLP1A as described herein can provide immediate and significant benefit to post-bariatric patients suffering hypoglycemic excursions after consuming normal amounts of glucose. Based upon American Society of Metabolic and Bariatric Surgery (ASMBS) recommendations (see asmbs.org/patients/life-after-bariatric-surgery), post-bariatric surgery patients are encouraged to limit their carbohydrate intake to 50 grams per day or less. Patients in the examples provided were administered 75 grams of carbohydrate within a 20 minute period of time, amounting to 1.5-fold the total ASMBS recommended daily intake. Thus based upon the success demonstrated in the examples wherein administration of a GLP1A prevented hypoglycemia and markedly improved symptoms after a high carbohydrate load, under ordinary conditions, similar or greater efficacy would be anticipated.

4. Examples

4.1 Example 1: Continuous IV Infusion of Exendin(9-39) Effectively Reverses Hyperinsulinemic Hypoglycemia and Associated Symptoms A randomized placebo-controlled blinded cross-over Phase 1 study was conducted to determine whether continuous IV infusion of exendin(9-39) can effectively reverse hyperinsulinemic hypoglycemia and associated symptoms. Exendin(9-39) was acquired as a lyophilized peptide: exendin(9-39) acetate 10 mg/vial from Bachem (Clinalfa, Läufelfingen, Switzerland). For preparation of the IV infusate, lyophilized exendin(9-39) was solubilized with 20 ml 0.9% normal saline (NS) for every 10 mg peptide, then diluted in 100 ml 0.9% NS and 50 ml of 25% human serum albumin, in a PVC-free, DEHP-free 1 L infusion bag. The bag was covered with an opaque IV bag cover to aid with blinding. An identical-appearing bag was prepared, constituting the placebo infusate, containing the same volume of infusate (NS only) without the presence of peptide or albumin. Eight patients with hyperinsulinemic hypoglycemia were randomized to receive an infusion of placebo and an infusion of exendin(9-39) in cross-over design during an oral glucose tolerance test (OGTT) on two separate days separated by no greater than 2 weeks. Patients were asked to fast for 12 hours prior to the infusion of study drug or placebo, and infusions and OGTTs were carried out the Center for Translational Research Unit (CTRU) at Stanford University. On the day of admission to CTRU, 2 IV lines were placed for infusion of study drug and blood collection. Fasting blood was drawn at T-40 minutes. At T-30 minutes, an IV bolus of 7,500 pmol/kg exendin(9-39) or placebo was administered over 1 minute, while a continuous IV infusion of exendin(9-39) at a rate of 500 pmol/kg/min (providing an infusion dose of about 0.35 mg/kg) or placebo (0.9% saline) was initiated and run for 210 minutes. At T+0 minutes an OGTT was initiated, wherein patients were instructed to consume a 75 g glucola drink over 20 minutes.

Plasma samples were collected at T-40, T+0, T+30, T+45, T+60, T+90, T+105, T+120, T+150, T+180 and at each timepoint immediately taken to the laboratory for processing. The following assays were then conducted: glucose, insulin, GLP-1, GIP, glucagon, and exendin(9-39). If glucose levels dropped to 50 mg/dL or less, the test was stopped and investigators intervened as needed to normalize glucose. At T-40 and concomitant with timed blood draws, a graded symptom questionnaire was completed repetitively by patients. This questionnaire was adapted from two validated hypoglycemia assessment tools, by segregating symptoms into three clear factors: autonomic, neuroglycopenic, and malaise, and then by adding a severity gradation scale, such that patients rated the severity of each reported symptoms from 1-5 (1: least severe; 5: most severe).

As shown in FIG. 1B and Table 1, patients exhibited an average glucose nadir of approximately 80 mg/dL during exendin(9-39) infusion, as compared to a nadir of <50 mg/dL during placebo infusion. Patients also exhibited a marked decrease in plasma insulin concentrations during exendin(9-39) infusion (see FIG. 1A and Table 1).

Figure 2C:
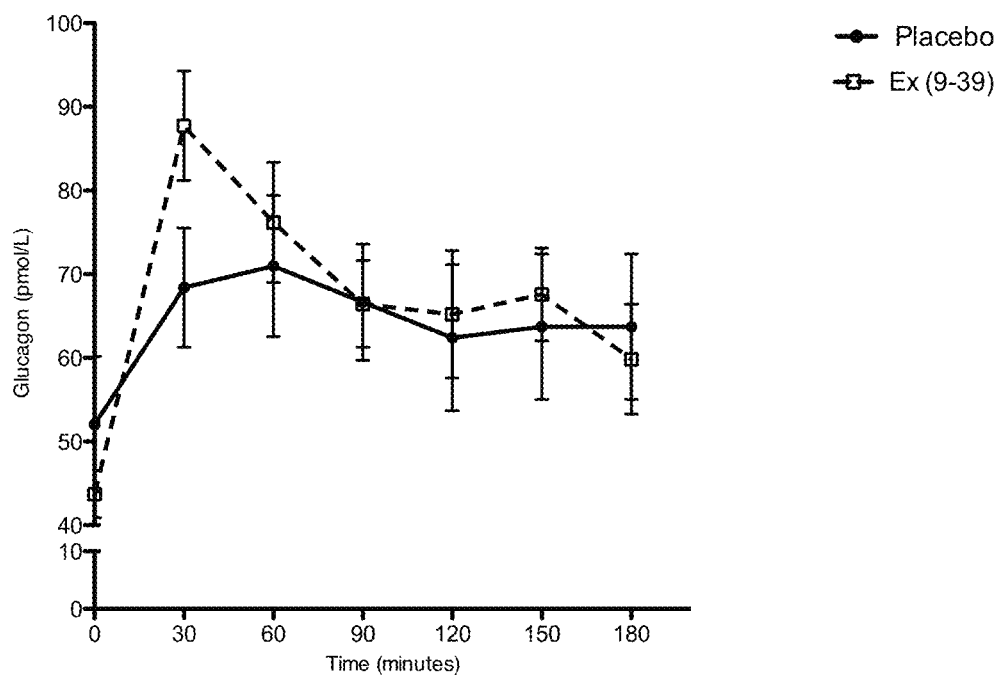

Metabolic responses, including plasma GLP-1, GIP, and glucagon responses, were measured as shown in FIG. 2 A-C, and Table 2. Although area under the curve (AUC) values were calculated as shown in Tables 1 and 2, the presentation of the data graphically, as presented in FIGS. 1 and 2, is more informative because subject OGTTs were stopped prematurely if they became hypoglycemic (as they did in 100% of cases during placebo infusion). For calculation of AUC in cases of premature cessation of the OGTT, the last value was carried forward. Patients were also assessed for hypoglycemic symptoms during exendin(9-39) infusion vs. placebo infusion. As shown in FIG. 3, continuous exendin (9-39) infusion substantially improved symptoms of hypoglycemia, as demonstrated by the dramatically reduced total hypoglycemic symptom assessment score. Additionally, to isolate symptoms associated with glucose rise and fall, two subscores were included: the "Glucose Fall" score, which encompasses symptoms associated with the fall in glucose to nadir, and the "Glucose Rise" score, which encompasses symptoms associated with the rise in glucose to peak.

The results demonstrate that continuous IV infusion of exendin(9-39) effectively reverses hyperinsulinemic hypoglycemia and associated symptoms.

4.2 Example 2: Single IV Bolus Injection of Exendin(9-39) Reverses Hypoglycemia Only if Timed Coincide with Peak GLP-1 Plasma Concentrations A trial was performed to assess whether a single bolus dose of exendin(9-39) was able to prevent hypoglycemia in a 75 gram OGTT with subjects with hyperinsulinemic hypoglycemia. Two subjects with hyperinsulinemic hypoglycemia were admitted to the research clinic after a 12 hour overnight fast. An IV bolus of 7,500 pmol/kg exendin(9-39) was prepared as in Example 1. The subjects consumed a 75 gram glucola at T=0. GLP-1 levels are predicted to peak about 60 min after the administration of glucola (see, Myint et al., *European Journal of Endocrinology*, 2012, 166:951-955; see also FIG. 4D). After consuming the glucola, the subjects were infused intravenously with an IV bolus of exendin(9-39) over 1 minute, with the timing of the IV bolus administration relative to the 75 gram OGTT altered on different days, as follows: T=0, T+20, and T+50. Plasma was assayed at T−40, T+0, T+30, T+45, T+60, T+90, T+105, T+120, T+150, T+180 and at each timepoint immediately taken to the laboratory for processing. Measurements were taken for glucose, insulin, GLP-1, GIP, glucagon, and exendin(9-39). Bioavailability/PK profile of IV exendin(9-39) was evaluated by Cmax, Tmax, AUC0-∞, AUClast, VZ, CL, and $T_{1/2}$. Exendin(9-39) concentration was measured by radioimmunoassay (RIA) as described in Kielgast et al., *Diabetes*, 2011, 60:1599-1607.

Figure 4D:
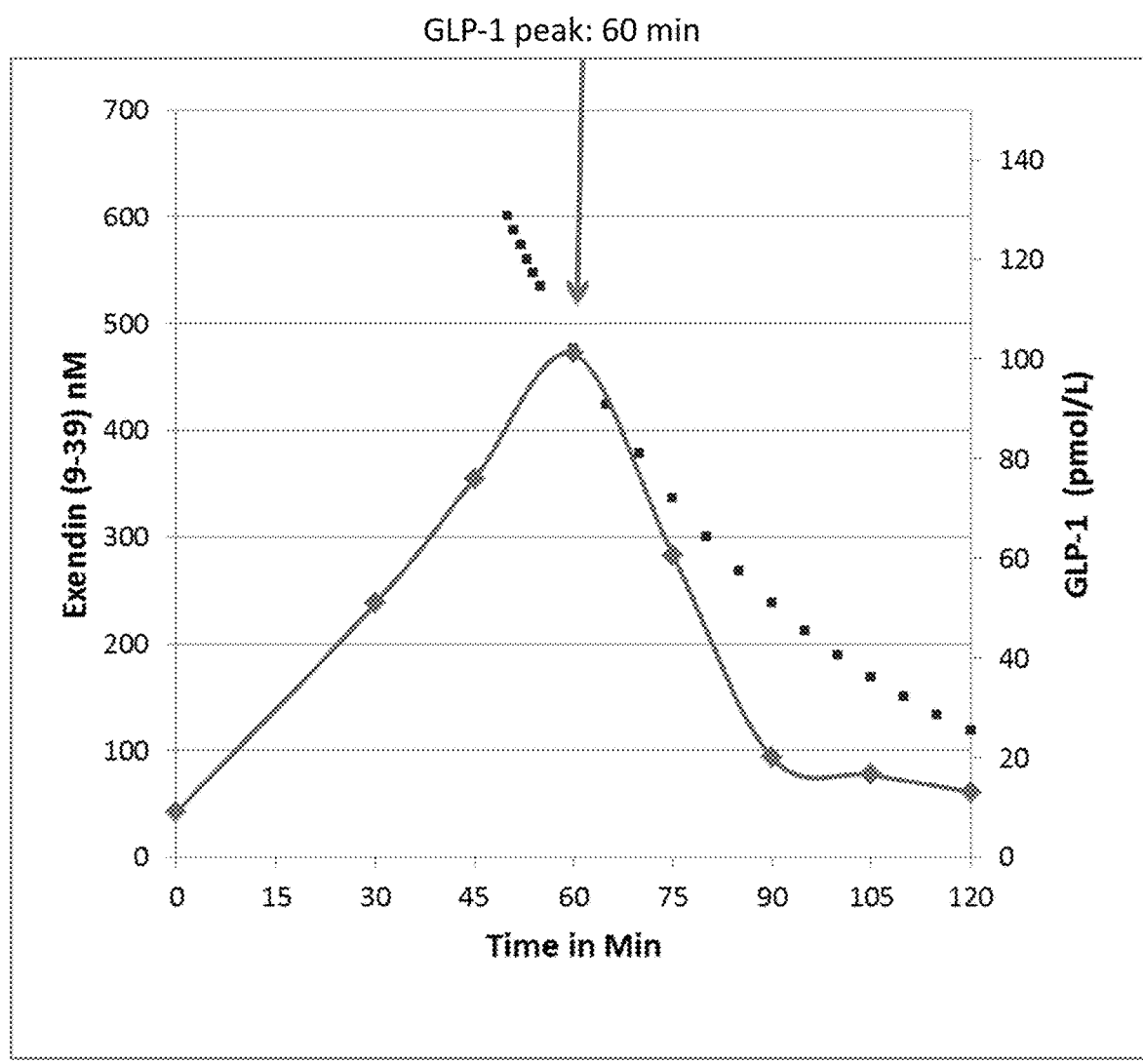

As shown in FIGS. 4A-C, dosing of the IV bolus of exendin(9-39) at 0 minutes or 20 minutes following administration of glucola did not prevent hypoglycemia, whereas dosing at 50 minutes after administration of glucola did prevent hypoglycemia. See, figure legend. FIGS. 4A-D demonstrates that peak plasma exendin(9-39) concentrations in the range of 500-600 nMol/L by radioimmunoassay at the time of peak plasma GLP-1 concentrations are required to avoid a glucose nadir below 50 mg/dL. The results shown in FIG. 4A-D suggest that in the absence of continuous IV infusion, or in the absence of an IV bolus timed precisely to the peak predicted GLP-1 plasma concentrations, hypoglycemia cannot be averted.

Exendin(9-39) plasma levels can be measured using a radioimmunoassay (RIA) generally as described in Kielgast et al., *Diabetes*, 2011, 60:159-1607. Exendin(9-39) plasma levels can be measured using liquid chromatography-mass spectrometry (LCMS) methodology generally as described in Lasaosa et al., *J. Chromatogr B Analyt Technol Biomed Life Sci*, 2014, 0:186-191. We refer to both methods in the discussion herein, and both methods are used in the scientific literature. We observed that measurement of plamsa exendin (9-39) values using RIA were significantly higher than values determined using LCMS. We believe the LCMS values are more accurate. For definitional purposes, a claimed exendin(9-39) concentration (e.g., Cmax) refers to the absolute quantity of Exendin(9-39) which may be determined by LCMS or another equally quantitative method.

Figure 5A:
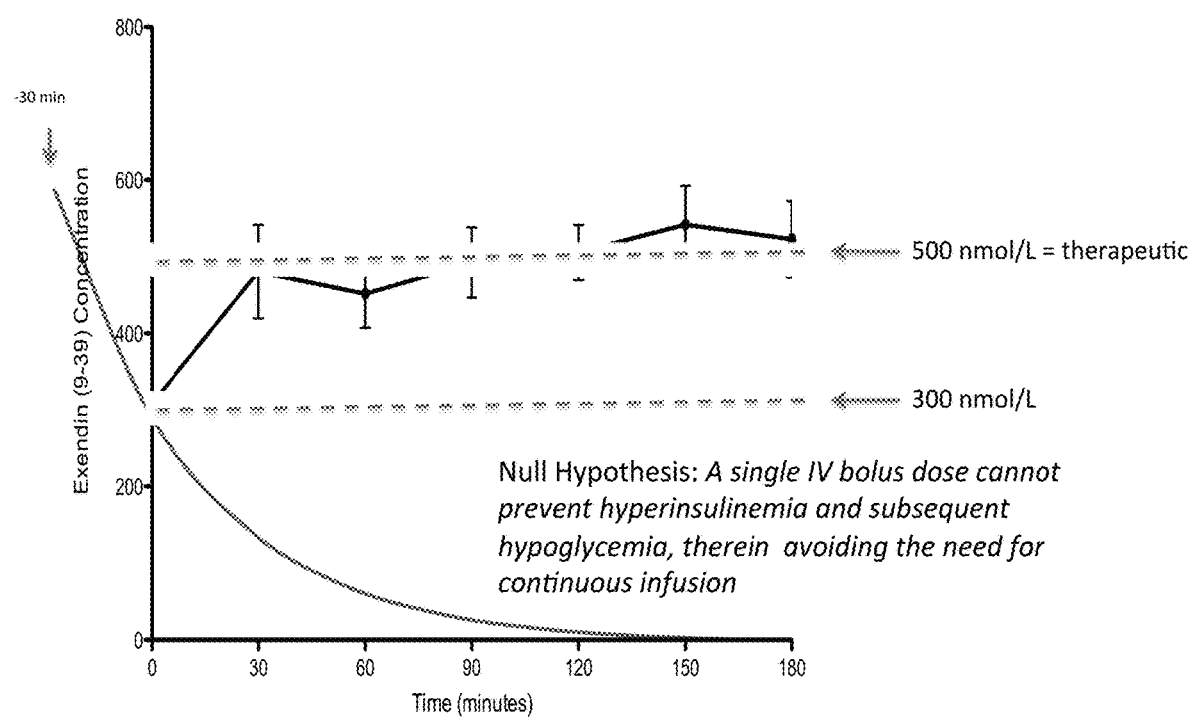
FIG. 5A-B. (A) Average plasma exendin(9-39) concentrations for 8 human subjects administered a continuous exendin(9-39) IV infusion at a rate of 500 pmol/kg/min over 180 minutes are plotted (black line). The projected exendin (9-39) pharmacokinetic response to a single IV bolus of 7,500 pmol/kg exendin(9-39) administered at T-30 (blue line) was extrapolated based on the known half-life of intravenously administered exendin(9-39). (B) A single IV bolus of 7,500 pmol/kg exendin(9-39) or a single subcutaneous injection of 7,500 pmol/kg exendin(9-39) was administered to a subject. Plasma exendin(9-39) concentrations were measured by liquid chromatography-mass spectrometry (LCMS). The Cmax that was observed in subcutaneous administration of exendin(9-39) was significantly lower than the Cmax observed in intravenous administration of exendin (9-39).

FIG. 5A depicts an average of eight patients' plasma exendin(9-39) concentrations at various timepoints following a 7,500 pmol/kg IV bolus of exendin(9-39) at T−30 minutes, followed by continuous IV fusion at a rate of 500 pmol/kg/min over 210 minutes as described in Example 1. See graph line with error bars. It has also been reported that in healthy subjects an intravenous infusion of exendin(9-39) at 500 pmol/kg/min fully reverses the glucose lowering effect of GLP-1. See, Edwards et al., *Diabetes*, 1999, 48:86-93. Based on the measured plasma exendin(9-39) concentrations as shown in FIG. 5A, a steady plasma exendin(9-39) concentration of approximately 500 nmol/L (as measured by radioimmunoassay) or of approximately 140 nmol/L (as measured by LCMS) is presumed to be required for efficacy.

FIG. 5A also shows the projected exendin(9-39) plasma concentration that would be expected from administering a single IV bolus of 7,500 pmol/kg exendin(9-39) at T-30 minutes. As previously reported, the half-life of a single dose of intravenously administered exendin(9-39) is about 33.5 minutes (see, Edwards et al., Diabetes, 1999, 48:86-93). Extrapolating from the exendin(9-39) concentration measured at T=0 (about 300 nmol/L as measured by RIA) it was concluded that the exendin concentration at T=−30 is about 600 nmol/L given the half-life of intravenously administered exendin(9-39). In view of the projected pharmacokinetic response for exendin(9-39) and the time course of the development of hypoglycemia following a meal (typically 1-3 hours after meals, with peak GLP-1 levels expected at about 60 minutes after the meal), a single IV bolus dose administered prior to or with a meal would likely not be effective for treatment of hyperinsulinemic hypoglycemia, because the exendin(9-39) plasma concentration would be expected to be very low at the predicted time of peak GLP-1 levels. Furthermore, even if an IV bolus having a higher dose of exendin(9-39) were administered, it would be expected to exhibit similar pharmacokinetic properties of a short half-life and rapid elimination from plasma. In view of the time course for the development of hypoglycemia and the lag between the time of a meal and the projected peak GLP-1 levels, even an IV bolus having a higher dose of exendin(9-39) would not be expected to be efficacious in averting hypoglycemia unless precisely timed with predicted peak plasma GLP-1 levels.

4.3 Example 3: A Single Dose of Subcutaneously Injected Exendin(9-39) Effectively Reverses Hyperinsulinemic Hypoglycemia and Associated Symptoms As described above in Example 1, it was found that an IV bolus of 7,500 pmol/kg exendin(9-39) plus a continuous IV infusion of exendin(9-39) at a rate of 500 pmol/kg/min over 210 minutes was efficacious in reversing hyperinsulinemic hypoglycemia and associated symptoms. For the peptide exenatide, it has been reported that the absorption kinetics of exenatide in rats most closely approximates human absorption kinetics. See, Chen et al., *Interspecies Modeling Pharm Res.*, 2013, 30:751-760. Rat intravenous and subcutaneous dose escalation pharmacokinetic data predicts that in humans, the Cmax of subcutaneously administered exendin (9-39) would be substantially lower than the Cmax of intravenously administered exendin(9-39). Accordingly, it was expected that a higher dose of exendin(9-39) would be needed for subcutaneous administration, as compared to intravenous administration, in order for exendin(9-39), to be effective in reversing hyperinsulinemic hypoglycemia.

Figure 5B:
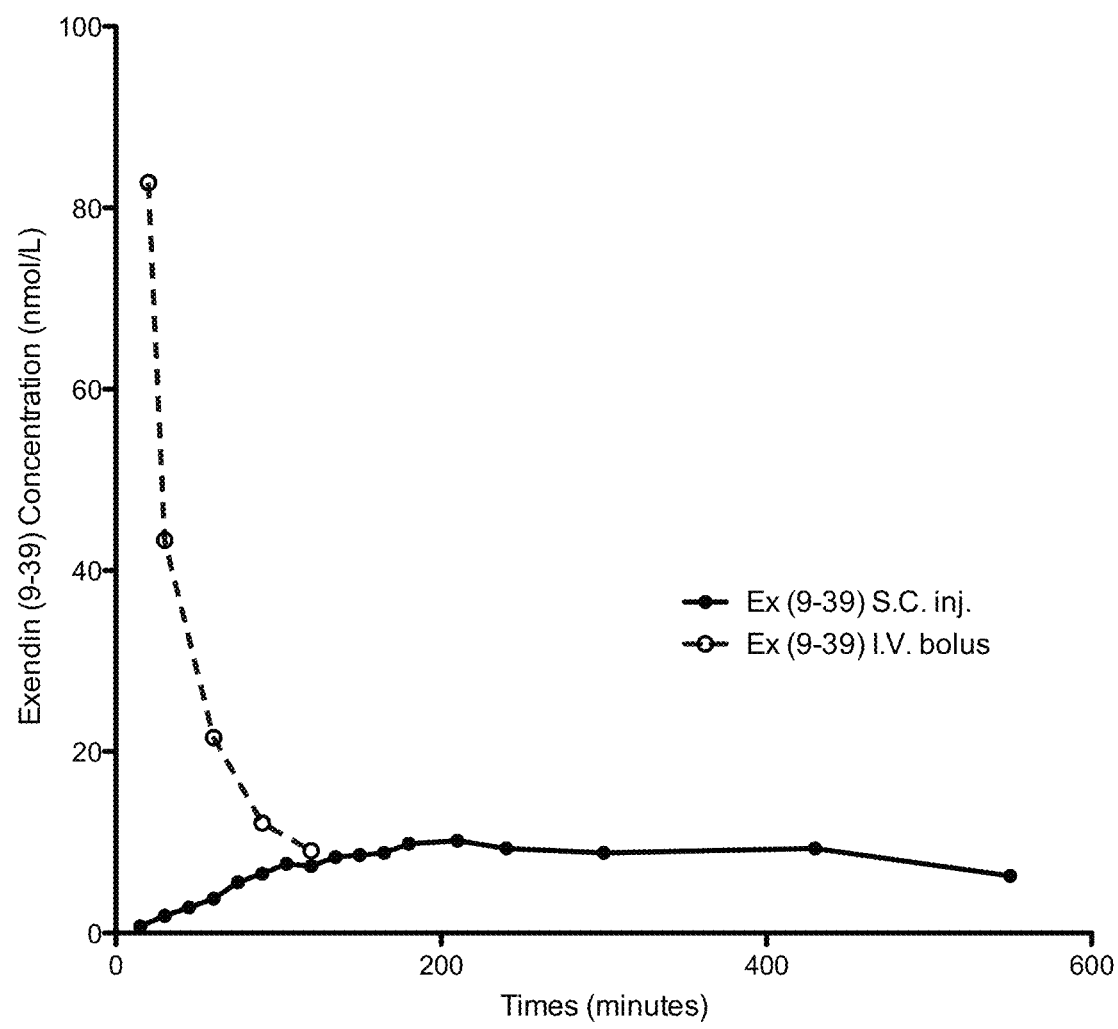

To compare the pharmacokinetic parameters of intravenously or subcutaneously administered exendin(9-39), a single IV bolus of 7,500 pmol/kg exendin(9-39) or a single subcutaneous injection of 7,500 pmol/kg exendin(9-39) was administered in one subject on two separate days. The IV bolus consisted of 0.025 mg/kg of lyophilized exendin(9-39) (which equates to a dose of approximately 2 mg for an 80 kg patient) solubilized in 20 ml per 10 mg exendin(9-39) (approximately 4 ml normal saline) and then diluted in 100 ml 0.9% normal saline for every 10 mg exendin(9-39) (approximately 20 ml 0.9% normal saline), to which approximately 10 ml 25% human serum albumin was added (50 ml 25% human serum albumin for every 10 mg exendin (9-39)), for a total IV bolus infusion volume of approximately 34 ml. The IV bolus infusion was administered over 1 minute. The subcutaneous injection consisted of 0.025 mg/k of lyophilized exendin(9-39) (which equates to a dose of approximately 2 mg for an 80 kg patient) solubilized in 0.2 ml normal saline and further diluted in 0.5 ml normal saline to a total volume of 0.7 ml for subcutaneous injection in the arm. Plasma exendin(9-39) concentrations were measured by liquid chromatography-mass spectrometry (LCMS) as described in Lasaosa et al., supra Example 1. As shown in FIG. 5B, the Cmax that was observed in subcutaneous administration of exendin(9-39) was significantly lower than the Cmax observed in intravenous administration of exendin (9-39), further supporting the hypothesis that for subcutaneous administration, a higher dose of exendin(9-39) would be required for preventing hyperinsulinemic hypoglycemia, as compared to efficacious doses of intravenously administered exendin(9-39).

A single ascending dose (SAD) study was performed to assess the pharmacokinetics, efficacy, and local tolerability of administering exendin(9-39) by subcutaneous injection. For the SAD study, nine subjects with hyperinsulinemic hypoglycemia were randomized to one of four experiments, each representing one of four subcutaneous doses of exendin (9-39): 7,500 pmol/kg, 37,500 pmol/kg, 75,000 pmol/kg, or 112,500 pmol/kg. Lyophilized exendin(9-39) acetate 10 mg/vial from Bachem (Clinalfa, Läufelfingen, Switzerland) was acquired for each experiment, with each 10 mg vial solubilized in 200 µl normal saline, then further diluted with normal saline to a total dose of 7,500 pmol/kg, 37,500 pmol/kg, 75,000 pmol/kg, or 112,500 pmol/kg (2.0 mg, 10 mg, 20 mg, or 30 mg of exendin(9-39), respectively, based on a patient weight of 80 kg). The total volume of each injectate was held constant, with further dilution of injectate as required to result in a total volume of injectate of 0.7 ml. Of the nine subjects, five subjects were randomized to receive one subcutaneous injection of 7,500 pmol/kg, 37,500 pmol/kg, 75,000 pmol/kg, or 112,500 pmol/kg (2, 10, 20, and 30 mg, respectively, based on an 80 kg patient) in a volume of 0.7 ml normal saline, and four subjects received two or more 0.7 ml injections of 75,000 pmol/kg, or 112,500 pmol/kg in order to maintain an injectate concentration of about 15 mg/ml or less.

Subjects fasted overnight for 12 hours and were admitted to the research clinic. One IV line was placed in the patient for blood collection. Fasting blood was drawn. Subjects were injected subcutaneously in the abdomen with the dose of exendin(9-39) to which they were randomized, and were blinded as to which dose they were receiving. For the subjects receiving a dose of 37,500 pmol/kg, 75,000 pmol/kg, or 112,500 pmol/kg, an OGTT was initiated at T+0 minutes, wherein patients were instructed to consume a 75 g glucola drink over 20 minutes. Plasma samples were collected at T−10, T−0, T+15, T+30, T+45, T+60, T+75, T+90, T+105, T+120, T+135, T+150, T+165, T+180, T+210, T+240, T+300, T+480, and T+1440, and at each timepoint the samples were immediately taken to the laboratory for processing.

The following parameters were evaluated: 1) plasma glucose, insulin, glucagon, GLP-1, and GIP concentration; 2) bioavailability/PK profile of subcutaneous exendin(9-39): Cmax, Tmax, AUC0-∞, AUClast, VZ, CL, $T_{1/2}$, and bioavailability; 3) local tolerability after subcutaneous injection of exendin(9-39) utilizing a Visual Analog Scale (VAS) and a Numeric Rating Scale (NRS); and 4) local swelling as measured by caliper at timed intervals along the long and short axes of the swelling and bump height. Patients were also assessed for hypoglycemic symptoms using a graded symptom questionnaire in which patients rated the severity of specifically recited hypoglycemia symptoms from 1-5 (1: least severe; 5: most severe) at specific timepoints, from which a "Glucose Rise" score, "Glucose Fall" score, and "All Timepoints" score were calculated. Exendin(9-39) concentration was measured by liquid chromatograph-mass spectrometry as described by Lasaosa et al., supra Example 1.

Figure 6:
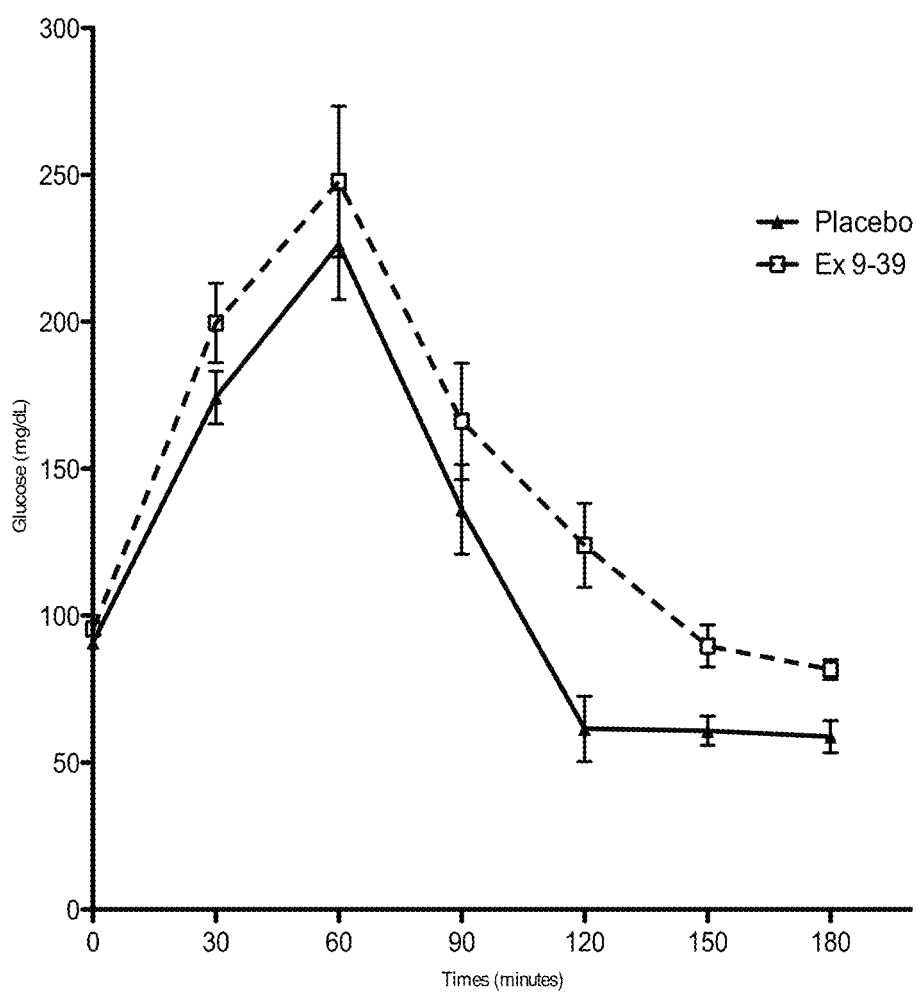
FIG. 6. Average plasma glucose levels during a 75 gram OGTT for subjects administered a subcutaneous dose of exendin(9-39) as compared to baseline. Four subjects received one subcutaneous injection of 35,700 pmol/kg, 75,000 pmol/kg, or 112,500 pmol/kg (approximately 10, 20, or 30 mg, respectively, based on an 80 kg patient) in a volume of 0.7 ml normal saline, and four subjects received two or more 0.7 ml injections of 35,700 pmol/kg, 75,000 pmol/kg, or 112,500 pmol/kg in order to maintain an injectate concentration of 15 mg/ml or less. The average plasma glucose nadir for all 8 subjects during subcutaneous injection of exendin(9-39) was 78 mg/dL vs. <50 mg/dL during a baseline oral glucose tolerance test, demonstrating that subcutaneous injection of a single dose about 10-30 mg exendin(9-39) was able to effectively reverse hyperinsulinemic hypoglycemia.

For the 8 subjects who were administered a subcutaneous dose of 37,500 pmol/kg, 75,000 pmol/kg, or 112,500 pmol/kg, the plasma glucose concentrations were measured during the OGTT. (The dose of 7,500 pmol/kg that was administered to subject 1 was presumed to be subtherapeutic, and so an OGTT was not administered to this subject.) For the remaining eight subjects who were administered a subcutaneous dose of exendin(9-39) and an OGTT, none of the subjects became hypoglycemic after subcutaneous injection at doses ranging from 35,000-112,500 pmol/kg. Thus, prevention of hypoglycemia was achieved at all subcutaneous dose levels. In contrast, all of the subjects receiving placebo became hypoglycemic during the OGTT. As shown in FIG. 6, the average plasma nadir for the 8 subjects administered a subcutaneous dose of exendin(9-39) was 78 mg/dL, versus <50 mg/dL for the placebo. Additionally, as shown in Table 3, the average subject symptomatic response was significantly improved for the subjects who were administered the subcutaneous dose of exendin(9-39) and OGTT, as measured by a dramatically reduced Overall Symptom Score (14.6 vs. 20.6 for placebo) and Symptom Fall Score (4 vs. 22 for placebo).

As shown in Table 4, subcutaneous administration of exendin(9-39) as a single injection at a dose ranging from 37,500 pmol/kg to 112,500 pmol/kg (approximately 10-30 mg) and a constant volume of 0.7 ml was efficacious for preventing hypoglycemia, for example as shown by the plasma glucose nadir. An injectate concentration of approximately 15 mg/ml (the 37,500 pmol/kg dose) resulted in the greatest pharmacodynamic response, as defined by Cmax and dose-normalized Cmax. For the subjects who were subcutaneously administered exendin(9-39) at relatively equivalent concentrations (approximately 13-16 mg/ml), as shown in Table 5, exendin(9-39) administration was efficacious in preventing hypoglycemia, for example as shown by the plasma glucose nadir. For these patients, Table 5 shows that there was an increasingly favorable PK response with increasing dose, as defined by Cmax and $T_{1/2}$.

Figure 8:
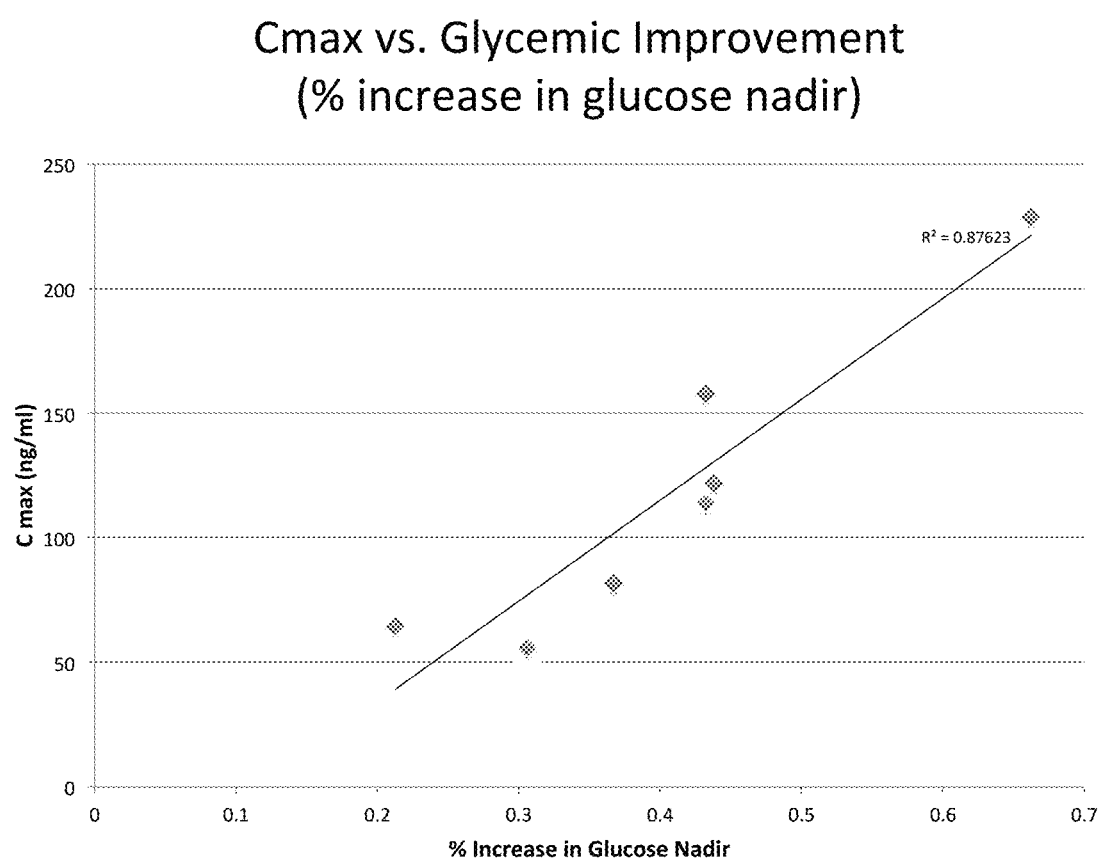
FIG. 8. Percent increase in plasma glucose nadir concentrations were calculated for the subcutaneously administered doses of exendin(9-39) relative to baseline. A correlation was observed between higher percent increases in plasma glucose nadir concentrations and increasing peak plasma exendin(9-39) concentrations ($C_{max}$).

As shown in FIG. 8, a strong correlation was found between the percent increase in plasma glucose nadir concentrations (comparing plasma glucose nadir after subcutaneous injection of exendin(9-39) to baseline plasma glucose nadir) and the peak plasma exendin(9-39) concentrations (Cmax).

Surprisingly, the clinical efficacy achieved for the subcutaneously administered doses of exendin(9-39) tested in this SAD study was equivalent to the efficacy that was achieved by continuous IV infusion of larger quantities of exendin(9-39) as described in Example 1, as shown for example in Table 3 for the plasma glucose nadir, AUC glucose, and the Symptom Fall Score parameters.

In view of the efficacy of the subcutaneously administered dose levels as demonstrated in this example, the efficacy, safety, tolerability, and pharmacokinetics of subcutaneous administration of exendin(9-39) over a defined time period is evaluated, for example, as described in Example 4 and Example 5 below.

4.4 Example 4. Multi-Ascending Dose Trial to Assess the Efficacy, Tolerability, and Pharmacokinetic Profile of BID Exendin(9-39) in Patients with Post-Bariatric Hyperinsulinemic Hypoglycemia This example describes a Phase 2a clinical study protocol for evaluating the safety, tolerability, efficacy, and pharmacokinetic profile of BID exendin(9-39) administered subcutaneously over 3 days to patients with post-bariatric hyperinsulinemic hypoglycemia.

TABLE B

| Study objectives and endpoints | |
|---|---|
| Objective | Endpoint |
| Primary: | |
| To evaluate the treatment effect on plasma glucose of SC BID Ex9 | Response rate in plasma glucose nadir, defined as proportion of patients in each dose arm with no plasma glucose ≤50 mg/dL at any timepoint from 0-180 minutes during OGTT on Day 3 of treatment vs. on Day 0. |
| Secondary: | |
| To evaluate the treatment effect on symptoms of hypoglycemia of SC | Improvement in composite symptom score as compared to baseline during OGTT on Day 3 of |

TABLE B-continued

Study objectives and endpoints

| Objective | Endpoint |
|---|---|
| BID Ex9 | treatment vs. on Day 0. |
| To assess the pharmacokinetics of SC BID Ex9 at each dose level | Plasma PK parameters include $AUC_{0-12h}$, $C_{max}$, $T_{max}$, $T_{1/2}$, and $C_{trough}$, after SC injection. |
| To assess the safety and tolerability of SC BID Ex9 at each dose level | AEs, laboratory parameters, vital signs; NMR score, VAS score. |

Figure 9:
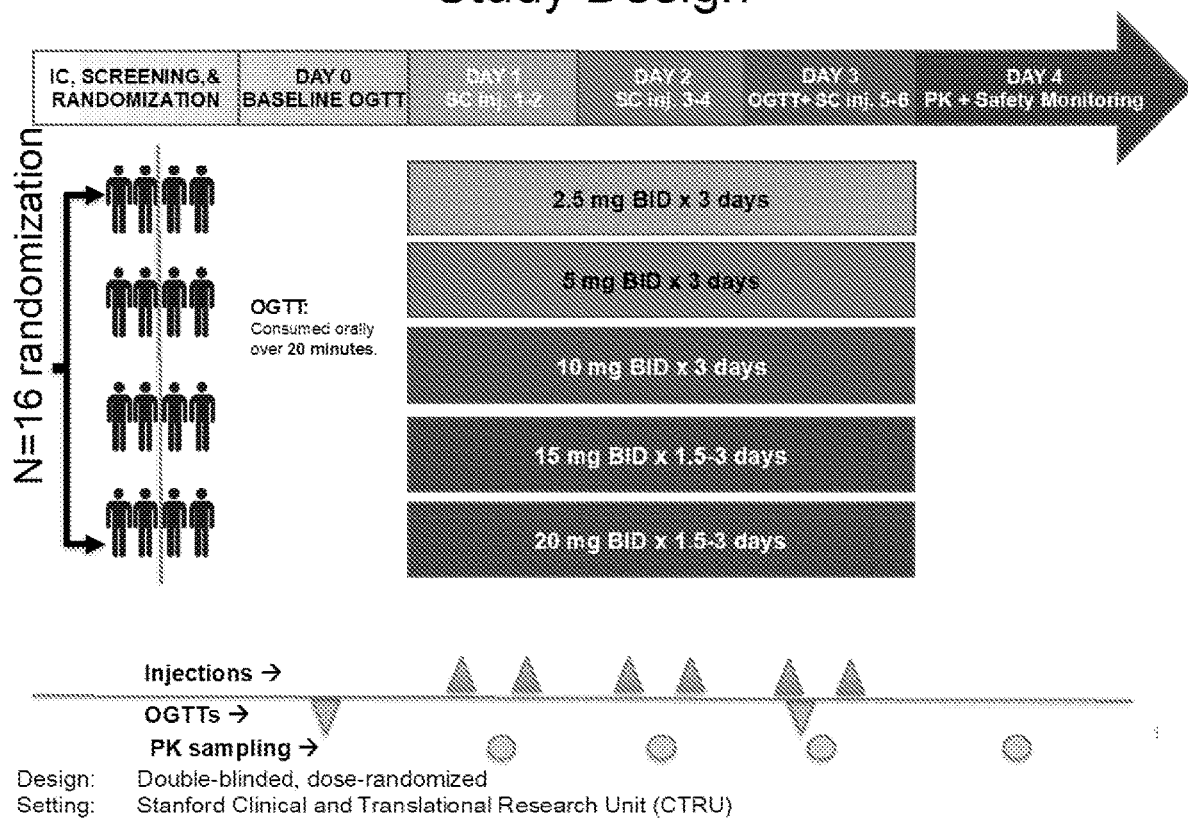
FIG. 9. Study design for 3-day Multi-Ascending Dose Trial to assess the safety, tolerability, efficacy, and pharmacokinetic profile of BID exendin(9-39) administered subcutaneously over 3 days to patients with post-bariatric hyperinsulinemic hypoglycemia.

Overview: The study is a single-blinded, dose-randomized, cross-over design study that is being conducted at the Stanford University School of Medicine. All subject visits will take place in the Clinical and Translational Research Unit (CTRU). Sixteen to twenty eligible subjects will be assigned to one of five dose levels (2.5 mg, 5 mg, 10 mg, 15 mg, 20 mg) to receive subcutaneous injection of BID exendin(9-39) administered for three days. After a baseline Oral Glucose Tolerance Test (OGTT) is conducted on Day 0 wherein metabolic and symptomatic analyses will occur, subjects will return to the research clinic on Day 1 to initiate a BID dosing schedule for 3 days. During this time, subjects will return daily for fasting labs in the morning, a morning dose, PK sampling, and an evening trough sample, followed immediately by the second daily dose at T+720 min. Safety, tolerability, and pharmacokinetic parameters will be measured on a daily basis for the full three day duration of the study, after which a repeat OGTT is performed on the morning of Day 3 after the morning dose to evaluate for efficacy (no hypoglycemia and reduction in composite symptom score). Day 4 will consist solely of clinical safety monitoring with a plasma trough drawn 1440 minutes after the last Day 3 injection. This study if properly conducted is expected to demonstrate that BID dosing can result in meaningful therapeutic activity in each dosing arm. See, FIG. 9.

Randomization/blinding: For the first four subjects dosed, the subjects were randomly assigned to one of the following dose levels: 2.5 mg, 5 mg, or 10 mg. The remaining subjects will be randomly assigned to one of the following dose levels: 10 mg, 15 mg, or 20 mg. All subjects will remain blinded throughout. With the exception of the PI and sub-investigator who will remain un-blinded for safety purposes, all site personnel including nurses and study coordinators, who conduct patient symptom surveys, will remain masked to treatment assignment.

Study drug preparation and dispensation: All doses will be prepared to a total concentration of ≤15 mg/ml of exendin (9-39) in normal saline. Each 10 mg vial of lyophilized exendin(9-39) will be diluted in either 1 ml normal saline if a 10 mg/ml concentration is administered, or 0.7 ml normal saline if a 14 mg/ml concentration is administered. For doses requiring total volume of injection >1 ml, 2 injections will be employed.

Oral Glucose Tolerance Test (OGTT): The OGTT will consist of administration of one 75 mg gram glucola drink with 1 gram of crushed acetaminophen to be consumed over 20 minutes.

Assays: Metabolic: glucose, c-peptide, insulin, GLP-1, GIP, glucagon; PK: $AUC_{0-720}$, $C_{max}$, $T_{max}$, $T_{1/2}$, $C_{trough}$.

Figure 10:
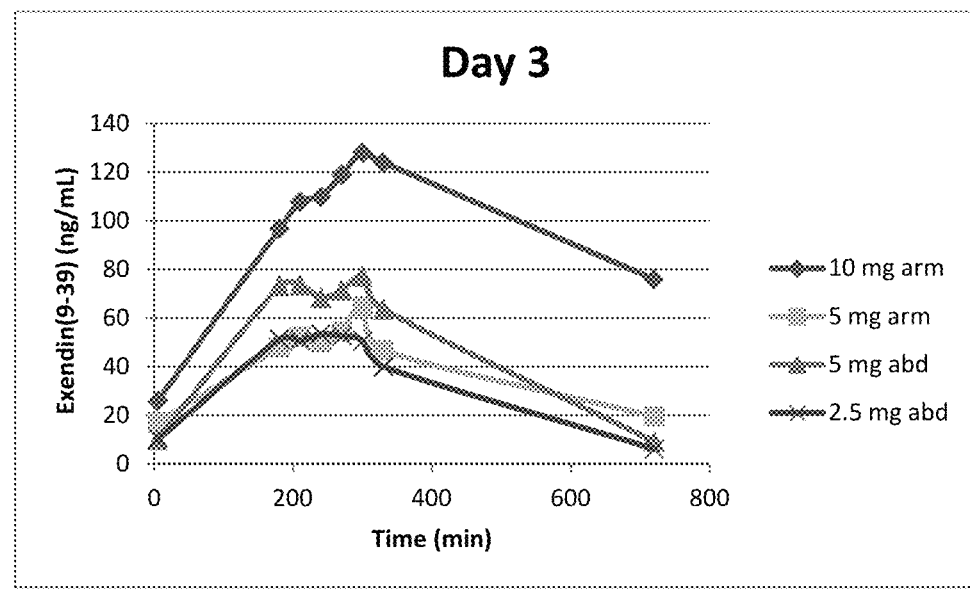
FIG. 10. Exendin(9-39) plasma concentrations on Day 3 after 5 doses as described in Example 4.

Anticipated PK profile: It was anticipated, based on the prior results for a single subcutaneous injection (as shown in Example 3), that after administration of a 5 mg, 10 mg, 15 mg, or 20 mg dose the plasma concentration of exendin(9-39) would return to <20 ng/mL or even close to 0 ng/mL within 720 minutes of injection. However, based on the intermediate results of BID dosing for 3 days as shown in FIG. 10 and as discussed below, it is expected that administration of a 10-30 mg dose will result in a higher nadir, such as a nadir of about 30-80 ng/ml within 720 minutes after injection.

It is expected that a dosage of 5 mg BID, 10 mg, 15 mg or 20 mg BID exendin(9-39) will demonstrate a therapeutic benefit for one or more patients in the 3-day trial. A "therapeutic benefit" may be defined with reference to effect on plasma glucose. For example, in some instances a dosage of exendin(9-39) provides a therapeutic benefit for a patient when the patient has no plasma glucose ≤50 mg/dL at any timepoint from 0-180 minutes during OGTT on Day 3 of treatment as compared to Day 0. In some instances a dosage of exendin(9-39) provides a therapeutic benefit for a patient when the patient has at least a 15% increase in plasma glucose nadir during OGTT on Day 3 relative to Day 0. In some instances a dosage of exendin(9-39) provides a therapeutic benefit for a patient when the patient has at least a 15% increase in AUC glucose. In some instances a dosage of exendin(9-39) provides a therapeutic benefit for a patient when the patient has a statistically significant decrease in the severity of one or more symptoms of hypoglycemia overall during the OGTT and/or of neuroglycopenic symptoms elicited during the glucose "Fall" period of the OGTT relative to Day 0. In some instances a dosage of exendin(9-39) provides a therapeutic benefit for a patient having a plasma glucose nadir ≤50 mg/dL at baseline when the patient exhibits a plasma glucose nadir ≥55 mg/dL after a defined treatment period (e.g., after a 3 day treatment period).

Intermediate results: Four subjects were randomized to one of three dose levels (2.5 mg, 5 mg, or 10 mg) to receive subcutaneous injection of BID exendin(9-39) administered for three days.

Patient 1 was administered a dose of 5 mg at a concentration of 10 mg in 1 ml, subcutaneously administered in the abdomen. For Patient 1, a 13.1% increase in AUC glucose was observed as compared to baseline, but hypoglycemia was not prevented, as defined by plasma glucose ≤50 mg/dL. Patient 2 was administered a dose of 2.5 mg at a concentration of 10 mg in 1 ml, subcutaneously administered in the abdomen. For Patient 2, an 8.8% increase in AUC glucose was observed, but hypoglycemia was not prevented, as defined by plasma glucose 50 mg/dL. Patient 3 was administered a dose of 5 mg at a concentration of 10 mg in 1 ml, subcutaneously administered in the arm. For Patient 3, a 16.3% increase in AUC glucose was observed, but hypoglycemia was not prevented, as defined by plasma glucose ≤50 mg/dL.

Patient 4 was administered a dose of 10 mg at a concentration of 10 mg in 1 ml, subcutaneously administered in the arm. For this patient, hypoglycemia was not prevented, as defined by plasma glucose ≤50 mg/dL.

These intermediate pharmacodynamic results demonstrate an increasing therapeutic benefit, as defined by % increase in glucose AUC with increasing doses administered, with one of the two patients dosed with 5 mg experiencing a greater than 15% increase in AUC glucose as compared to AUC glucose during a baseline oral glucose tolerance test. While hypoglycemia as defined by plasma glucose 50 mg/dL was not prevented, a therapeutic dose response was achieved, illustrating that doses of 10-30 mg will result in improved glycemic control, as further shown by Example 3 and FIG. 8.

The pharmacokinetic parameters obtained from the 3-day BID dosing of Patents 1-4 are shown in Table 6 below. The single subject dosed at 10 mg for 3 days was severely disabled, experiencing daily episodes of symptomatic neuroglycopenia, and requiring placement of gastrostomy tube into the remnant stomach for route of nutrient administration. These intermediate results demonstrate that total exendin(9-39) exposure increases with increasing dose. As shown in Table 6, AUC was increased by about 1.5-1.7-fold, and Cmax was increased by about 50% with a 5 mg dose escalation from 5 mg to 10 mg. Similar degrees of increase are expected to be observed for AUC and Cmax with an escalation to a 15 mg dose. For a 15 mg dose, a Cmax value is expected to be in the therapeutically effective range of approximately 150-200 ng/ml. Interim pharmacokinetic results from this 3-day trial also demonstrate that on average, AUC plasma concentrations increase with increasing days of BID dosing. A higher trough was observed at Day 3 than at Day 1, suggesting several days (e.g., 3-5 days) may be required to reach steady state. Thus, the results of this study support efficacy of the 15 mg dose at Day 3 of treatment. The results of this study also support efficacy of the 10 mg dose in less severely disabled patients and/or with longer (e.g., 5 days) treatment.

Comparison of the pharmacokinetic responses to abdominal versus arm injection of 5 mg doses in patient 1 and patient 3 demonstrates that a quicker absorption profile with higher exposure as defined by Cmax (see Table 6), can be achieved by administration of the injectate into an area with less subcutaneous fat, as may be the abdominal subcutaneous area after bariatric surgery weight loss. A slower absorption profile with longer exposure, as defined by AUClast (see Table 6) can be achieved by administration of the same dose into an area with relatively more subcutaneous fat, such as the arm area may have after bariatric surgery weight loss.

4.5 Example 5: Multiple Doses of Subcutaneously Injected Exendin(9-39) Safely and Effectively Reverse Hyperinsulinemic Hypoglycemia This example demonstrates the method of the invention in which a multi-site multi-ascending dose (MAD) format is used to evaluate the efficacy, safety, and pharmacokinetics of a 28-day trial of immediate release subcutaneous exendin (9-39) administered BID in patients with severe post-bariatric hypoglycemia. The primary objective of this trial is to demonstrate the efficacy of exendin(9-39) on plasma glucose levels during a 3-hour oral Glucose Tolerance Test (OGTT) at the end of 4-week treatment. This trial is also intended to demonstrate the efficacy of exendin(9-39) on the frequency and severity of hypoglycemia incidence and associated symptoms in patients with severe post-bariatric hypoglycemia. This trial also demonstrates the pharmacokinetics and pharmacodynamics of exendin(9-39) at each dose level. Furthermore, this trial demonstrates the safety and tolerability profile of the immediate release subcutaneous formulation of exendin(9-39) in patients with severe post-bariatric hypoglycemia.

This is a multi-center, double-blind, randomized, placebo-controlled, parallel-group, two exendin(9-39) dose levels, phase 2 study in patients with severe post-bariatric hypoglycemia. Approximately 36 patients will be recruited. Eligible patients will have a confirmed diagnosis of severe hypoglycemia post-bariatric via Whipple's triad and OGTT. The study is divided into three phases, as follows:

Screening phase: All potential subjects will complete an oral glucose tolerance test (OGTT), wherein if plasma glucose falls to less than or equal to 60 mg/dL and all other eligibility criteria are met, the patient will be allowed to enroll in the study. In cases of out of range laboratory values, with the exception of laboratory tests related to re-feeding syndrome, subjects are permitted to re-screen one time.

4-week randomized treatment (RT) period: All enrolled subjects will participate in a 4-week randomized treatment period wherein subjects will be randomized to one of two exendin(9-39) doses (e.g., 10 mg and 20 mg, 10 mg and 15 mg, or 15 mg and 20 mg) administered BID or matching placebo of the 2 doses. The ratio of treatment assignment to the first exendin(9-39) BID dose, the second exendin(9-39) BID dose, the first matching placebo dose, and the second matching placebo dose will be 2:2:1:1. During the RT period, the subjects will undergo continuous glucose monitoring wearing Dexcoms at home.

Open-label extension (OLE) period: All patients completing Week 4 of the randomized treatment period and experiencing benefit with exendin(9-39) at the end of RT will be eligible to enter the OLE period. During the OLE period, the dose administered will either be an optimal fixed dose level selected at the end of the randomized treatment period of the study or up-titrated to 20 mg BID until any of the following occur: completed 12 months of the open-label extension; unacceptable toxicity; lack of efficacy; protocol deviation; patient withdrew consent; lost to follow-up; death; and study discontinues per the sponsor.

The primary efficacy endpoint is measured as the response rate in plasma glucose level at the end of the 4-week RT, defined as the proportion of patients either (1) without plasma glucose ≤55 mg/dL for patients whose glucose nadir is ≤50 mg/dL at baseline OGTT; or (2) without plasma glucose ≤60 mg/dL for patients whose glucose nadir is 55-≤60 mg/dL at baseline OGTT. Secondary efficacy endpoints are measured as the improvement in neuroglycopenic symptom score during OGTT at the end of RT (Week 4), where neuroglycopenic symptoms include inability to concentrate, confusion, weakness, drowsiness, dizziness, blurred vision, difficulty speaking (modified from the Edinburgh Hypoglycemia Score, Hepburn 1991); the proportion of patients with severe hypoglycemia during the 4-week RT, where severe hypoglycemia is defined an event requiring assistance of another person to actively administer carbohydrates, glucagon, or take other corrective actions with a blood glucose concentration of <50 mg/dL by continuous glucose monitoring (CGM); the proportion of patients with any hypoglycemia event between Week 2 and Week 4, where hypoglycemia is defined as a plasma glucose concentration of ≤55 mg/dL by continuous glucose monitoring (CGM) [Hypoglycemia after Roux-En-Y gastric bypass: detection rates of continuous glucose monitoring (CGM) versus mixed meal test Kefurt 2014]; and the Change in Quality of life at Week 4 from baseline as evaluated using Short-Form 36 (SF-36) domain scores.

The pharmacokinetic and pharmacodynamics endpoints to be measured include $C_{max}$, $T_{max}$, $T_{1/2}$, $C_{trough}$, AUC of exendin(9-39). Exploratory endpoints will include insulin (AUC, Peak, ISR, ICR), GLP-1/GIP, and glucagon concentrations.

4.6 Example 6: Diminished Novelty Preference Scores on the Visual Paired Comparison Test in Patients with Hyperinsulinemic Hypoglycemia as Compared to Insulin Sensitive Healthy Controls Predicts Mild Cognitive Impairment Indicative of Cumulative Hyperinsulinemic Hypoglycemia Effects This example describes one embodiment of the method of invention which is conducted as a pilot study to evaluate whether patients with hyperinsulinemic hypoglycemic exhibit early signs of amnestic mild cognitive impairment (aMCI) in comparison to health controls, and therein may benefit from GLP1A for prevention of further cognitive decline. In this design, six patients with hyperinsulinemic hypoglycemia and six sex- and age-matched insulin sensitive controls are enrolled. Participants arrive at the research clinic fasted for 12 hours. They are seated in front of a monitor, with eye position calibrated for each participant using a 9-point array. System parameters are adjusted until the participant's fixations accurately mapped onto the calibration points. Participants are told that images will appear on the computer screen and are instructed to look at the images "as if watching television." During testing, the participants eye fixations and eye movements are recorded throughout the 2 phases of the Visual Paired Comparison (VPC) test; a familiarization phase followed by a test phase. During the familiarization phase, 2 identical images are presented side by side on the monitor for 5 seconds. The monitor then goes dark for a delay interval of 2 seconds. In the test phase, 2 images are again presented side by side for 5 seconds. One of the images is identical to the image presented during the familiarization phase and the other was a novel image. Presentation of the novel image on the left or right side is selected pseudo randomly and distributed equally.

Figure 11:
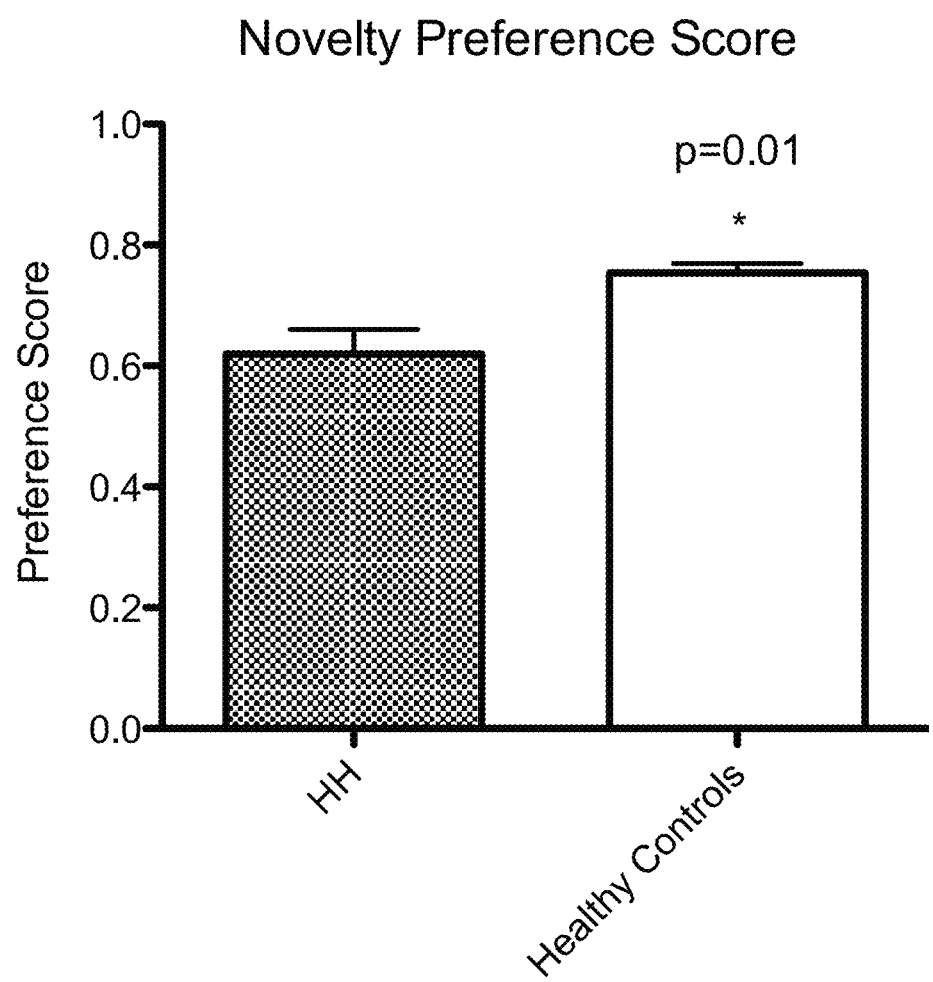
FIG. 11. Diminished novelty preference scores on the Visual Paired Comparison (VPC) Test in patients with hyperinsulinemic hypoglycemia as compared to insulin sensitive healthy controls predicts mild cognitive impairement indicative of cumulative hyperinsulinemic hypoglycemia effects. As described in Example 6, patients with hyperinsulinemic hypoglycemia exhibited early signs of amnestic mild cognitive impairment (aMCI) as measured by the VPC test in comparison to healthy controls, and therein may benefit from GLP1A for prevention of further cognitive decline.

Eye fixation and movement data for each participant are extracted and analyzed, with fixation defined as a point of gaze continually remaining for a period of 100 milliseconds or more looking at the area of either the novel image or the area of the familiar image. Eye data are characterized using percent looking time on the novel image, shown in FIG. 11 as "Novelty Preference Score." As shown in FIG. 11, patients with hyperinsulinemic hypoglycemia scored lower than matched controls, and one can extrapolate that this condition may confer higher risk of conversion to aMCI or Alzheimer's disease than healthy controls. Given that hyperinsulinemic hypoglycemia is a lifelong condition, and patients with this condition typically have multiple episodes of hypoglycemia per week, the cumulative effects on cognition may be substantial. Prevention of such episodes with the method of the invention could have long-ranging effects, such as prevention of cognitive decline.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

TABLE 1

Subject metabolic responses to OGTT with and without intravenous infusion of Exendin (9-39) vs. non-surgical controls

|  | HH Placebo[a] (n = 8) | HH Ex(9-39)[a] | Non-Surg controls[a] (n = 8) | P-value[b] | P-value[c] | P-value[d] |
|---|---|---|---|---|---|---|
| Fasting plasma glucose (mg * dl$^{-1}$) | 91.8 ± 1.2 | 94.7 ± 3.9 | 100.6 ± 4.3 | 0.414 | 0.06 | 0.322 |
| Peak postprandial glucose (mg * dl$^{-1}$) | 235.4 ± 11.0 | 225.5 ± 15.1 | 152.3 ± 6.1 | 0.432 | 0.000 | 0.001 |
| Time to peak glucose (min) | 56.3 ± 3.8 | 37.5 ± 4.9 | 45.0 ± 5.7 | 0.011 | 0.120 | 0.334 |
| Nadir postprandial glucose (mg * dl$^{-1}$) | 46.1 ± 1.9 | 78.7 ± 5.4 | 74.9 ± 3.8 | 0.000 | 0.000 | 0.570 |
| Time to hypoglycemia (min) | 137.5 ± 5.3 | NA | NA | NA | NA | NA |
| Delta peak-nadir glucose (mg * dl$^{-1}$) | 189.3 ± 10.1 | 146.8 ± 15.3 | 77.4 ± 7.6 | 0.012 | 0.000 | 0.001 |
| Rate of glucose decline (mg * dl$^{-1}$ * min$^{-1}$) | 3.1 ± 0.5 | 1.1 ± 0.3 | 0.5 ± 0.2 | 0.001 | 0.001 | 0.189 |
| AUC glucose (0, 60)(mg * dl$^{-1}$ * min$^{-1}$) | 10402.5 ± 309.3 | 10905.9 ± 624.1 | 8120.6 ± 287.1 | 0.278 | 0.000 | 0.001 |
| AUC glucose(60, 180)(mg * dl$^{-1}$ * min$^{-1}$) | 11318.9 ± 573.3 | 15397.5 ± 1180.7 | 13346.3 ± 504.9 | 0.010 | 0.019 | 0.378 |
| AUC glucose(0, 180)(mg * dl$^{-1}$ * min$^{-1}$) | 21721.4 ± 701.8 | 26303.4 ± 1785.8 | 21466.9 ± 642.2 | 0.020 | 0.793 | 0.023 |
| Fasting plasma insulin (uU * ml$^{-1}$) | 4.0 ± 19.2 | 3.2 ± 0.8 | 15.0 ± 1.2 | 0.260 | 0.000 | 0.000 |
| Peak postprandial insulin (uU * ml$^{-1}$) | 200.3 ± 28.5 | 88.3 ± 23.0 | 86.0 ± 8.3 | 0.000 | 0.002 | 0.928 |
| Time to peak insulin (min) | 60.0 ± 5.7 | 48.8 ± 5.5 | 67.5 ± 12.4 | 0.285 | 0.590 | 0.187 |
| AUC insulin (0, 60)(uU * ml$^{-1}$ * min$^{-1}$) | 6220.3 ± 766.4 | 3368.9 ± 832.4 | 3420.0 ± 375.7 | 0.001 | 0.005 | 0.956 |
| AUC insulin (60, 180)(uU * ml$^{-1}$ * min$^{-1}$) | 4591.6 ± 876.3 | 2462.2 ± 524.8 | 6532.5 ± 607.9 | 0.038 | 0.090 | 0.000 |
| AUC insulin (0, 180)(uU * ml$^{-1}$ * min$^{-1}$) | 13605.5 ± 1819.0 | 5831.1 ± 1281.0 | 9952.5 ± 869.9 | 0.001 | 0.092 | 0.019 |
| Insulin at glucose <55 mg/dl (uU * ml$^{-1}$) | 17.5 ± 4.7 | NA | NA | NA | NA | NA |
| Insulinogenic Index (0, 30) | 1.2 ± 0.2 | 0.7 ± 0.2 | 1.2 ± 0.4 | 0.001 | 0.927 | 0.286 |
| Insulinogenic Index (0, 60) | 1.4 ± 0.2 | 0.6 ± 0.1 | 1.9 ± 0.4 | 0.000 | 0.239 | 0.006 |

[a]Data are presented as mean ± SEM
[b-d]p-value by two-sided student's t-test
[b]P-value HH Placebo vs. HH Ex(9-39)
[c]P-value HH Placebo vs. Non-Surg Controls
[d]P-value HH Ex(9-39) vs. Non-Surg Controls

TABLE 2

Subject incretin responses to OGTT with and without intravenous infusion of Exendin (9-39)

| | HH Placebo[a] (n = 8) | HH Ex(9-39)[a] (n = 8) | P-value[b] |
|---|---|---|---|
| Fasting GLP-1 (pmol * L$^{-1}$) | 9.0 ± 0.4 | 9.4 ± 1.2 | 0.191 |
| Peak GLP-1 (pmol * L$^{-1}$) | 86.0 ± 6.1 | 82.3 ± 13.9 | 0.857 |
| Time to peak GLP-1 (min) | 42.9 ± 6.1 | 38.6 ± 5.5 | 0.604 |
| AUC GLP-1 (0, 60)(pmol * L$^{-1}$ * min$^{-1}$) | 3270.0 ± 214.1 | 3267.9 ± 606.8 | 0.998 |
| AUC GLP-1 (60, 180)(pmol * L$^{-1}$ * min$^{-1}$) | 3135.7 ± 265.7 | 3621.4 ± 416.0 | 0.429 |
| AUC GLP-1 (0, 180)(pmol * L$^{-1}$ * min$^{-1}$) | 6405.7 ± 423.0 | 6889.3 ± 941.2 | 0.700 |
| Peak Insulin to Peak GLP-1 ratio | 2.6 ± 0.1 | 1.3 ± 0.4 | 0.059 |
| Fasting GIP (pmol * L-1 * min-1) | 14.4 ± 1.4 | 14.0 ± 1.5 | 0.824 |
| Peak GIP (pmol * L-1 * min-1) | 93.1 ± 12.8 | 86.6 ± 12.0 | 0.005 |
| Time to peak GIP (min) | 42.9 ± 6.0 | 34.3 ± 4.3 | 0.356 |
| AUC GIP (0, 60)(pmol * L$^{-1}$ * min$^{-1}$) | 3831.4 ± 495.9 | 3267.9 ± 606.8 | 0.127 |
| AUC GIP (60, 180)(pmol * L$^{-1}$ * min$^{-1}$) | 3722.1 ± 168.9 | 3165.0 ± 396.9 | 0.084 |
| AUC GIP (0, 180)(pmol * L$^{-1}$ * min$^{-1}$) | 7553.6 ± 617.9 | 6420.0 ± 941.2 | 0.003 |
| Peak Insulin to Peak GIP ratio | 2.4 0.4 | 1.3 0.4 | 0.000 |
| Fasting glucagon (pmol * L$^{-1}$) | 40.5 ± 2.8 | 41.9 ± 2.9 | 0.567 |
| Peak glucagon (pmol * L$^{-1}$) | 82.8 ± 6.7 | 92.3 ± 6.4 | 0.079 |
| Time to peak glucagon (min) | 60.0 ± 12.7 | 45.0 ± 11.3 | 0.470 |
| AUC glucagon (0, 60)(pmol * L$^{-1}$ * min$^{-1}$) | 3796.6 ± 306.2 | 4430.5 ± 285.1 | 0.033 |
| AUC glucagon (60, 180)(pmol * L$^{-1}$ * min$^{-1}$) | 7999.8 ± 912.2 | 8017.5 ± 696.3 | 0.981 |
| AUC glucagon (0, 180)(pmol * L$^{-1}$ * min$^{-1}$) | 11584.4 ± 1252.9 | 12019.3 ± 941.9 | 0.981 |

| | Placebo[a] (n = 8) | SC Ex(9-39)[a] (n = 8) | IV Ex(9-39)[a] (n = 8) | P-value[b] | P-value[c] |
|---|---|---|---|---|---|
| Subject metabolic response | | | | | |
| Fasting plasma glucose (mg * dl$^{-1}$) | 91.6 ± 1.7 | 94.5 ± 1.7 | 94.7 ± 3.9 | 0.125 | 0.966 |
| Peak postprandial glucose (mg * dl$^{-1}$) | 229.3 ± 13.2 | 252.3 ± 23.7 | 225.5 ± 15.1 | 0.258 | 0.358 |
| Time to peak glucose (min) | 54.5 ± 3.7 | 52.5 ± 4.9 | 37.5 ± 4.9 | 0.351 | 0.049 |
| Nadir postprandial glucose (mg * dl$^{-1}$) | 47.7 ± 1.6 | 77.9 ± 4.1 | 78.7 ± 5.4 | <.001 | 0.906 |
| Time to hypoglycemia (min) | 135.5 ± 4.9 | NA | NA | NA | NA |
| Delta peak-nadir glucose (mg * dl$^{-1}$) | 182.0 ± 11.0 | 174.4 ± 24.2 | 146.8 ± 15.3 | 0.588 | 0.351 |
| Rate of glucose decline (mg * dl$^{-1}$ * min$^{-1}$) | 2.9 ± 0.4 | 2.4 ± 0.7 | 1.1 ± 0.3 | 0.402 | 0.117 |
| AUC glucose (0, 60)(mg * dl$^{-1}$ * min$^{-1}$) | 10171.4 ± 334.6 | 11135.6 ± 704.4 | 10905.9 ± 624.1 | 0.140 | 0.811 |
| AUC glucose(0, 180)(mg * dl$^{-1}$ * min$^{-1}$) | 21106 ± 1001.6 | 27471.6 ± 1963.0 | 26303.4 ± 1785.8 | 0.007 | 0.667 |
| Subject symptomatic response | | | | | |
| Overall Symptom Score[∧] | 26 ± 3.3 | 14.6 ± 4.4 | 4.5 ± 2.2 | 0.006 | 0.057 |
| Symptom Rise Score+ | 11 ± 2.4 | 12.3 ± 3.7 | 4.3 ± 2.2 | 0.794 | 0.087 |
| Symptom Fall Score * | 22 ± 3.5 | 4.0 ± 1.5 | 1.1 ± 0.4 | 0.001 | 0.091 |

[a]Data are presented as mean ± SEM
[b-c]P-value by two-sided paired student's t-test
[b]P-value SC Ex(9-39) vs. Placebo
[c]P-value SC Ex(9-39) vs. IV Ex(9-39)

TABLE 4

| | 37500 pmol/kg n = 1 | 75000 pmol/kg n = 2 | 125000 pmol/kg n = 1 |
|---|---|---|---|
| Injectate Characteristics | | | |
| Fold-increase in dose relative to 7,500 pmol/kg | 5x | 10x | 15x |
| Concentration (mg/ml) | 15.714 | 23.57 | 41.43 |
| Total dose administered (mg) | 11 | 17 | 29 |
| Volume per injection (ml) | 0.7 | 0.7 | 0.7 |
| Number of injections | 1 | 1 | 1 |

TABLE 4-continued

| | 37500 pmol/kg n = 1 | 75000 pmol/kg n = 2 | 125000 pmol/kg n = 1 |
|---|---|---|---|
| Subject Pharmacodynamic Response | | | |
| Fasting plasma glucose (mg*dl$^{-1}$) | 94 | 95.8 | 103.5 |
| Peak postprandial glucose (mg*dl$^{-1}$) | 244 | 226.8 | 311.0 |
| Time to peak glucose (min) | 60 | 60 | 60 |
| Nadir postprandial glucose (mg*dl$^{-1}$) | 88 | 71.3 | 58.0 |
| Delta peak-nadir glucose (mg*dl$^{-1}$) | 156 | 155.5 | 253.0 |
| Rate of glucose decline (mg*dl$^{-1}$*min$^{-1}$) | 1 | 2.2 | 6.7 |
| AUC glucose (0.60)(mg*dl$^{-1}$*min$^{-1}$) | 10815 | 9694 | 12713 |
| AUC glucose(0.180)(mg*dl$^{-1}$*min$^{-1}$) | 28482 | 25151 | 25718 |

TABLE 4-continued

|  | 37500 pmol/kg n = 1 | 75000 pmol/kg n = 2 | 125000 pmol/kg n = 1 |
|---|---|---|---|
| Subject Pharmacokinetic Response | | | |
| Cmax (ng/ml) | 114 | 73.35 | 56 |
| DN Cmax (ng/mL/mg) | 10.36 | 4.45 | 1.93 |
| Tmax (h) | 3.25 | 6.25 | 5.00 |
| AUCINF [h*ng/ml] | 1097 | 1210 | 728 |
| DN_AUC$_{INF}$ [h*ng/ml/mg] | 69 | 63 | 24 |
| AUC$_{last}$ (h*ng/ml] | 1084 | 696 | 720 |
| T$^{1/2}$(h) | 3.60 | 9.14 | 3.64 |
| MRT$_{last}$ [h]) | 6.16 | 5.74 | 6.62 |
| MRT$_{INF}$ [h] | 6.45 | 14.66 | 6.87 |

TABLE 5

|  | 37500 pmol/kg n = 1 | 75000 pmol/kg n = 1 | 112500 pmol/kg n = 2 |
|---|---|---|---|
| Injectate Characteristics | | | |
| Fold-increase in dose relative to 7,500 pmol/kg | | | |
| Concentration (mg/ml) | 15.714 | 14.71 | 13.48 |
| Total dose administered (mg) | 11 | 21 | 29 |
| Volume per injection (ml) | 0.7 | 0.7 | 0.7 |
| Number of injections | 1 | 2 | 3 |
| Subject Pharmacodynamic Response | | | |
| Fasting plasma glucose (mg*dl$^{-1}$) | 94 | 90 | 90.0 |
| Peak postprandial glucose (mg*dl$^{-1}$) | 244 | 187.0 | 228.0 |
| Time to peak glucose (min) | 60 | 30 | 45 |
| Nadir postprandial glucose (mg*dl$^{-1}$) | 88 | 75.5 | 85.0 |
| Delta peak-nadir glucose (mg*dl$^{-1}$) | 156 | 111.5 | 143.0 |
| Rate of glucose decline (mg*dl$^{-1}$*min$^{-1}$) | 1 | 0.6 | 1.5 |
| AUC glucose (0.60)(mg*dl$^{-1}$*min$^{-1}$) | 10815 | 9540 | 11063 |
| AUC glucose(0.180)(mg*dr$^{-1}$*min$^{-1}$) | 28482 | 21023 | 27274 |
| Subject Pharmacokinetic Response | | | |
| Cmax (ng/ml) | 114 | 158 | 229 |
| DN Cmax (ng/mL/mg) | 10.36 | 7.52 | 7.9 |

TABLE 5-continued

|  | 37500 pmol/kg n = 1 | 75000 pmol/kg n = 1 | 112500 pmol/kg n = 2 |
|---|---|---|---|
| Tmax (h) | 3.25 | 4.50 | 4.50 |
| AUCINF [h*ng/ml] | 1097 | 1516 | 1885 |
| DN_AUC$_{INF}$ [h*ng/ml/mg] | 69 | 101 | 67 |
| AUC$_{last}$ (h*ng/ml) | 1084 | 900 | 1055 |
| T$^{1/2}$(h) | 3.60 | 4.59 | 4.87 |
| MRT$_{last}$ [h]) | 6.16 | 4.39 | 4.69 |
| MRT$_{INF}$ [h] | 6.45 | 8.55 | 9.24 |

TABLE 6

| Dose | 2.5 mg | 5 mg | 5 mg | 10 mg |
|---|---|---|---|---|
| Number of subjects dosed | n = 1 | n = 1 | n = 1 | n = 1 |
| Injectate Characteristics | | | | |
| Dose (mg) | 2.5 | 5 | 5 | 10 |
| Concentration (mg/ml) | 10 mg/ml | 10 mg/ml | 10 mg/ml | 10 mg/ml |
| Volume per injection (ml) | 0.25 ml | 0.5 ml | 0.5 ml | 1 ml |
| Number of injections | 1 | 1 | 1 | 1 |
| Location of administration | abdomen | abdomen | arm | arm |
| Subject Pharmacodynamic Response | | | | |
| % increase AUC glucose (treatment-baseline) | 8.8 | 13.1 | 16.3 | N/A |
| Plasma glucose nadir ≤50 mg/dL (Yes/No) | Yes | Yes | Yes | Yes |
| Subject Pharmacokinetic Response | | | | |
| Day 3 Cmax (ng/ml) | 53.4 | 77.2 | 65 | 128 |
| DN Cmax (ng/mL/mg) | 21.36 | 15.44 | 13 | 12.8 |
| Tmax Day 3 (h) | 4 | 5 | 5 | 5 |
| AUClast (h*ng/ml] | 379.2 | 409.1 | 684.3 | 969 |
| T1/2(h) | 4.3 | 4.4 | 4.6 | 6.5 |

The invention claimed is:

1. A method for treating hyperinsulinemic hypoglycemia in a subject, the method comprising subcutaneously administering to the subject in need thereof a therapeutically effective amount of exendin(9-39);
    wherein the therapeutically effective amount is 2-100 mg of exendin(9-39);
    wherein the exendin(9-39) is administered at a concentration of 20-45 mg/ml; and
    wherein the subject exhibits one or more of Whipple's triad, the occurrence of capillary glucose ≤50 mg/dL at least once per month, and a plasma glucose concentration of ≤60 mg/dL during a tolerance test.

2. The method of claim 1, wherein the tolerance test is an oral glucose tolerance test or a meal tolerance test.

3. The method of claim 1, wherein the subject exhibits a plasma glucose concentration of ≤55 mg/dL and plasma insulin ≥3 uU/mL during the tolerance test, or wherein the subject exhibits a plasma glucose concentration of ≤55 mg/dL and c-peptide >0.3 mg/dL during the tolerance test.

4. The method of claim 1, wherein the therapeutically effective amount is 10-20 mg of exendin(9-39).

5. The method of claim 1, wherein the exendin(9-39) is administered once per day.

6. The method of claim 1, wherein the exendin(9-39) is administered twice per day.

7. The method of claim 1, wherein the subject has previously had bariatric surgery.

8. The method of claim 7, wherein the bariatric surgery is Roux-en-Y gastric bypass, vertical sleeve gastrectomy, placement of an endosleeve device, duodenal mucosal resurfacing, partial bypass of the duodenum, vagal nerve blockade, or pyloroplasty.

9. The method of claim 1, wherein the subject has previously had gastrointestinal surgery.

10. The method of claim 9, wherein the gastrointestinal surgery is gastrectomy, Nissen Fundoplication, or esophagectomy.

11. A method for treating hyperinsulinemic hypoglycemia in a subject, the method comprising subcutaneously administering to the subject in need thereof a therapeutically effective amount of exendin(9-39),
wherein the therapeutically effective amount is 2-100 mg of exendin(9-39);
wherein the exendin(9-39) is administered at a concentration of 20-45 mg/ml; and
wherein the subject is prediabetic and/or insulin resistant.

12. The method of claim 11, wherein the subject has a congenital, acquired, or induced form of hyperinsulinemic hypoglycemia.

13. The method of claim 11, wherein the therapeutically effective amount is 10-20 mg of exendin(9-39).

14. The method of claim 11, wherein the exendin(9-39) is administered once per day.

15. The method of claim 11, wherein the exendin(9-39) is administered twice per day.

16. The method of claim 11, wherein the subject has previously had bariatric surgery.

17. The method of claim 16, wherein the bariatric surgery is Roux-en-Y gastric bypass, vertical sleeve gastrectomy, placement of an endosleeve device, duodenal mucosal resurfacing, partial bypass of the duodenum, vagal nerve blockade, or pyloroplasty.

18. The method of claim 11, wherein the subject has previously had gastrointestinal surgery.

19. The method of claim 18, wherein the gastrointestinal surgery is gastrectomy, Nissen Fundoplication, or esophagectomy.

20. A method for treating hyperinsulinemic hypoglycemia in a subject, the method comprising administering to the subject in need thereof a therapeutically effective amount of exendin(9-39) twice-per-day (BID);
wherein the therapeutically effective amount is 2-100 mg of exendin(9-39);
wherein the exendin(9-39) is administered at a concentration of 20-45 mg/ml; and
wherein the second daily dose is administered 7 to 15 hours after the first daily dose.

21. The method of claim 20, wherein the therapeutically effective amount is 10-20 mg of exendin(9-39).

22. The method of claim 20, wherein the subject has previously had bariatric surgery.

23. The method of claim 22, wherein the bariatric surgery is Roux-en-Y gastric bypass, vertical sleeve gastrectomy, placement of an endosleeve device, duodenal mucosal resurfacing, partial bypass of the duodenum, vagal nerve blockade, or pyloroplasty.

24. The method of claim 20, wherein the subject has previously had gastrointestinal surgery.

25. The method of claim 24, wherein the gastrointestinal surgery is gastrectomy, Nissen Fundoplication, or esophagectomy.

* * * * *